US012753448B2

(12) United States Patent
Bercovici et al.

(10) Patent No.: US 12,753,448 B2
(45) Date of Patent: Oct. 6, 2026

(54) DETECTION AND PREDICTION OF INFECTIOUS DISEASE

(71) Applicant: KARIUS, INC., Redwood City, CA (US)

(72) Inventors: Sivan Bercovici, Redwood City, CA (US); Lily Blair, Redwood City, CA (US); Timothy A. Blauwkamp, Redwood City, CA (US); Peter J. Eugster, Redwood City, CA (US); Desiree Hollemon, Redwood City, CA (US); David K. Hong, Redwood City, CA (US); Trupti Kawli, Redwood City, CA (US); Mark Alec Kowarsky, Redwood City, CA (US); Martin M. S. Lindner, Redwood City, CA (US); Michael J. Rosen, Redwood City, CA (US); Damek Spacek, Redwood City, CA (US); Igor D. Vilfan, Redwood City, CA (US)

(73) Assignee: Karius, Inc., Redwood City, CA (US)

( * ) Notice: Subject to any disclaimer, the term of this patent is extended or adjusted under 35 U.S.C. 154(b) by 1350 days.

(21) Appl. No.: 17/323,834

(22) Filed: May 18, 2021

(65) Prior Publication Data

US 2021/0403986 A1 Dec. 30, 2021

Related U.S. Application Data

(63) Continuation of application No. PCT/US2019/062665, filed on Nov. 21, 2019.
(Continued)

(51) Int. Cl.

| | |
|---|---|
| ***C12Q 1/689*** | (2018.01) |
| ***C12Q 1/6806*** | (2018.01) |
| ***C12Q 1/6869*** | (2018.01) |
| ***C12Q 1/6883*** | (2018.01) |

(Continued)

(52) U.S. Cl.
CPC ........... *C12Q 1/689* (2013.01); *C12Q 1/6806* (2013.01); *C12Q 1/6883* (2013.01); *C12Q 1/701* (2013.01);
(Continued)

(58) Field of Classification Search
None
See application file for complete search history.

(56) References Cited

U.S. PATENT DOCUMENTS

| | | | |
|---|---|---|---|
| 6,753,137 | B2 | 6/2004 | Lo et al. |
| RE39,920 | E | 11/2007 | Umansky et al. |

(Continued)

FOREIGN PATENT DOCUMENTS

| | | | |
|---|---|---|---|
| CA | 3030038 | A1 | 1/2018 |
| CN | 105112569 | A | 12/2015 |

(Continued)

OTHER PUBLICATIONS

Ricci et al. (Diagnosis of Helicobacter pylori: Invasive and non-invasive tests, Best Practice & Research Clinical Gastroenterology, published Apr. 2007). (Year: 2007).*

(Continued)

*Primary Examiner* — Heather Calamita
*Assistant Examiner* — Elizabeth Rose Lafave
(74) *Attorney, Agent, or Firm* — Wilson Sonsini Goodrich & Rosati

(57) ABSTRACT

Provided herein are fragment length profiles of nucleic acid libraries, methods of generating fragment length profiles of nucleic acid libraries and methods of using fragment length profiles for diagnostics and/or prognostics. The application further provides methods, compositions and kits for determining the infection stage or the site of localization in a subject.

22 Claims, 45 Drawing Sheets

Related U.S. Application Data

(60) Provisional application No. 62/849,618, filed on May 17, 2019, provisional application No. 62/770,181, filed on Nov. 21, 2018, provisional application No. 62/770,182, filed on Nov. 21, 2018.

(51) Int. Cl.

| | |
|---|---|
| ***C12Q 1/6886*** | (2018.01) |
| ***C12Q 1/70*** | (2006.01) |
| ***C40B 30/06*** | (2006.01) |
| ***C40B 40/06*** | (2006.01) |
| ***C40B 50/06*** | (2006.01) |

(52) U.S. Cl.

CPC ......... *C12Q 1/6869* (2013.01); *C12Q 1/6886* (2013.01); *C12Q 2525/191* (2013.01); *C12Q 2525/204* (2013.01); *C12Q 2535/122* (2013.01); *C12Q 2535/138* (2013.01); *C12Q 2537/165* (2013.01); *C12Q 2545/101* (2013.01); *C12Q 2600/142* (2013.01); *C40B 30/06* (2013.01); *C40B 40/06* (2013.01); *C40B 50/06* (2013.01)

(56) References Cited

U.S. PATENT DOCUMENTS

| | | | |
|---|---|---|---|
| 7,803,929 | B2 | 9/2010 | Melkonyan et al. |
| 7,914,982 | B2 | 3/2011 | Melkonyan et al. |
| 7,973,154 | B2 | 7/2011 | Melkonyan et al. |
| 8,682,592 | B2 | 3/2014 | Rabinowitz et al. |
| 8,703,652 | B2 | 4/2014 | Quake et al. |
| 8,715,967 | B2 | 5/2014 | Casbon et al. |
| 8,877,442 | B2 | 11/2014 | Quake et al. |
| 9,194,006 | B2 | 11/2015 | Exner et al. |
| 9,353,414 | B2 | 5/2016 | Fan et al. |
| 9,892,230 | B2 | 2/2018 | Lo et al. |
| 9,976,181 | B2 | 5/2018 | Christians et al. |
| 10,240,200 | B2 | 3/2019 | Koh et al. |
| 10,450,620 | B2 | 10/2019 | De Vlaminick et al. |
| 10,697,008 | B2 | 6/2020 | Blauwkamp et al. |
| 11,078,532 | B2 | 8/2021 | Christians et al. |
| 11,111,520 | B2 | 9/2021 | Blauwkamp et al. |
| 11,254,980 | B1 | 2/2022 | Emerson et al. |
| 12,320,036 | B2 | 6/2025 | Bercovici et al. |
| 2004/0209299 | A1 | 10/2004 | Pinter et al. |
| 2005/0048505 | A1 | 3/2005 | Fredrick et al. |
| 2005/0202414 | A1 | 9/2005 | Jia et al. |
| 2006/0073506 | A1 | 4/2006 | Christians et al. |
| 2007/0072212 | A1 | 3/2007 | Vinayagamoorthy |
| 2007/0111233 | A1 | 5/2007 | Bianchi et al. |
| 2010/0029498 | A1 | 2/2010 | Gnirke et al. |
| 2010/0068711 | A1 | 3/2010 | Umansky et al. |
| 2010/0209908 | A1 | 8/2010 | Procop et al. |
| 2011/0160290 | A1 | 6/2011 | Tewari |
| 2012/0021412 | A1 | 1/2012 | Melkonyan et al. |
| 2012/0021919 | A1 | 1/2012 | Scholl et al. |
| 2012/0058521 | A1 | 3/2012 | Church et al. |
| 2012/0077185 | A1 | 3/2012 | Oliphant et al. |
| 2012/0190663 | A1 | 7/2012 | Gornik et al. |
| 2012/0283110 | A1 | 11/2012 | Shendure et al. |
| 2013/0005585 | A1 | 1/2013 | Anderson et al. |
| 2013/0024127 | A1 | 1/2013 | Stuelpnagel et al. |
| 2013/0178544 | A1 | 7/2013 | Melkonyan et al. |
| 2013/0245961 | A1 | 9/2013 | Lo et al. |
| 2013/0252835 | A1 | 9/2013 | Koh et al. |
| 2014/0066317 | A1 | 3/2014 | Talasaz |
| 2014/0147851 | A1 | 5/2014 | Qian et al. |
| 2014/0155274 | A1 | 6/2014 | Xie et al. |
| 2014/0242582 | A1 | 8/2014 | Oliphant et al. |
| 2014/0274740 | A1 | 9/2014 | Srinivasan et al. |
| 2014/0336082 | A1 | 11/2014 | Park et al. |
| 2014/0357528 | A1 | 12/2014 | Robb et al. |
| 2015/0119257 | A1 | 4/2015 | Fodor et al. |
| 2015/0211070 | A1 | 7/2015 | Seligson et al. |
| 2015/0344977 | A1 | 12/2015 | Rolfe |
| 2016/0177359 | A1 | 6/2016 | Ukanis et al. |
| 2016/0251704 | A1 | 9/2016 | Talasaz et al. |
| 2016/0289737 | A1 | 10/2016 | Belyaev |
| 2016/0304953 | A1 | 10/2016 | Chen et al. |
| 2016/0326572 | A1 | 11/2016 | Schupp et al. |
| 2016/0326578 | A1 | 11/2016 | Bielas |
| 2017/0002397 | A1 | 1/2017 | Strauss et al. |
| 2017/0037469 | A1 | 2/2017 | Robins et al. |
| 2017/0145507 | A1 | 5/2017 | Koh et al. |
| 2017/0145508 | A1 | 5/2017 | Koh et al. |
| 2017/0145509 | A1 | 5/2017 | Koh et al. |
| 2017/0247689 | A1 | 8/2017 | Brown |
| 2018/0237851 | A1 | 8/2018 | Christians et al. |
| 2019/0024127 | A1 | 1/2019 | Yeh |
| 2019/0256891 | A1 | 8/2019 | Blauwkamp et al. |
| 2020/0291457 | A1 | 9/2020 | Blauwkamp et al. |
| 2021/0324467 | A1 | 10/2021 | Christians et al. |
| 2022/0010303 | A1 | 1/2022 | Bercovici et al. |
| 2022/0195496 | A1 | 6/2022 | Ahmed et al. |
| 2023/0212672 | A1 | 7/2023 | Shendure et al. |

FOREIGN PATENT DOCUMENTS

| | | | | |
|---|---|---|---|---|
| CN | 106103713 | A | 11/2016 | |
| EP | 1856295 | A2 | 11/2007 | |
| EP | 1885877 | A2 | 2/2008 | |
| EP | 2351857 | A1 | 8/2011 | |
| JP | 2015535431 | A | 12/2015 | |
| WO | WO-2011156795 | A2 | 12/2011 | |
| WO | WO-2012129363 | A2 | 9/2012 | |
| WO | WO-2012159023 | A2 | 11/2012 | |
| WO | WO-2012168815 | A2 | 12/2012 | |
| WO | WO-2013052907 | A2 | 4/2013 | |
| WO | WO-2013109981 | A1 | 7/2013 | |
| WO | WO-2013132305 | A1 | 9/2013 | |
| WO | WO-2013156627 | A1 | 10/2013 | |
| WO | WO-2013159035 | A2 | 10/2013 | |
| WO | WO-2013188846 | A1 | 12/2013 | |
| WO | WO-2014039556 | A1 | 3/2014 | |
| WO | WO-2014068075 | A1 | 5/2014 | |
| WO | WO-2014082032 | A1 | 5/2014 | |
| WO | WO-2014127484 | A1 | 8/2014 | |
| WO | WO-2014145078 | A1 | 9/2014 | |
| WO | WO-2014149134 | A2 | 9/2014 | |
| WO | WO-2014165596 | A1 | 10/2014 | |
| WO | WO-2015073080 | A1 | 5/2015 | |
| WO | WO-2015089333 | A1 | 6/2015 | |
| WO | WO-2015113725 | A1 | 8/2015 | |
| WO | WO-2015145133 | A1 | 10/2015 | |
| WO | WO-2016001736 | A1 | 1/2016 | |
| WO | WO-2016094947 | A1 | 6/2016 | |
| WO | WO-2017027835 | A1 | 2/2017 | |
| WO | WO-2017127741 | A1 | 7/2017 | |
| WO | WO-2017165864 | A1 | 9/2017 | |
| WO | WO-2018009723 | A1 | 1/2018 | |
| WO | WO-2018045359 | A1 | 3/2018 | |
| WO | WO-2018081130 | A1 | 5/2018 | |
| WO | WO-2018085862 | A2 * | 5/2018 | ........... C12Q 1/6886 |
| WO | WO-2018187521 | A2 | 10/2018 | |
| WO | WO-2018191563 | A1 | 10/2018 | |
| WO | WO-2018232598 | A1 | 12/2018 | |
| WO | WO-2019178157 | A1 | 9/2019 | |
| WO | WO-2020106893 | A1 | 5/2020 | |
| WO | WO-2020106987 | A1 | 5/2020 | |
| WO | WO-2022140302 | A1 | 6/2022 | |
| WO | WO-2022150725 | A1 | 7/2022 | |
| WO | WO-2022174117 | A1 | 8/2022 | |

OTHER PUBLICATIONS

Refseth et al. (Hybridization capture of microsatellites directly from genomic DNA, Electrophoresis, published 1997). (Year: 1997).*

Burnham et al. (Single-stranded DNA library preparation uncovers the origin and diversity of ultrashort cell-free DNA in plasma, Scientific Reports, published 2016) (Year: 2016).*

(56) References Cited

OTHER PUBLICATIONS

Abbott et al., Design and use of signature primers to detect carry-over of amplified material. J Virol Methods 46(1):51-59 (1994).
Davis, et al., A DNA-Based Biological Sample Tracking Method. Cell Preservation Technology 54-60 (2005).
EP19887248.3 Extended European Search Report dated Aug. 1, 2022.
EP19888226.8 Extended European Search Report dated Aug. 8, 2022.
European partial search report dated Apr. 21, 2023 for EP Application No. 22199875.0.
European search report and opinion dated Feb. 28, 2022 for EP Application No. 21187675.0.
Fan H.C., et al., "Noninvasive Diagnosis of Fetal Aneuploidy by Shotgun Sequencing DNA from Maternal Blood, "Proceedings of the National Academy of Sciences of the United States of America, vol. 105:16266-16271 (2008).
Han et al., Liquid biopsy for infectious diseases: a focus on microbial cell-free DNA sequencing. Theranostics 10(12): 5501-5513 (2020).
PCT/US2019/062488 International Preliminary Report on Patentability dated Jun. 3, 2021.
PCT/US2019/062665 International Preliminary Report on Patentability dated Apr. 28, 2020.
U.S. Appl. No. 17/355,882 Office Action dated Apr. 6, 2023.
U.S. Appl. No. 17/355,882 Office Action dated Mar. 6, 2023.
U.S. Appl. No. 17/355,882 Office Action dated Mar. 30, 2023.
U.S. Appl. No. 17/355,882 Office Action dated May 4, 2023.
Wu et al., Facile single-stranded DNA sequencing of human plasma DNA via thermostable group II intron reverse transcriptase template switching. Nature Scientific Reports 7:8421 (2017).
Abril, et al. Diagnosis of Capnocytophaga canimorsus Sepsis by Whole-Genome Next-Generation Sequencing. Open Forum Infect Dis. Sep. 2016; 3(3): ofw144. Published online Jul. 12, 2016. DOI:10.1093/ofid/ofw144.
Blauwkamp, et al. Analytical and clinical validation of a microbial cell-free DNA sequencing test for infectious disease. Nat Microbiol. Apr. 2019;4(4):663-674. doi: 10.1038/s41564-018- 0349-6. Epub Feb. 11, 2019.
Burnham, et al. Single-stranded DNA library preparation uncovers the origin and diversity of ultrashort cell-free DNA in plasma. Sci Rep. Jun. 14, 2016;6:27859. doi: 10.1038/srep27859.
Chen, et al. Helicobacter pylori colonization is inversely associated with childhood asthma. J Infect Dis. Aug. 15, 2008; 198(4): 553-560.doi: 10.1086/590158.
Chen, et al. The overlooked fact: fundamental need of spike-in controls for virtually all genome-wide analyses. Manuscript posted online Dec. 28, 2015. Mol. Cell. Biol. American Society for Microbiology, doi:10.1128/MCB.00970-14. 20 pages.
Chey, et al. American College of Gastroenterology guideline on the management of Helicobacter pylori infection. Am J Gastroenterol. Aug. 2007; 102(8): 1808-1825. doi: 10.1111/j.1572-0241.2007.01393.x. Epub Jun. 29, 2007.
Deveson, et al. Representing genetic variation with synthetic DNA standards. Nature Methods. Volume: 13, pp. 784-791. Received Mar. 23, 2016. Accepted Jun. 28, 2016. Published online Aug. 8, 2016. DOI:doi:10.1038/nmeth.3957.
Dixon, et al. Histological classification of gastritis and Helicobacter pylori infection: an agreement at last? The International Workshop on the Histopathology of Gastritis. Helicobacter. Jul. 1997;2 Suppl 1:S17-24. doi: 10.1111/j.1523-5378.1997.06b09.x.
Epigene, 5-methylcytosine (5mC), available at https://epigenie.com/key-epigenetic-players/important-dna-methylation-factors/5-v methylcytosine-5mc/, accessed Feb. 10, 2020.
European search report and opinion dated Aug. 29, 2019 for EP Application No. 17771302.1.
Fan, et al. Noninvasive diagnosis of fetal aneuploidy by shotgun sequencing DNA from maternal blood. Proc Natl Acad Sci U S A. Oct. 21, 2008; 105(42):16266-71. Epub Oct. 6, 2008.
Fu, et al. Molecular indexing enables quantitative targeted RNA sequencing and reveals poor efficiencies in standard library preparations. Proc Natl Acad Sci U S A. Feb. 4, 2014;111(5):1891-6.
Gansauge, et al. Single-stranded DNA library preparation for the sequencing of ancient or damaged DNA. Nat Protoc. Apr. 2013;8(4):737-48. doi: 10.1038/nprot.2013.038. Epub Mar. 14, 2013.
Gansauge et al. Single-stranded DNA library preparation from highly degraded DNA using T4 DNA ligase. Nucleic Acids Research, vol. 45, No. 10, e79, 10 pages (2017). Published online Jan. 24, 2017.
GenBank Accession No. GCA_000001405.27 (replaced). RefSeq Accession: GCF_000001405.38 (replaced). GRCh38.p12. Date: Dec. 21, 2017. 3 pages. Retrieved Feb. 10, 2021 at URL: https://www.ncbi.nlm.nih.gov/assembly/GCF_000001405.38/.
Genelink, Degenerate Bases & Spiking—Introduction, available at http://www.genelink.com/oligo_modifications_reference/OMR_mod_category_intro.asp?mod_sp _cat_id=5, accessed Feb. 10, 2020.
Heger, Monica. Garvan Team Uses Synthetic DNA to Create Spike-In Method for NGS Assay Validation. Genomeweb. Aug. 8, 2016. 4 pages.
Highlander, Sarah K. High throughput sequencing methods for microbiome profiling: application to food animal systems. Anim Health Res Rev. Jun. 2012; 13(1):40-53. doi: 10.1017/S1466252312000126.
IDT. Integrated DNA Technologies, Inc. Modifications. Accessed Oct. 12, 2021. 1 page. Available online at https://www.idtdna.com/site/Catalog/Modifications.
International search report with written opinion dated Mar. 10, 2020 for PCT/US2019/062488.
International search report with written opinion dated Apr. 28, 2020 for PCT/US2019/062665.
International search report with written opinion dated Jul. 26, 2017 for PCT/US2017/024176.
Islam, et al. Quantitative single-cell RNA-seq with unique molecular identifiers. Nat Methods. Feb. 2014;11(2):163-6.
Jiang, et al. Synthetic spike-in standards for RNA-seq experiments. Genome Res. Sep. 2011;21(9):1543-51. doi: 10.1101/gr.121095.111. Epub Aug. 4, 2011.
Kim et al., Characterizing noise structure in single-cell RNA-seq distinguishes genuine from technical stochastic allelic expression, Nat Commun. Oct. 22, 2015; 6: 8687.
Koh, W. et al., Noninvasive in vivo monitoring of tissue-specific global gene expression in humans, PNAS 111(20):7361-7366 (Jul. 29, 2014).
Kuipers, et al. The prevalence of Helicobacter pylori in peptic ulcer disease. Aliment Pharmacol Ther. 1995;9 Suppl 2:59-69.
Life Technologies Corporation. Ambion® ERCC RNA Spike-In Control Mixes. User Guide pp. 1-26 (2012) Accessed online at https://www.thermofisher.com/document-connect/document-connect.html?url=https%3A%2F%2Fassets.thermofisher.com%2FTFS-Assets%2FLSG%2Fmanuals%2Fcms_086340.pdftitle=VXNIciBHdWlkZTogRVJDQyBSTkEgU3Bpa2UtSW4gQ29udHJvbCBNaXhlcyAoRW5%20nbGIzaCAp.
Lindner, et al. Metagenomic abundance estimation and diagnostic testing on species level. Nucleic Acids Res. Jan. 7, 2013;41(1):e10. doi: 10.1093/nar/gks803. Epub Aug. 31, 2012.
Locati, et al. Improving small RNA-seq by using a synthetic spike-in set for size-range quality control together with a set for data normalization. Nucleic Acids Res. Aug. 18, 2015;43(14):e89. doi: 10.1093/nar/gkv303. Epub Apr. 13, 2015.
Matranga, et al. Enhanced methods for unbiased deep sequencing of Lassa and Ebola RNA viruses from clinical and biological samples. Genome Biol. 2014;15(11):519.
Merriam-Webster, definition of "or," available at https://www.merriam-webster.com/dictionary/or, accessed May 18, 2020.
Notice of Allowance dated Feb. 26, 2018 for U.S. Appl. No. 15/469,474.
Notice of Allowance dated Mar. 8, 2018 for U.S. Appl. No. 15/469,474.
Notice of Allowance dated Apr. 6, 2021 for U.S. Appl. No. 15/953,822.
Notice of Allowance dated May 5, 2021 for U.S. Appl. No. 15/953,822.

(56) References Cited

OTHER PUBLICATIONS

Notice of Allowance dated Jul. 9, 2021 for U.S. Appl. No. 15/953,822.
Office action dated Feb. 13, 2020 for U.S. Appl. No. 15/953,822.
Office action dated May 21, 2020 for U.S. Appl. No. 15/953,822.
Office action dated Oct. 26, 2017 for U.S. Appl. No. 15/469,474.
Office action dated Dec. 14, 2020 for U.S. Appl. No. 15/953,822.
Quail, et al. SASI-Seq: sample assurance Spike-Ins, and highly differentiating 384 barcoding for Illumina sequencing. BMC Genomics. Feb. 7, 2014;15:110. doi: 10.1186/1471-2164-15-110.
Risso, D., et al., Normalization of RNA-seq data using factor analysis of control genes or samples. Nat Biotechnol. Sep. 2014;32(9):896-902. doi: 10.1038/nbt.2931. Epub Aug. 24, 2014.
Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.
Stegle, O., Computational and analytical challenges in single-cell transcriptomics. Nat Rev Genet. Mar. 2015;16(3):133-45. doi: 10.1038/nrg3833. Epub Jan. 28, 2015.
Sung, et al. Systematic review: the global incidence and prevalence of peptic ulcer disease. Aliment Pharmacol Ther. May 1, 2009;29(9):938-946. doi: 10.1111/j.1365-2036.2009.03960.x.
Tong, et al. Evaluating the impact of sequencing error correction for RNA-seq data with ERCC RNA spike-in controls. IEEE EMBS Int Conf Biomed Health Inform. Feb. 2016;2016:74-77. doi: 10.1109/BHI.2016.7455838.
Xia, et al. Accurate genome relative abundance estimation based on shotgun metagenomic reads. PLoS One. 2011;6(12):e27992. doi: 10.1371/journal.pone.0027992. Epub Dec. 6, 2011.
Yu, et al. Normalization of human RNA-seq experiments using chimpanzee RNA as a spike-in standard. Sci Rep. Aug. 24, 2016;6:31923. doi: 10.1038/srep31923.
Zhu, et al. Reverse transcriptase template switching: a SMART approach for full-length cDNA library construction. Biotechniques. Apr. 2001;30(4):892-7.
Zook, et al. Synthetic spike-in standards improve run-specific systematic error analysis for DNA and RNA sequencing. PLoS One. 2012;7(7):e41356.
Arbabi et al. (2016) "Cell-free DNA fragment-size distribution analysis for non-invasive prenatal CNV prediction" 32;11, pp. 1662-1669.
Beck, et al. Profile of the circulating DNA in apparently healthy individuals. Clin Chem. Apr. 2009;55(4):730-8. doi: 10.1373/clinchem.2008.113597. Epub Jan. 30, 2009.
Burnham et al.: Urinary cell-free DNA is a versatile analyte for monitoring infections of the urinary tract. Nat Commun 9: 2412 (10 pgs) 2018.
Giacona, Mary Beth et al. Cell-free DNA in Human Blood Plasma: Length Measurements in Patients with Pancreatic Cancer and Healthy Controls. Pancreas 17(1):89-97 (1998).

* cited by examiner

Clinical Sample

↓

Spiked Sample

↓

Extraction

↓

Library Synthesis

↓

Enrichment

↓

Sequencing

↓

Calculate a measurement using selected reads

↓

Compare the measurement to a control or reference value

↓

Determine the infection stage

Clinical Sample

↓

Spiked Sample

↓

Extraction

↓

Library Synthesis

↓

Enrichment

↓

RNA Sequencing

↓

Calculate a measurement using selected reads

↓

Compare the measurement to a control or reference value

↓

Determine the infection site

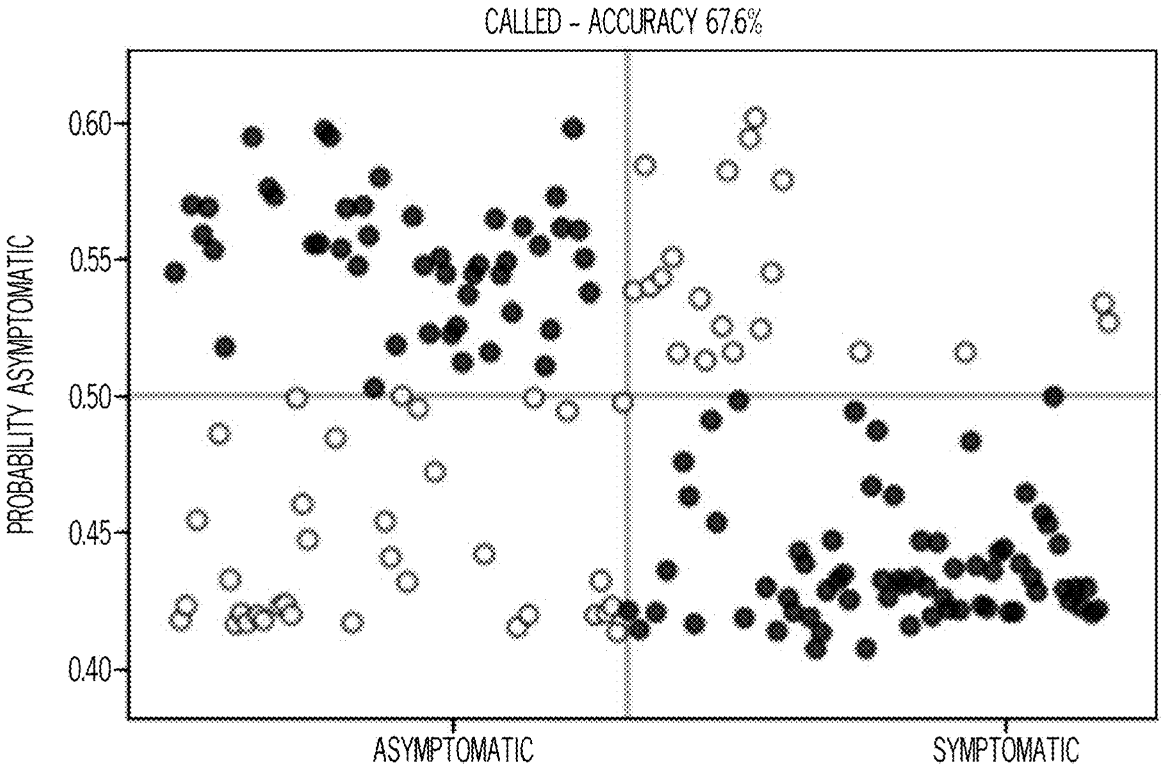
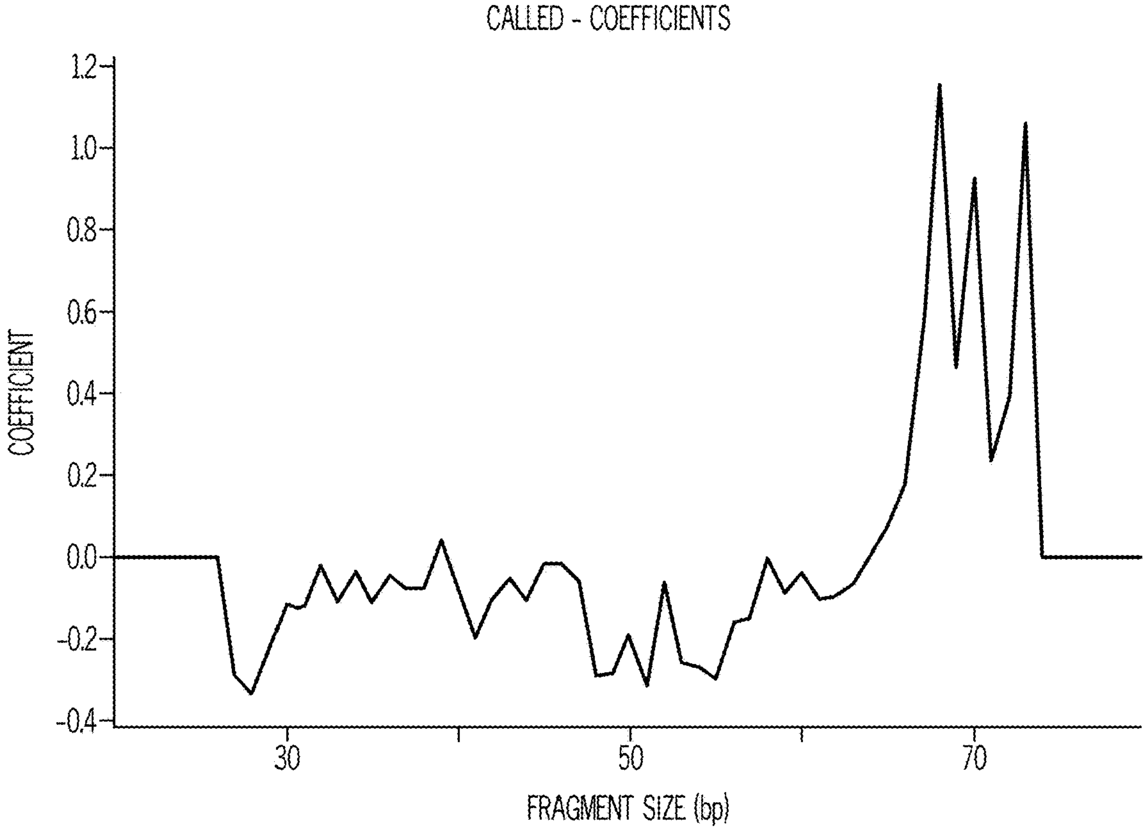
FIG. 16D

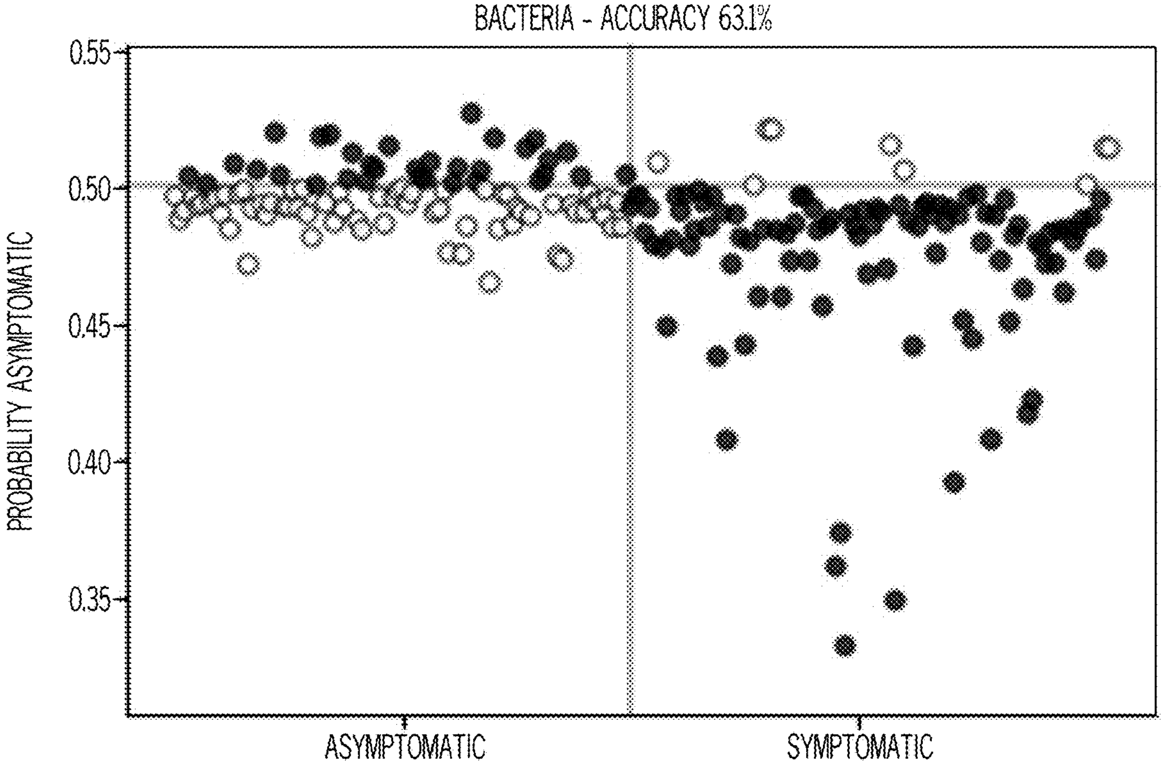
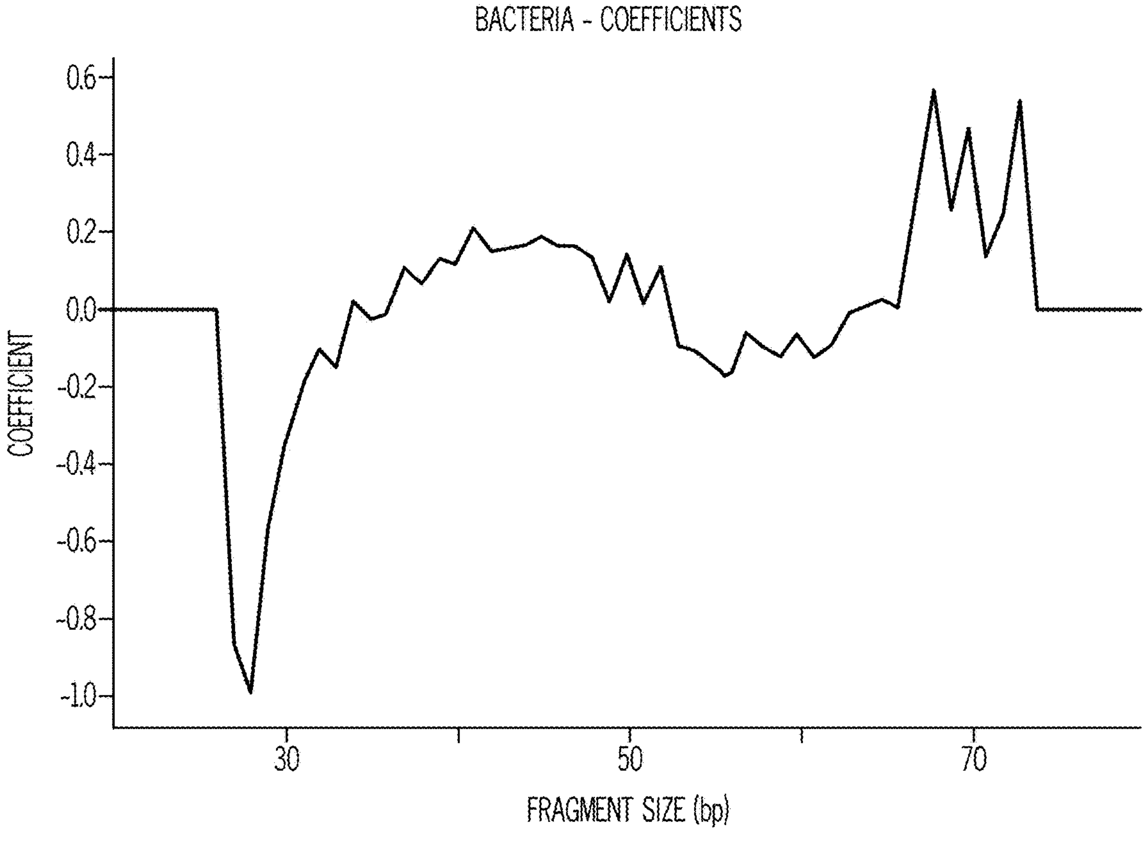
FIG. 16E

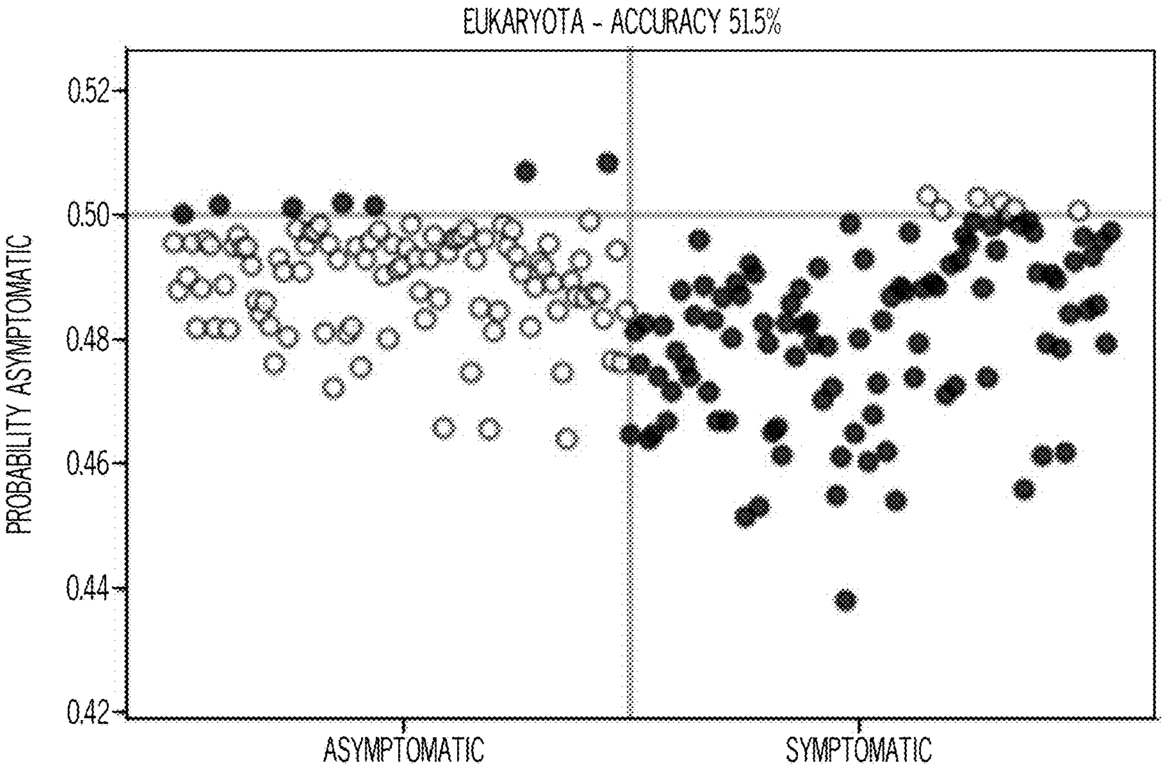
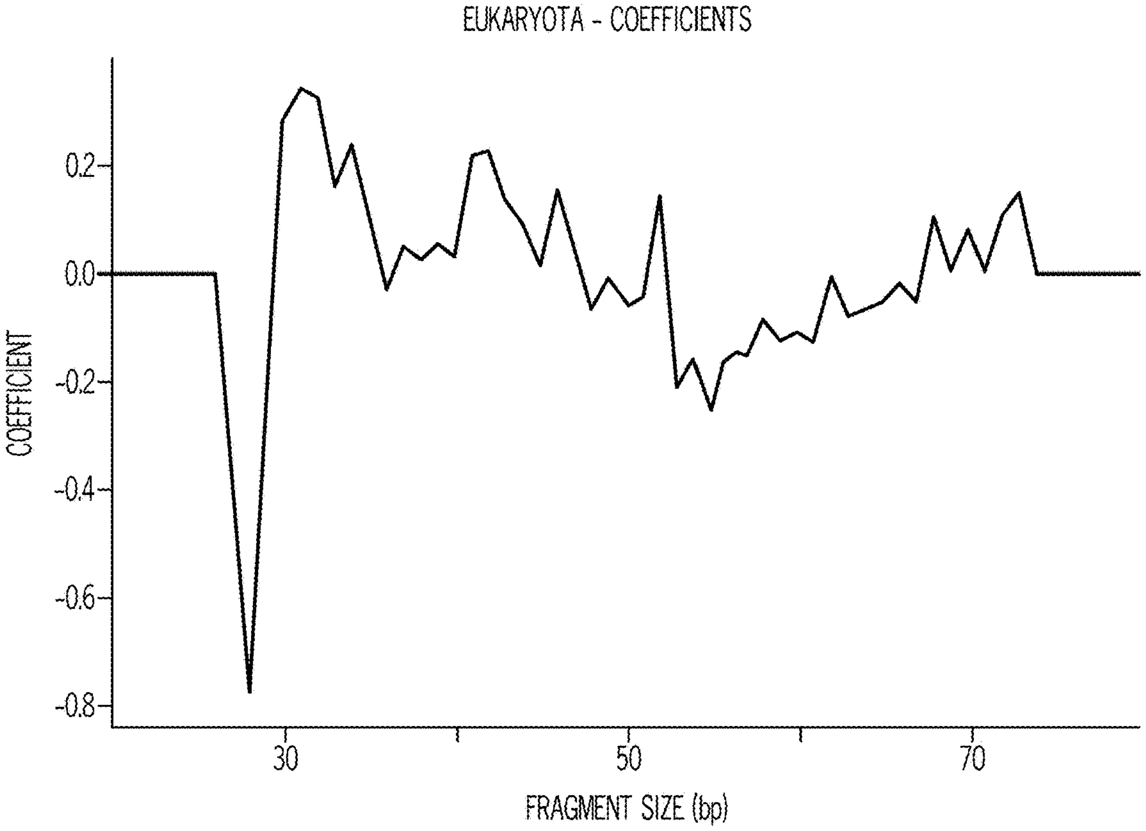
FIG. 16F

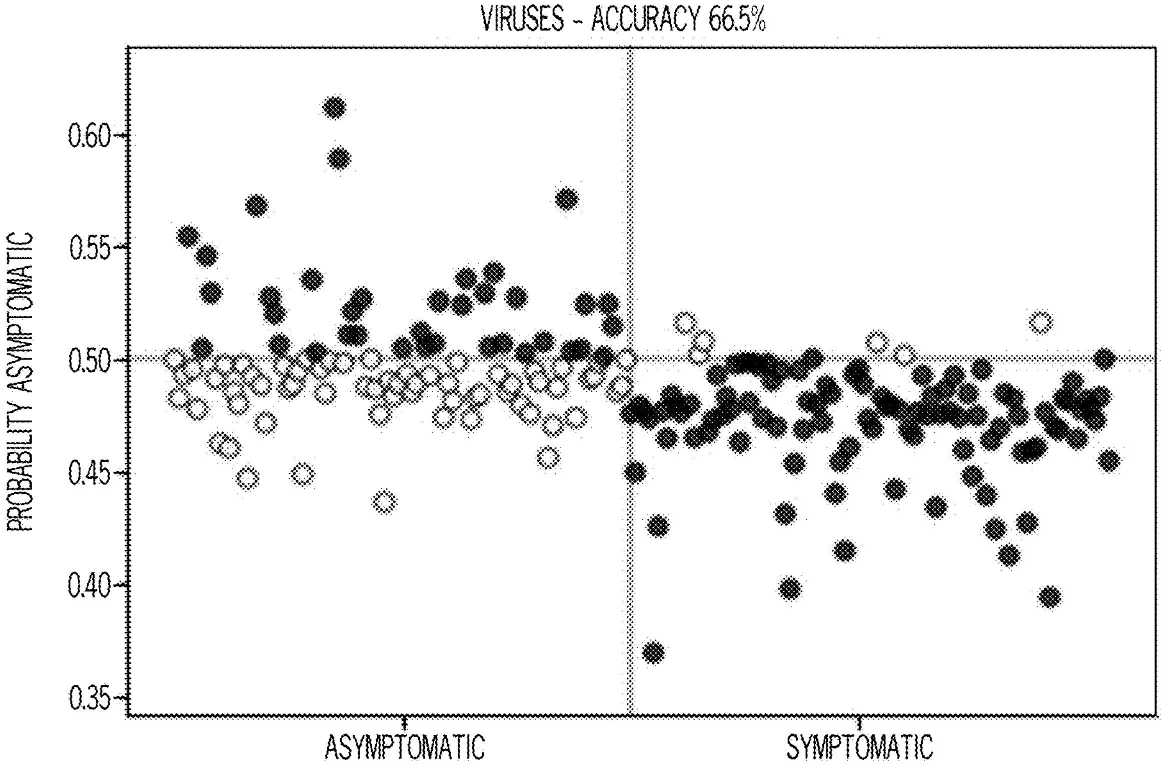
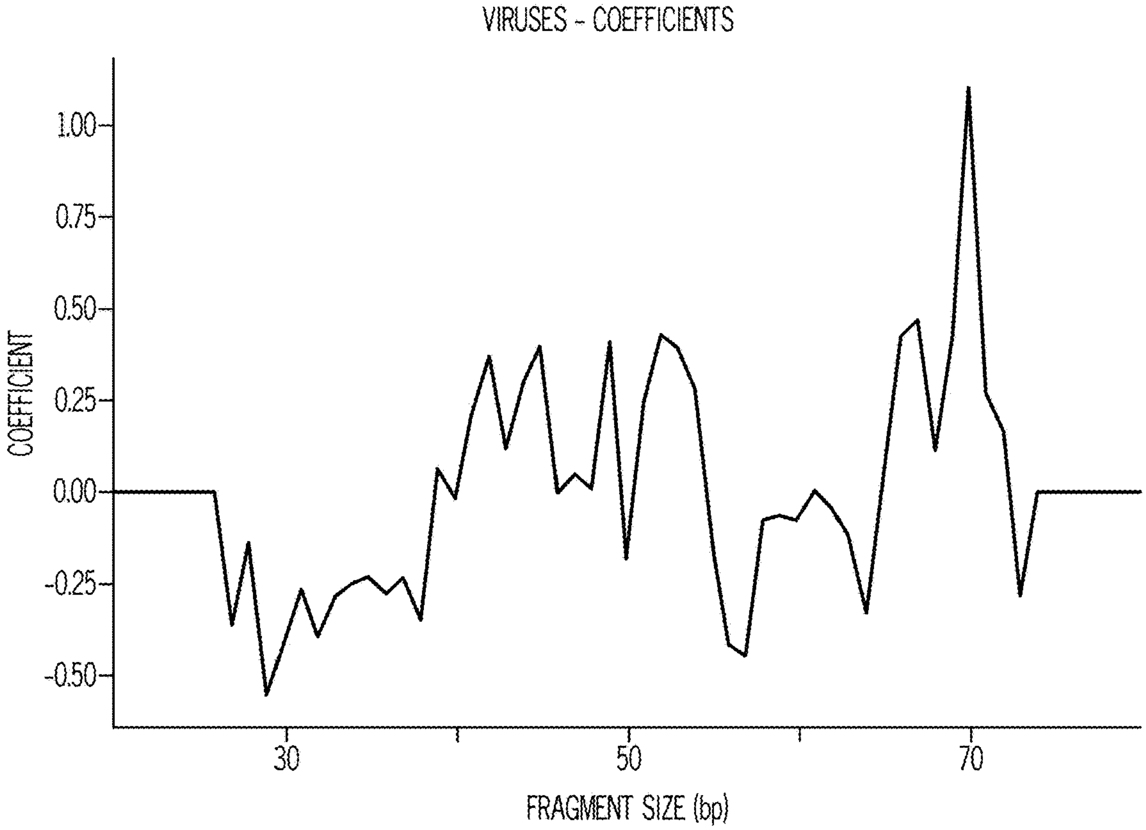
FIG. 16G

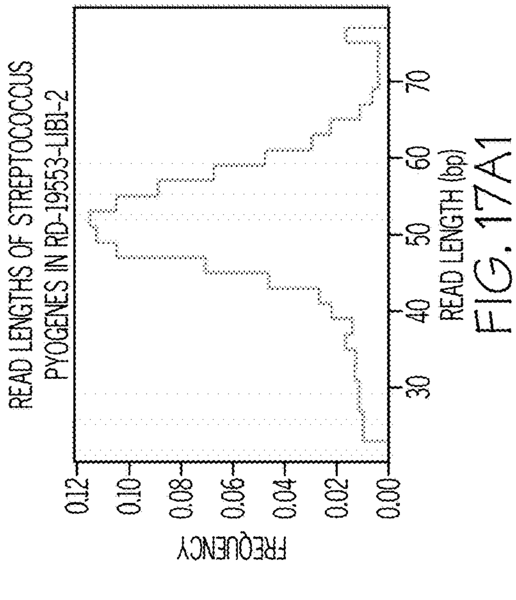
FIG. 17A1
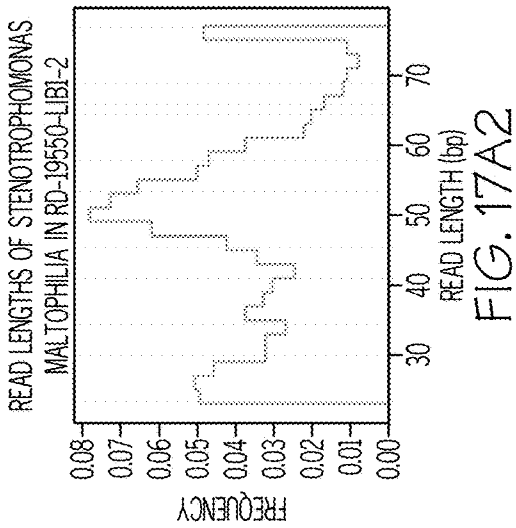
FIG. 17A2
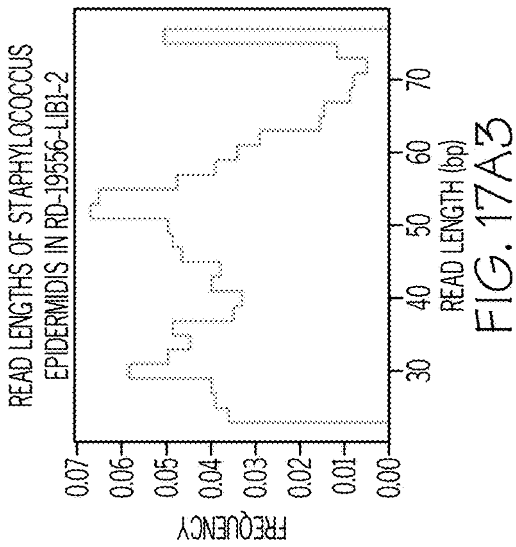
FIG. 17A3
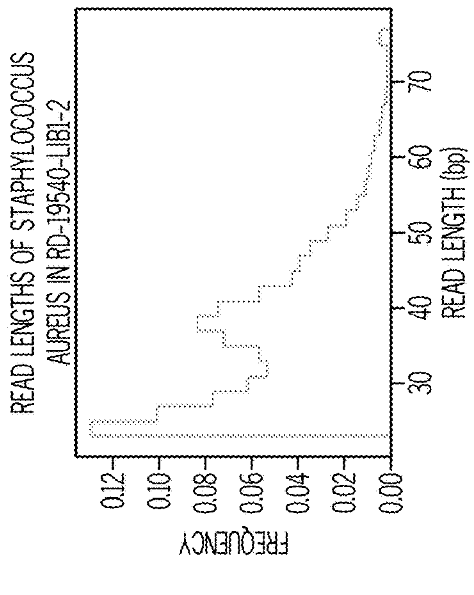
FIG. 17A4
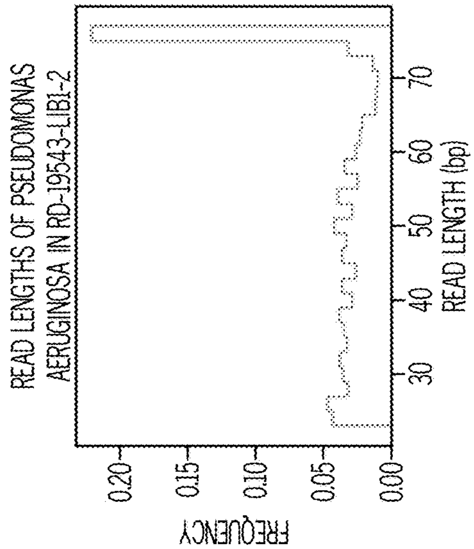
FIG. 17A5
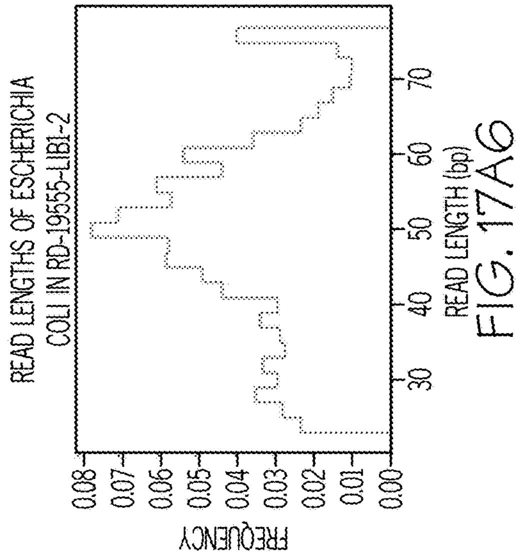
FIG. 17A6

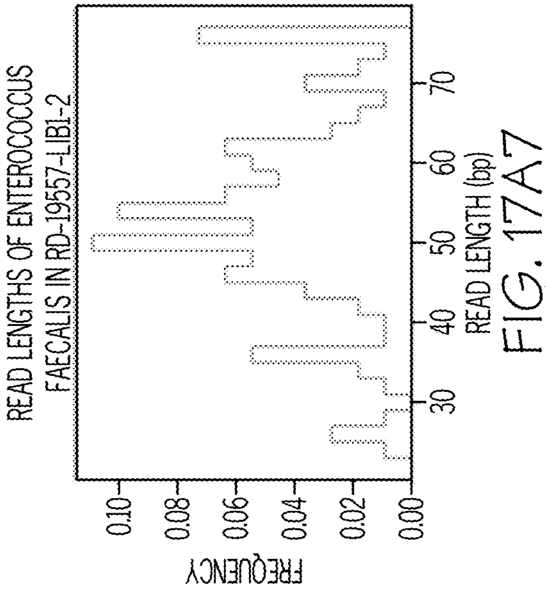
FIG. 17A7
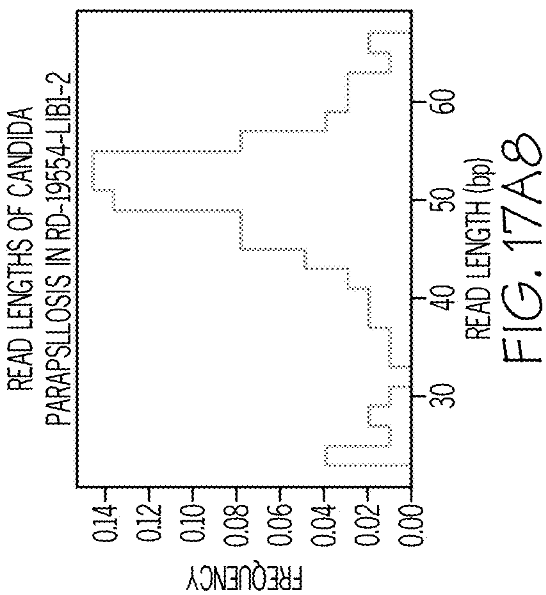
FIG. 17A8
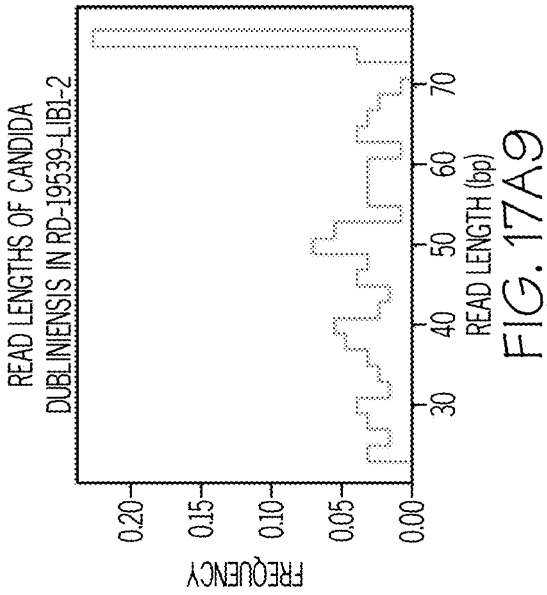
FIG. 17A9
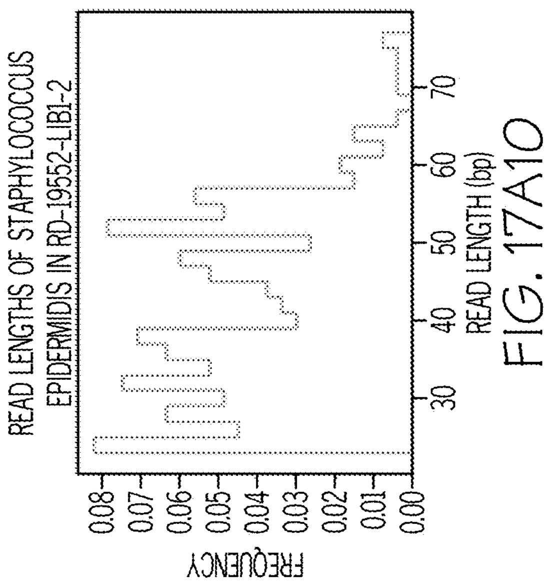
FIG. 17A10

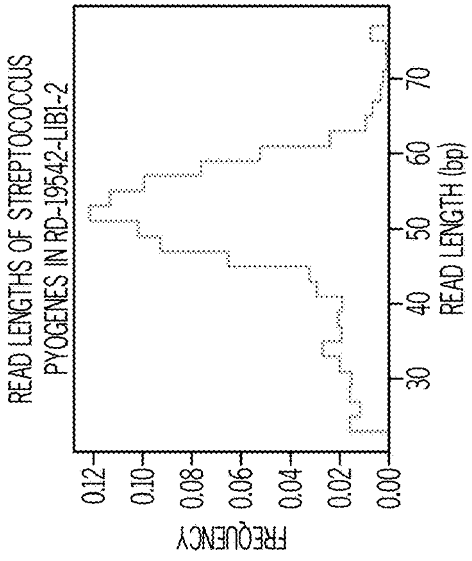
FIG. 17B1
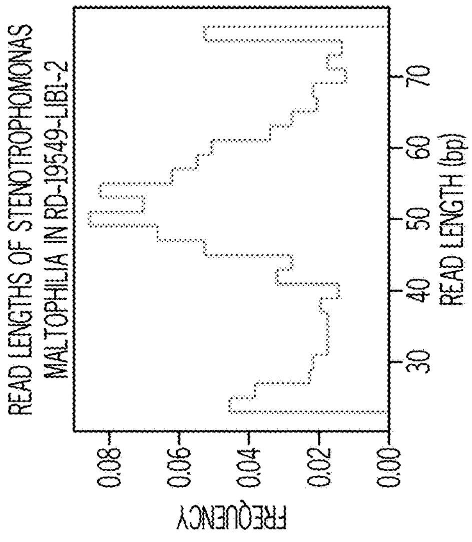
FIG. 17B2
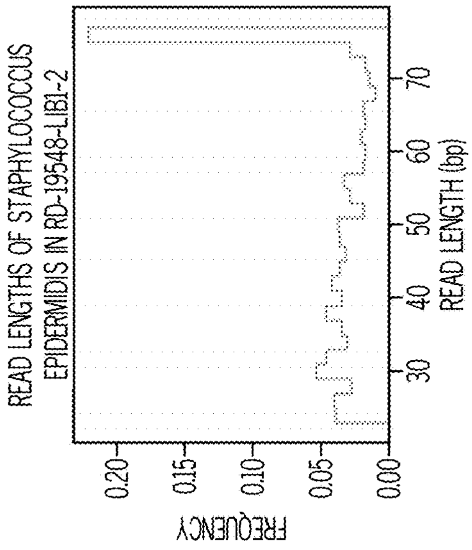
FIG. 17B3
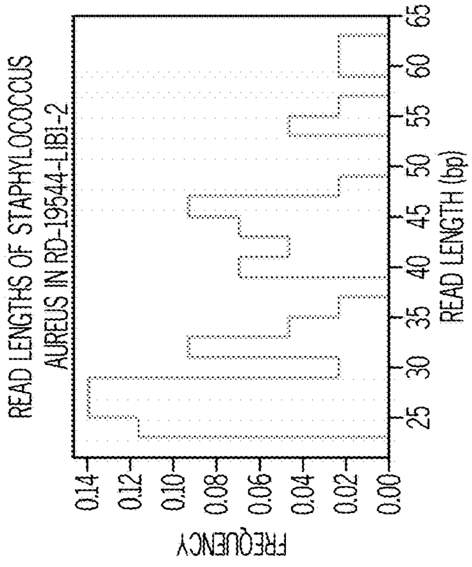
FIG. 17B4
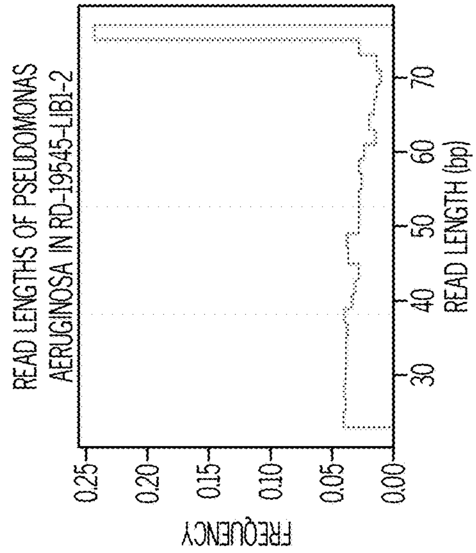
FIG. 17B5
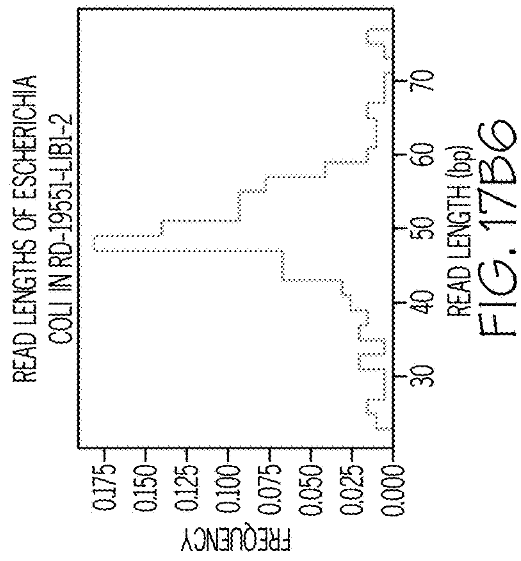
FIG. 17B6

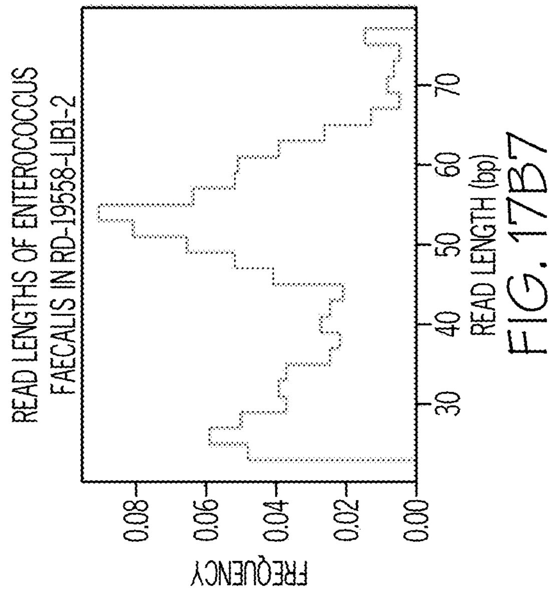
FIG. 17B7
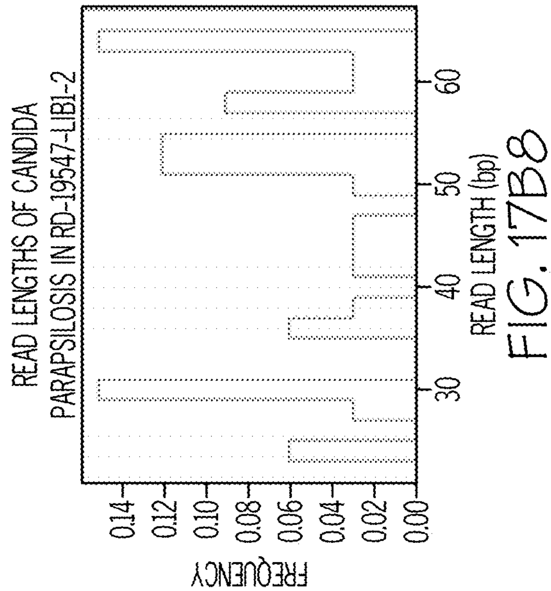
FIG. 17B8
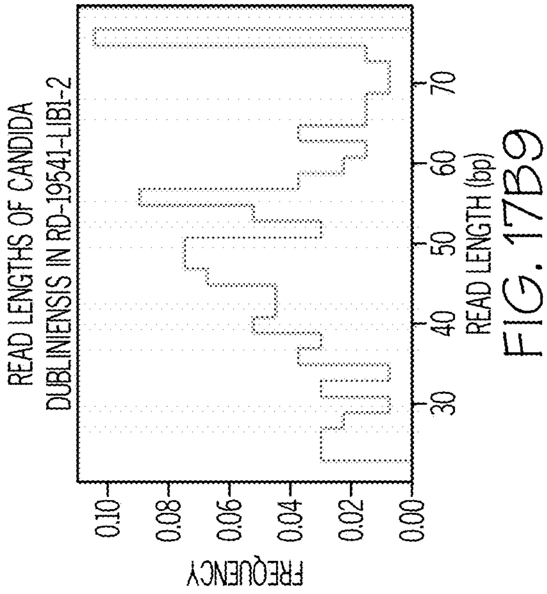
FIG. 17B9
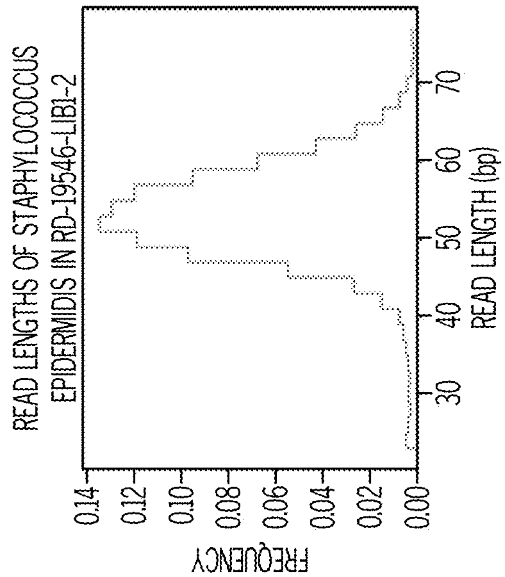
FIG. 17B10

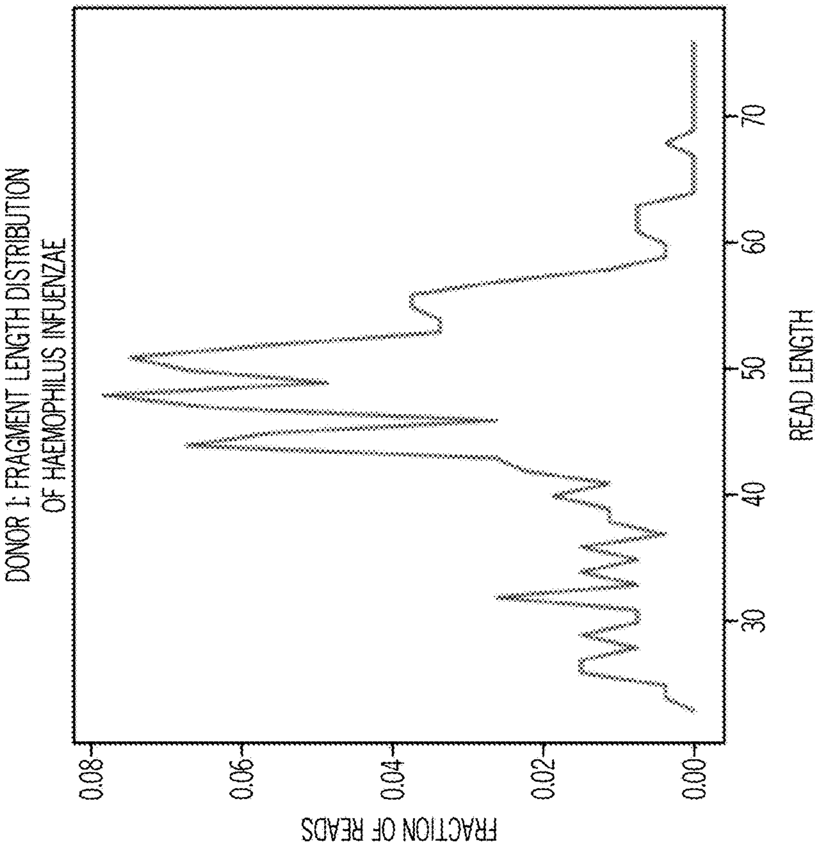
FIG. 18A1
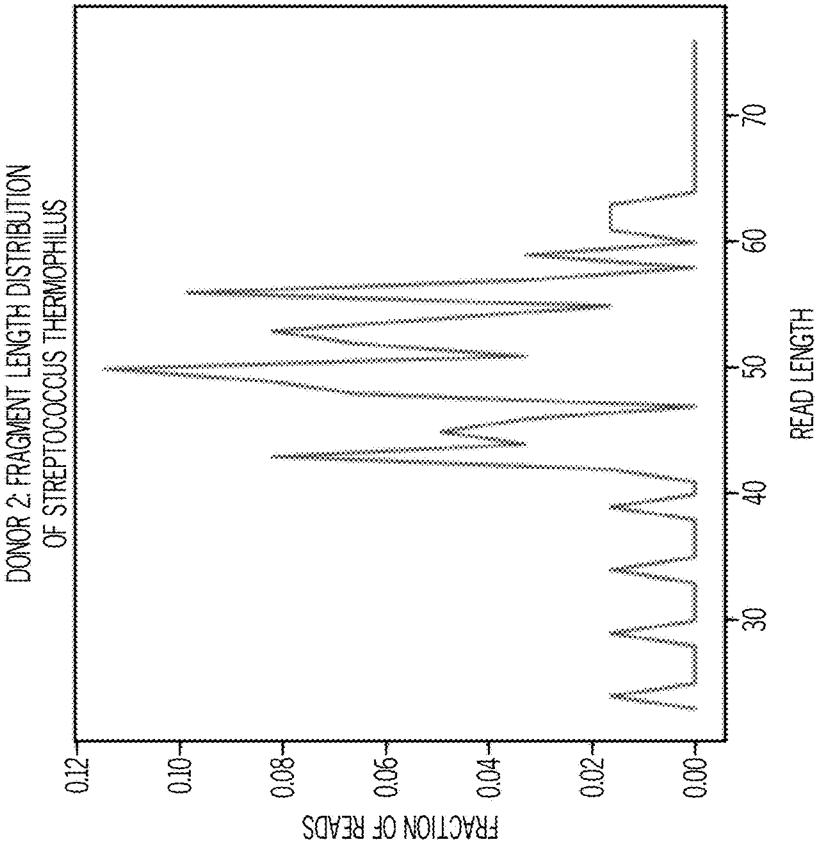
FIG. 18A2

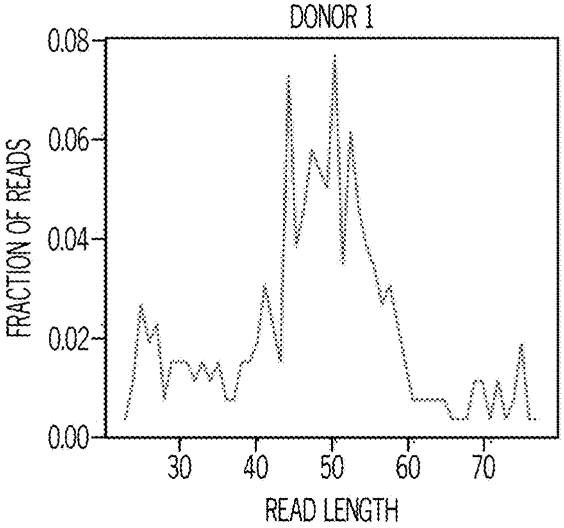
FIG. 18B1
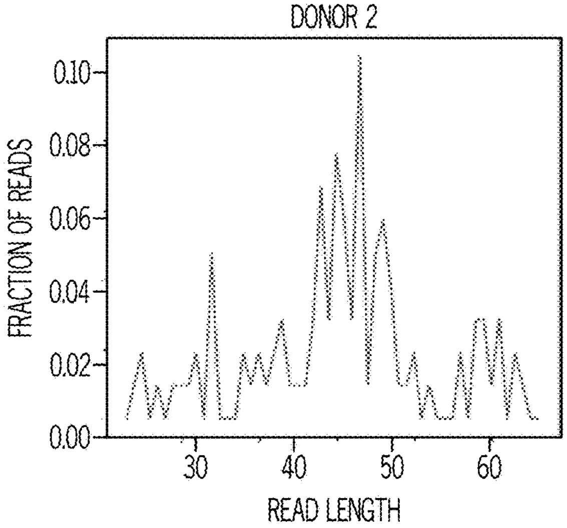
FIG. 18B2
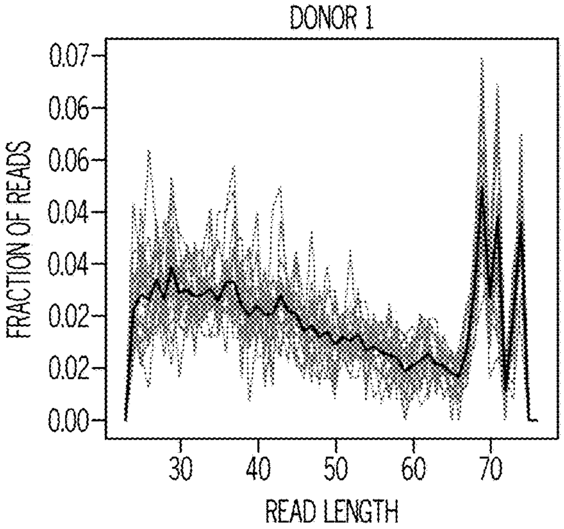
FIG. 18B3
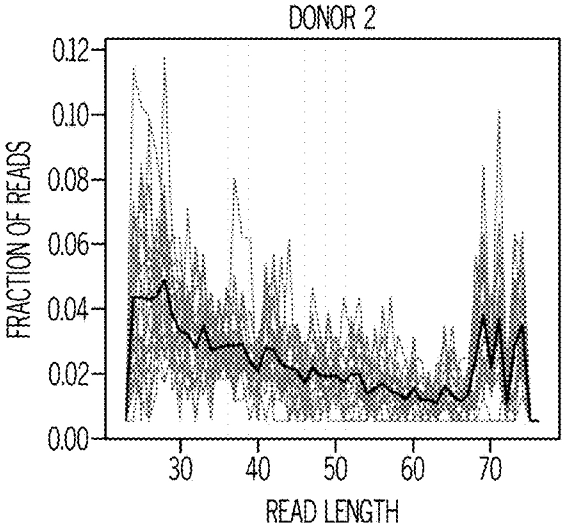
FIG. 18B4

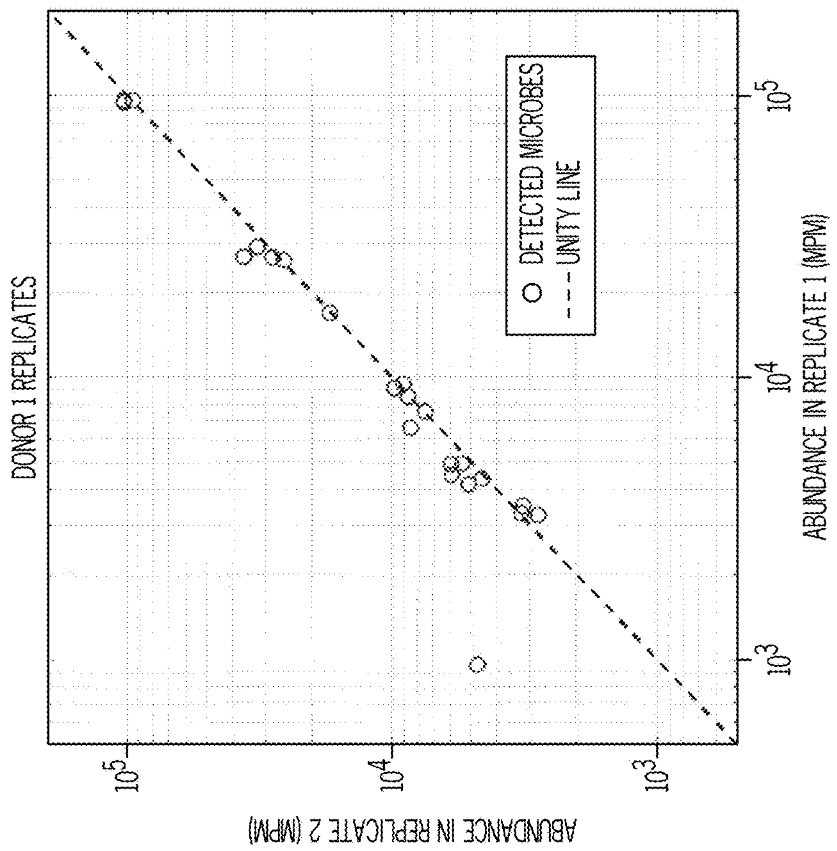
FIG. 18C1
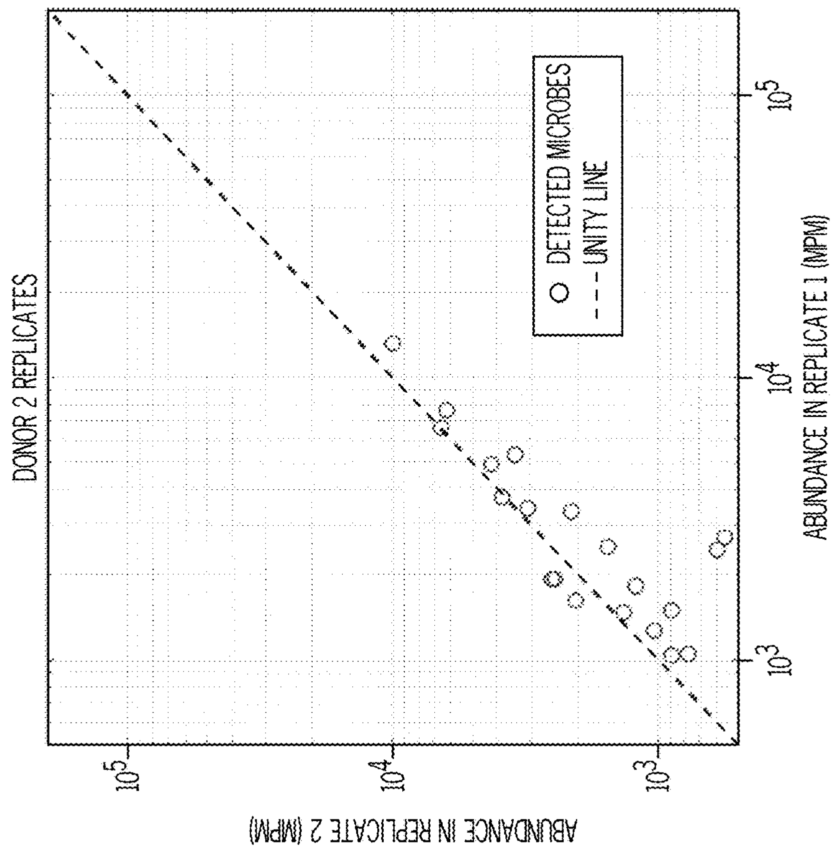
FIG. 18C2

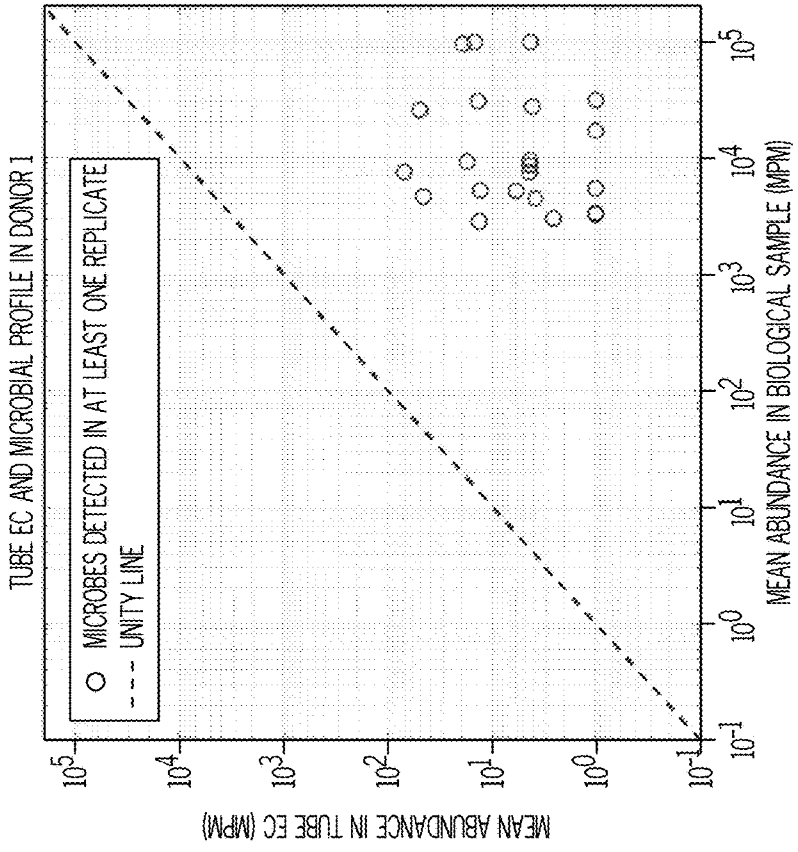
FIG. 18D1
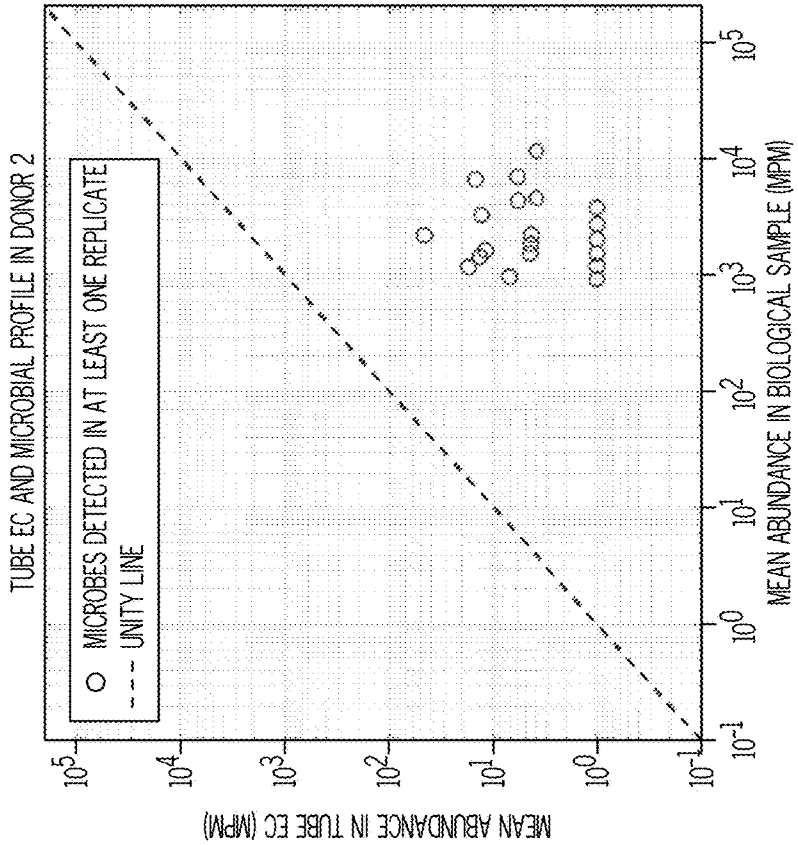
FIG. 18D2

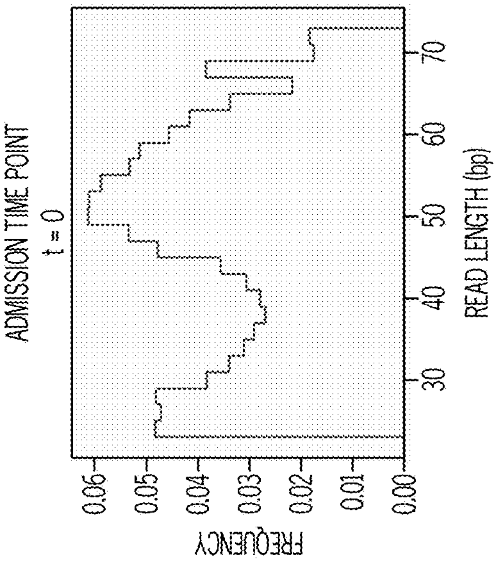
FIG. 19A1
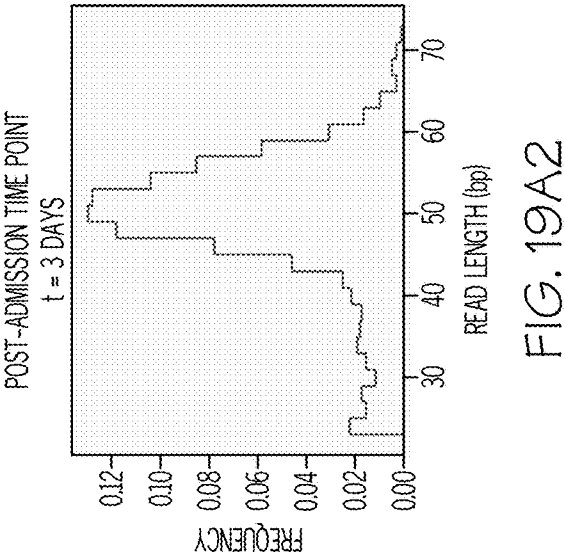
FIG. 19A2
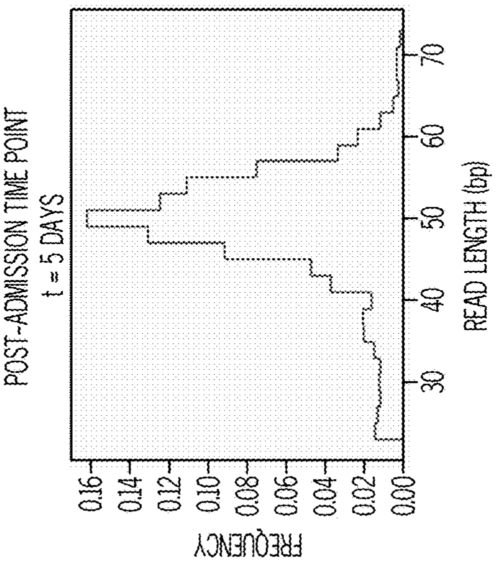
FIG. 19A3

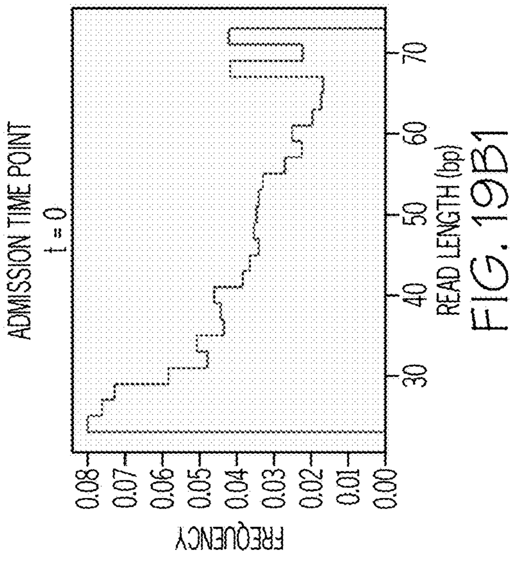
FIG. 19B1
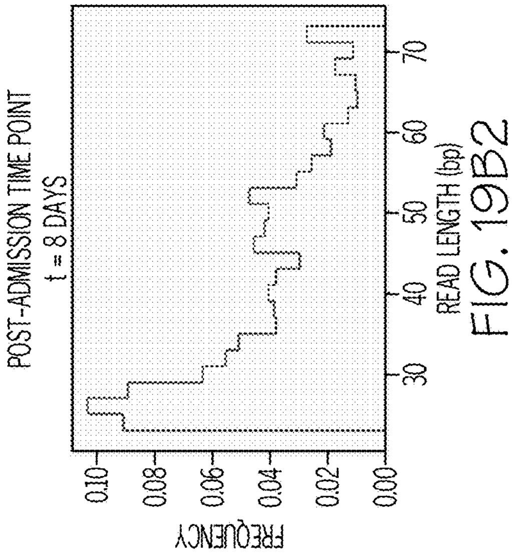
FIG. 19B2
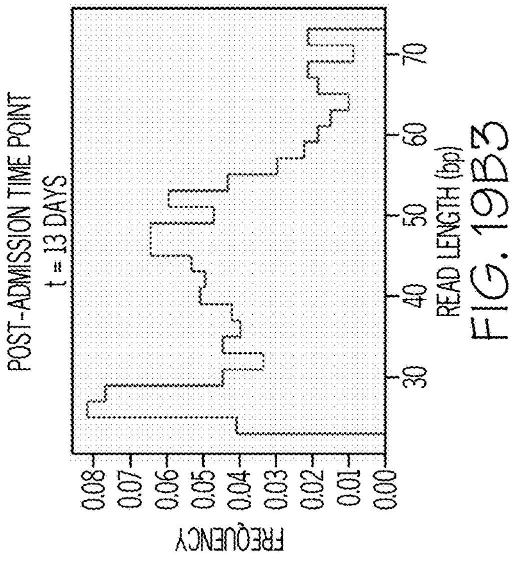
FIG. 19B3
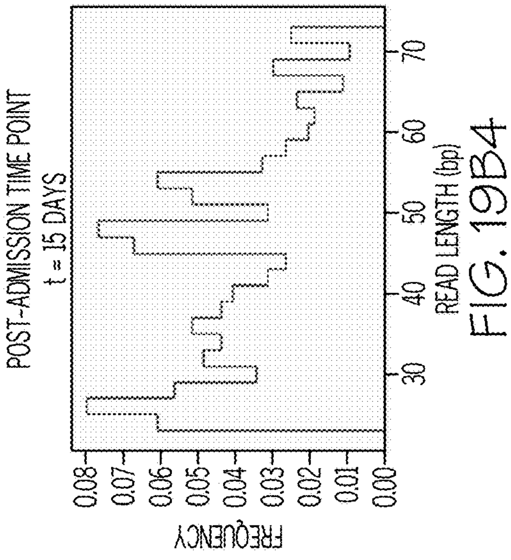
FIG. 19B4
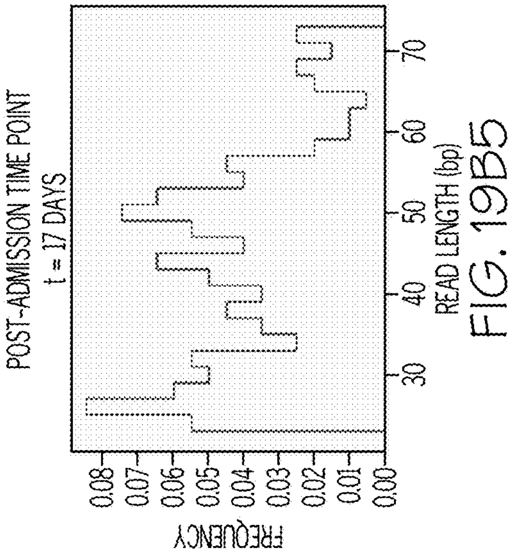
FIG. 19B5

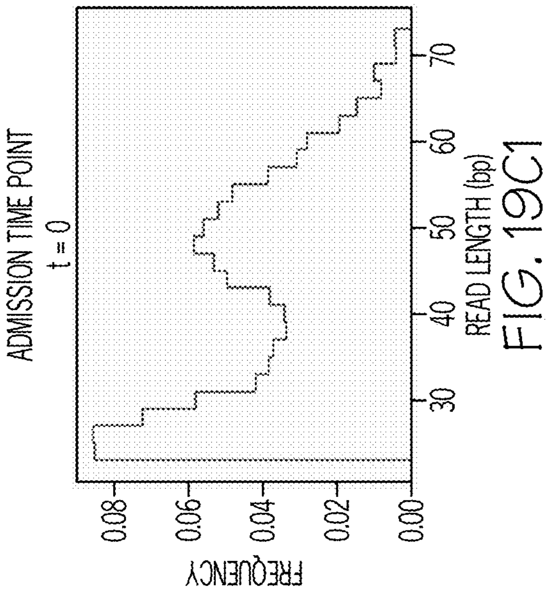
FIG. 19C1
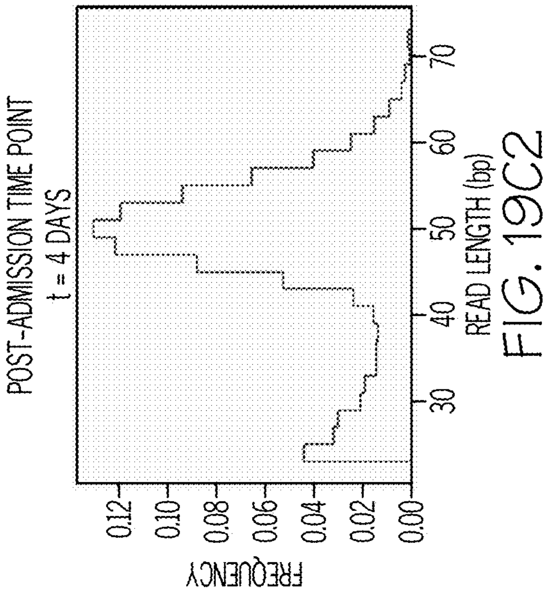
FIG. 19C2
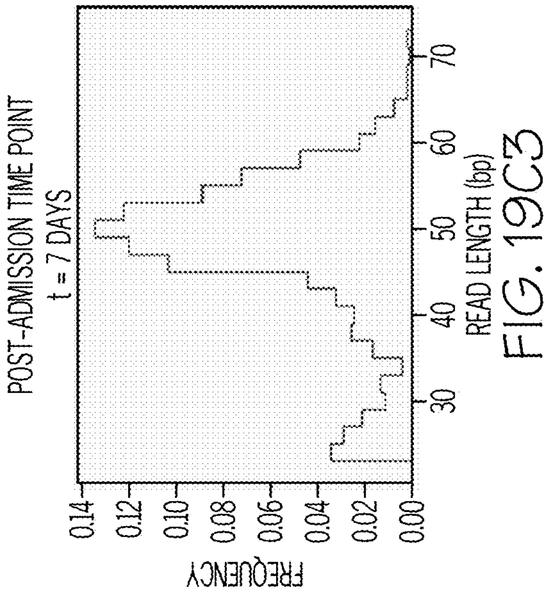
FIG. 19C3
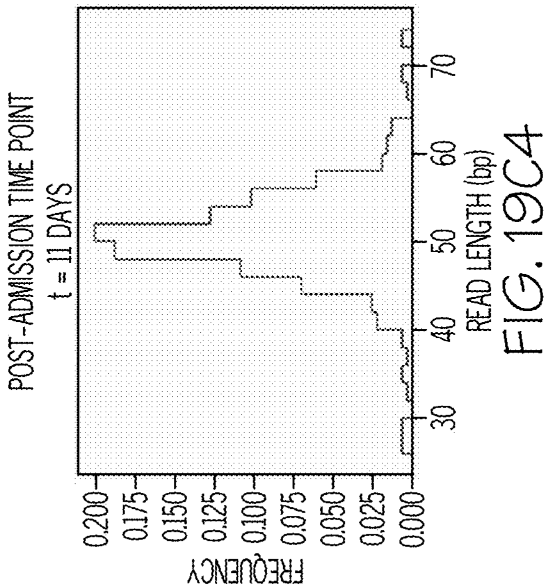
FIG. 19C4

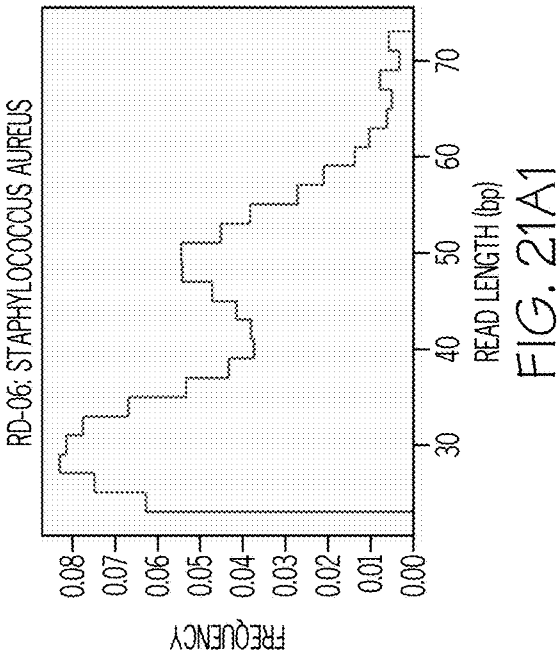
FIG. 21A1
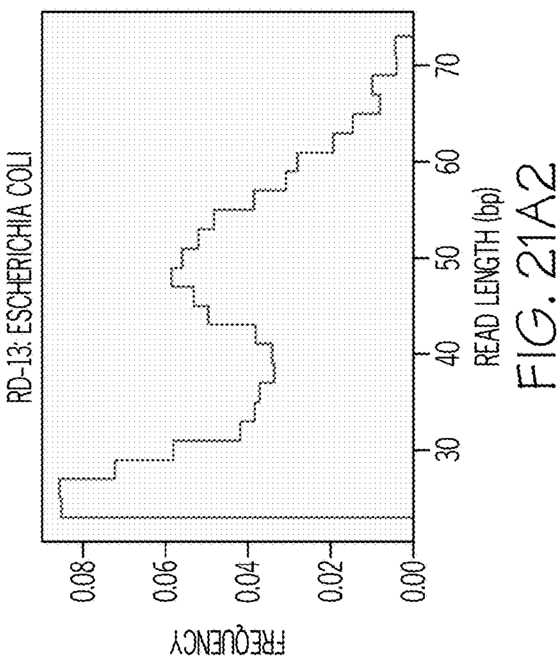
FIG. 21A2
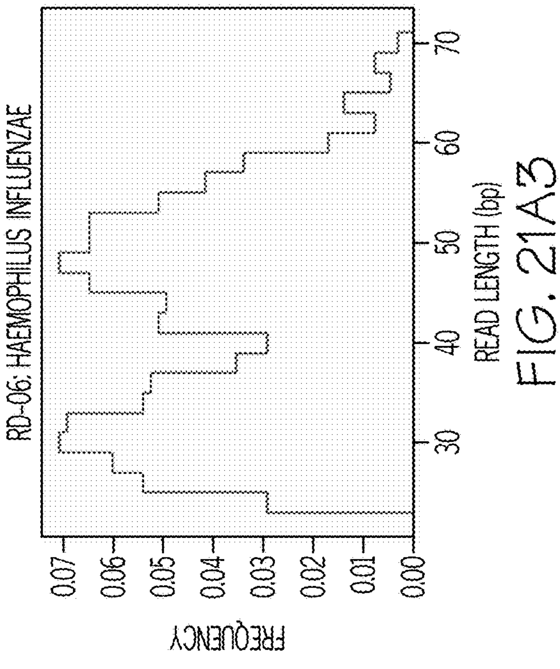
FIG. 21A3
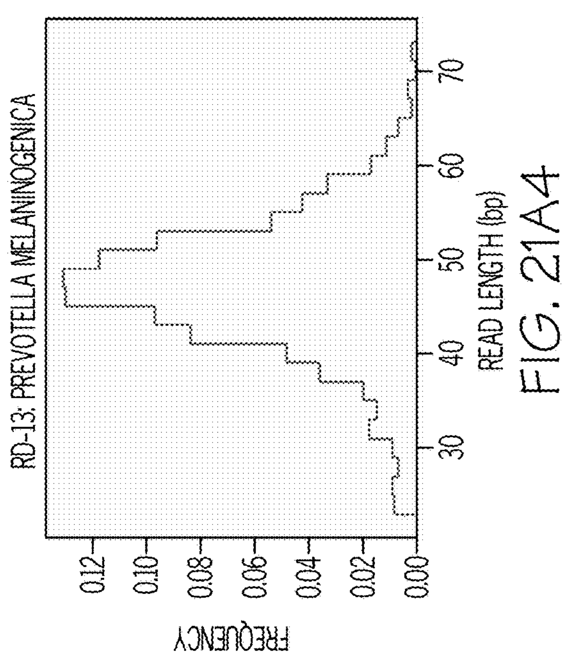
FIG. 21A4

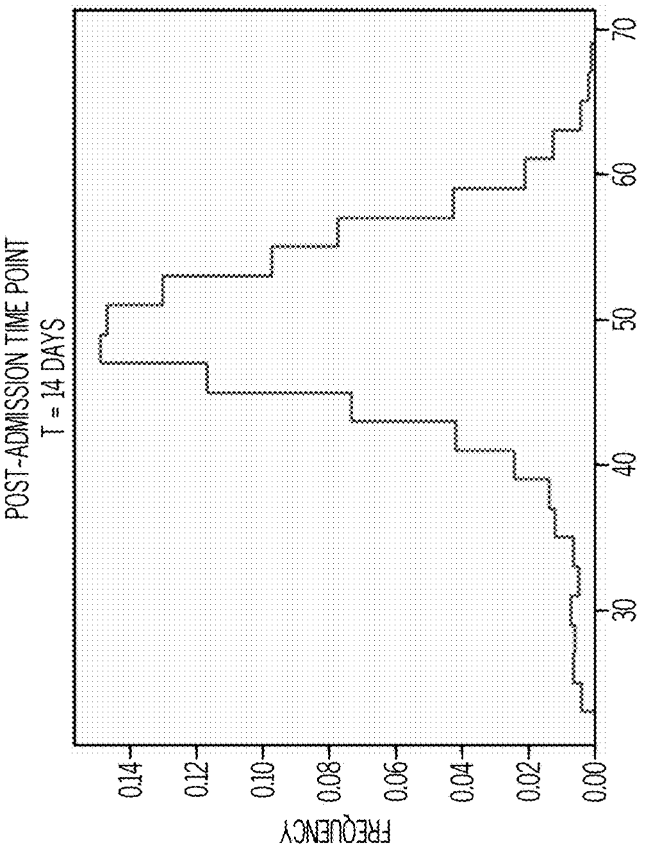
FIG. 21B2
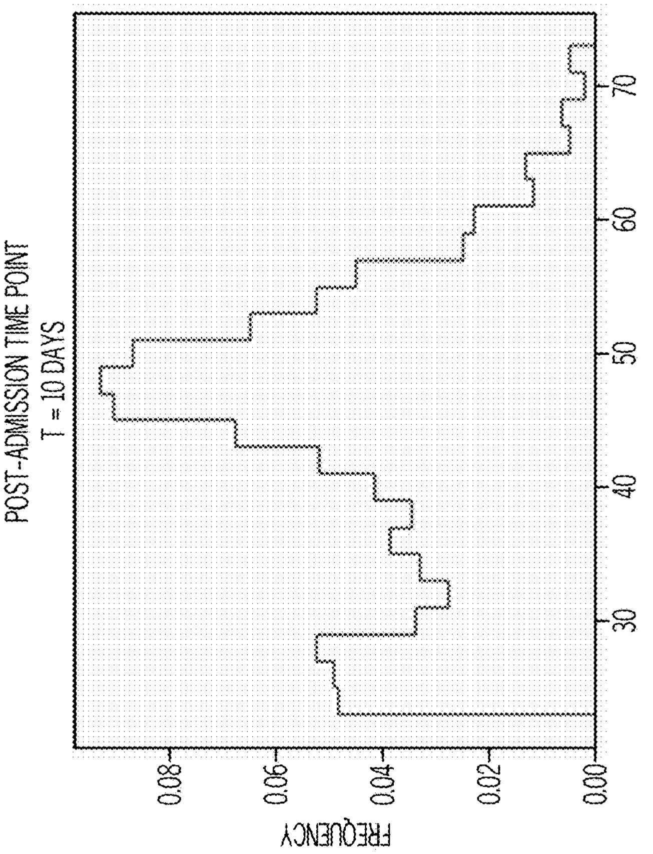
FIG. 21B1

DETECTION AND PREDICTION OF INFECTIOUS DISEASE

CROSS REFERENCES TO RELATED APPLICATIONS

This application is a continuation of International Patent Application No. PCT/US2019/0062665, titled "Detection and Prediction of Infectious Disease", filed Nov. 21, 2019, which claims the benefit of U.S. Provisional Application No. 62/770,182, titled "Detection and Prediction of Infectious Disease", filed Nov. 21, 2018, U.S. Provisional Application No. 62/770,181, titled "Direct-to-Library Methods, Systems and Compositions", filed Nov. 21, 2018, and U.S. Provisional Application No. 62/849,618, titled "Fragment Length Distributions and Methods of Using Such", filed May 17, 2019, each of which are hereby incorporated by reference in its entirety.

FIELD OF INVENTION

The present invention relates to the use of fragment length distributions in nucleic acid libraries to identify microbes, identify the type of host-microbe biological interaction, identify infection sites or site of localization, select the therapy or treatment, monitor treatment, monitor cytotoxicity, detect transplant rejection, monitor immune system response or activity, identify stage of infection, monitor transplant rejection and for use in cancer diagnostics.

BACKGROUND

For many microbial infections, the first stage is colonization. In some cases, a microbial infection can progress to persistent infection and may develop into an invasive disease stage. Examples of microbes that can develop into invasive disease include Cytomegalovirus, Epstein-Barr virus, *Heliobacter pylori, Clostridium difficile*, certain sexually-transmitted infections, and others. For patients infected with these types of microorganisms identifying an infection at the correct stage, colonization stage or invasive stage, can be an important factor in making effective treatment decisions. Site of localization also may impact the significance and available treatment options. Some microbe related diseases occur in the absence of what is considered typical colonization. For example, *C. botulinum* ingestion can be sufficient to cause symptoms.

Furthermore, infections at the invisible stage often present with no symptoms or non-specific symptoms that may resemble multiple other diseases. Consequently, such infections are often undiagnosed, misdiagnosed or treated symptomatically allowing the microorganism to persist and increasing the risk that the patient's infection will progress to invasive disease.

*Helicobacter pylori* (*H. pylori*) is the most common chronic bacterial infection in humans. It is estimated that 50% of the world's population is infected. In the United States, approximately 30% of adults are infected by age 50 with the majority of individuals infected during childhood. Chen, Y. and M. J. Blaser, J Infect Dis, 2008. 198 (4): p. 553-60. There are strong associations between *H. pylori* infection and gastrointestinal (GI) conditions, including chronic gastritis, peptic ulcer disease, gastric adenocarcinoma, and lymphoma. Peptic ulcer disease (PUD) is the most common manifestation of *H. pylori* infection and has an annual incidence of 0.1-0.19% for physician-diagnosed PUD. Sung, J. J., E. J. Kuipers, and H. B. El-Serag, Aliment Pharmacol Ther, 2009. 29 (9): p. 938-46. It is estimated that infected individuals have a lifetime risk of 10-20% of developing peptic ulcer disease. Kuipers, E. J., et al., Aliment Pharmacol Ther, 1995. 9 Suppl 2: p. 59-69.

The primary phenomenon responsible for the initiation of these disease manifestations is mucosal inflammation in response to the presence of *H. pylori*. However, only a small percentage of individuals with *H. pylori* will have inflammation associated with invasive *H. pylori* disease.

Currently, it is challenging to distinguish between patients who have an *H. pylori* invisible infection stage versus those who have a symptomatic stage or are at risk to progress to a symptomatic stage. While most infections with *H. pylori* are asymptomatic, patients with invasive disease may begin experiencing symptoms of persistent dyspepsia, such as abdominal pain, nausea or vomiting and lack of appetite. However, these non-specific symptoms could also be caused by other conditions and are experienced by healthy people. Some physicians will test all patients with unexplained persistent dyspepsia. Other physicians follow current guidelines, which recommend testing for *H. pylori* in individuals with active PUD, a history of documented peptic ulcer, or gastric MALT lymphoma. Chey, W. D., et al., Am J Gastroenterol, 2007. 102 (8): p. 1808-25. Thus, physicians following guidelines will only test patients with a high probability of *H. pylori*-associated disease, which could lead to undertreatment.

There are currently several methods to test for *H. pylori*. The existing non-invasive testing methods for *H. pylori* include stool antigen testing, urea breath test, and *H. pylori* serology. However, these methods can determine only whether *H. pylori* is present, but not whether there is *H. pylori* invasion or associated inflammation. Some practitioners will initiate primary treatment for eradication based on a positive result from one of the non-invasive tests, which may lead to overtreatment.

The current gold standard for diagnosing *H. pylori* disease is to perform an upper endoscopy to document (via biopsy) specific pathologic changes due to *H. pylori* invasion such as inflammation, atrophy, and intestinal metaplasia in conjunction with detection of *H. pylori* in biopsy samples. Dixon, M. F., et al., Helicobacter, 1997. 2 Suppl 1: p. S17-24. However, there are serious risks and potential complications from this procedure, including bleeding which can sometimes require a transfusion, infection, and tearing of the GI tract.

Overall, about 75% of patients that comply with primary treatment of *H. pylori* infection are considered cured after the first treatment, based on a negative *H. pylori* diagnostic assay for active infection that was previously positive prior to initiation of treatment. If the diagnostic test for active gastrointestinal *H. pylori* infection remains positive after completion of first-line therapy, the possibility of antibiotic-resistant *H. pylori* exists and would entail additional treatment until a negative diagnostic test result was obtained.

Next generation sequencing (NGS) can be used to gather massive amounts of data about the nucleic acid content of a sample. It can be particularly useful for analyzing nucleic acids in complex samples, such as clinical samples. However, before using the NGS methods, a starting sample must often be processed, which lowers nucleic acid recovery, delays sequencing, delays reporting of clinical calls, introduces errors, introduces bias, and often results in chemical waste requiring controlled handling. Errors and biases can affect results in many cases, such as when there are low abundance nucleic acids or target nucleic acids in patient samples. Current NGS methods focus on the abundance or relative abundance of particular reads or sequences. Further many sequencing library preparation methods and some next generation sequencing systems yield experimentally observed target nucleic acid fragment lengths and fragment length distributions that are biased away from the endogenous fragment lengths and fragment length distributions, particularly such as those methods and systems that utilize variable polyA tail tagging, unaccounted polyA tail tagging, thermal deactivation of enzymes, use of biased extraction methods, or use other measures that introduce nucleic acid length, secondary structure, and/or GC biases within the entire or partial range of target nucleic acid lengths and GC-content. Some such methods and systems prevent a successful bias correction even in the presence of process control molecules, if the biases are so strong that insufficient target nucleic acid and/or process control molecules are recovered within the entire or certain section of the relevant lengths and GC-contents for the final analysis.

Various methods including NGS have been used to identify a microbe present in a host, but most of those methods have focused on the abundance of microbial reads rather than the physical properties of the molecules being read. For example many extraction protocols, library generation protocols, and sequencing protocols include steps or processes designed to remove short nucleic acid fragment lengths. Short nucleic acid fragment lengths are also often sacrificed in order to minimize undesirable or incomplete byproducts of extraction, library generation, or amplification, such as primer dimers or adapter dimers. Microbial cell-free nucleic acids are an example of target nucleic acids that are particularly vulnerable to biases and depletion of short nucleic acids as their fragment lengths are below about 100 bp.

The current approach for distinguishing between an invisible or latent stage infection and other stages of infection after identifying a potential pathogen, can sometimes call for an invasive biopsy procedure. Non-invasive tests, such as serology, can detect markers of exposure to microbes, but do not indicate if the infection is active or at risk of progressing to invasive disease. Thus, there is a need for accurate, non-invasive approach for determining if a patient's organ has been infected and distinguishing which patients will remain in colonization stage, and which are at risk to develop a secondary invasive disease. The present disclosure provides non-invasive methods, compositions, and kits to detect an infection in a subject and determine if the infection is at a colonization or an invasive disease stage. The present disclosure also provides non-invasive methods to determine the site of localization in a subject and/or infection stage in a subject.

SUMMARY

An embodiment of the application provides a fragment length profile from a nucleic acid library wherein the nucleic acids used to prepare the nucleic acid library were obtained from a sample through an unbiased method, a method enabling bias correction, or a method with a reproducible bias. In various aspects the nucleic acid library was generated from an initial sample and the nucleic acids used to generate the nucleic acid library are not extracted from the initial sample before preparing the nucleic acid library or before initiating library generation process. Aspects of the methods may comprise nucleic acid sequencing as a step following the nucleic acid preparation and preceding determining the fragment length profile of target nucleic acids, multiple target nucleic acids or a subset of nucleic acids within a nucleic acid library. In aspects of the embodiment, the fragment length profile comprises one or more characteristics selected from the group comprising shape of the distribution, segment amplitude, segment fraction, peak shape, number of peaks, position of a maximum of a peak, the fragment count ratio for two or more segments, the height of helical phasing peaks, fragment count ratio at two different fragment lengths, ratio of fragment counts within two different fragment length ranges, the amount of fragments within a segment, the fragment length range within a segment, the ratio of maximum amplitudes for two or more segments, and fragment length distribution within a subset of reads, slope within a segment, peak width, the rate of count decay or increase within a segment, number of peaks, scaling of the count decay or increase within a segment.

Methods of generating a fragment length profile for a nucleic acid library are provided. The various methods comprise the steps of preparing a nucleic acid library from an initial sample using a bias-corrected recovery method, or a method with a reproducible bias, determining the number or normalized count of reads of multiple fragment lengths within the nucleic acid library, determining one or more fragment length characteristics of the nucleic acid library and generating a fragment length profile for the nucleic acid library using one or more fragment length characteristics. In aspects of the embodiment, the fragment length profile comprises one or more fragment length characteristics selected from the group comprising shape of the distribution, segment amplitude, peak shape, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, position of a maximum of a peak, number of peaks, and fragment length distribution within a subset of reads. Methods of generating a fragment length profile for a nucleic acid library are provided. The various methods comprise the steps of preparing a nucleic acid library from an initial sample comprising the steps of optionally adding one or more process control molecules to the initial sample to provide a spiked initial sample and generating a nucleic acid library from the spiked initial sample, wherein the nucleic acids used to generate the nucleic acid library are optionally not extracted from the initial sample prior to preparing the nucleic acid library. Aspects of the methods may comprise nucleic acid sequencing as a step following the nucleic acid preparation and preceding determining the fragment length profile. The methods of generating a fragment length profile for target nucleic acids within the nucleic acid library further comprise the steps of determining the number of reads of multiple fragment lengths within the nucleic acid library, determining one or more fragment length characteristics of the nucleic acid library and generating a fragment length profile for the nucleic acid library using one or more fragment length characteristics. In aspects of the embodiment, the fragment length profile comprises one or more fragment length characteristics selected from the group comprising shape of the distribution, segment amplitude, peak shape, number of peaks, position of a maximum of a peak, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, and fragment length distribution within a subset of reads. In certain aspects, the step of generating the nucleic acid library from the initial sample further comprises, consists of, or consists essentially of the steps of dephosphorylating nucleic acids from the initial sample to produce a group of dephosphorylated nucleic acids, denaturing the dephosphorylated nucleic acids to produce denatured nucleic acids, attaching a 3'-end adapter to the denatured nucleic acids to produce adapted nucleic acids, separating adapted nucleic acids, annealing a primer to the adapted nucleic acids and extending the primer with a polymerase to generate complementary strands, attaching a 5'-end adapter, eluting the strands and amplifying the complementary strands. Aspects of the methods may comprise nucleic acid sequencing as a step following the nucleic acid preparation and preceding determining the fragment length profile. In various embodiments the number of reads is a normalized number of reads. In some embodiments the fragment length profile is for at least one subset of reads within the nucleic acid library. In such embodiments, the methods further comprise the steps of identifying at least one subset of reads within the nucleic acid library and determining the fragment length distribution within each selected subset of reads. In some embodiments the step of generating the fragment length profile further comprises using two or more fragment length characteristics.

Methods of identifying a microbe present in a sample are provided. Methods of identifying or characterizing a microbe present in a sample comprise the steps of generating a fragment length profile for the sequencing reads from a nucleic acid library generated from the sample and aligned to the microbe reference sequence, comparing the fragment length profile to reference fragment length profiles of one or more microbes, and if the fragment length profile from the sample is similar to a reference fragment length profile of a microbe, then identifying the microbe as present in the sample. Aspects of the method comprise comparing fragment length profiles for target sequences from a nucleic acid library. In various embodiments, the fragment length profile may indicate the microbe is present as a pathogen or a commensal microorganism. In aspects of the methods, generating a fragment length profile for the nucleic acid library comprises the steps of preparing a nucleic acid library from an initial sample, quantifying the number of reads of multiple fragment lengths within the nucleic acid library; determining one or more fragment length characteristics of the nucleic acid library or at least one subset of reads the nucleic acid library, and generating a fragment length profile for the nucleic acid library or at least one subset of reads using one or more fragment length characteristics. The step of preparing a nucleic acid library from an initial sample further comprises the steps adding one or more process control molecules to the initial sample to provide a spiked initial sample and generating a nucleic acid library from the spiked initial sample, wherein nucleic acids used to generate the nucleic acid library are not extracted from the initial sample before preparing the nucleic acid library. Aspects of the methods may comprise nucleic acid sequencing as a step following the nucleic acid preparation and preceding determining the fragment length profile. In aspects of the embodiment, the fragment length profile comprises one or more fragment length characteristics selected from the group comprising shape of the distribution, segment amplitude, peak shape, number of peaks, position of the maximum of the peak, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, and fragment length distribution within a subset of reads. In various aspects of the methods, the fragment length profile comprises at least one fragment length characteristic selected from the group comprising fragment count ratio for two or more segments, peak shape, peak width, the rate of count decay or increase within a segment, number of peaks, scaling of the count decay or increase within a segment, position of the maximum of the peak.

Methods of determining the site of localization in a subject are provided. The methods comprise the steps of generating a fragment length profile for target nucleic acids in a nucleic acid library or the entire nucleic acid library generated from the sample, comparing the fragment length profile to a reference fragment length profile of one or more source sites, and if the fragment length profile from the sample is similar to a fragment length profile from a first source site, then predicting the first site as a site of localization, if the fragment length profile from the sample is similar to a fragment length profile from a second source site, then predicting the second site as a site of localization. In embodiments of the methods, generating one or more fragment length profile for the nucleic acid library comprises the steps of preparing a nucleic acid library from an initial sample, quantifying the number of reads of multiple fragment lengths within the nucleic acid library, generating a fragment length profile for target nucleic acids in a nucleic acid library or the entire nucleic acid library nucleic acid library using one or more fragment length characteristics. In embodiments of the method, preparing a nucleic acid library from an initial sample further comprises the steps of adding one or more process control molecules to the initial sample to provide a spiked initial sample and generating a nucleic acid library from the spiked initial sample, wherein nucleic acids used to generate the nucleic acid library are not extracted from the initial sample before preparing the nucleic acid library. Aspects of the methods may comprise nucleic acid sequencing as a step following the nucleic acid preparation and preceding determining the fragment length profile. In aspects of the embodiment, the fragment length profile comprises one or more fragment length characteristics selected from the group comprising shape of the distribution, segment amplitude, peak shape, number of peaks, a position of the maximum of the peak, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, peak width, the rate of count decay or increase within a segment, number of peaks, scaling of the count decay or increase within a segment, and fragment length distribution within a subset of reads. In aspects of the methods, the site of localization is selected from the group of source sites comprising, consisting of, or consisting essentially of deep tissue, lung, liver, bone, kidney, brain, heart, sinus, GI tract, spleen, skin, joint, ear, nose, mouth, bloodstream and blood.

Methods of monitoring transplant status in a subject are provided. The methods of monitoring transplant status comprise the steps of generating a baseline fragment length profile from a nucleic acid library from a sample obtained from the subject, generating a second fragment length profile for a nucleic acid library generated from a second sample obtained from the subject and comparing the second fragment length profile to the baseline fragment length profile. If the second fragment length profile differs from the baseline fragment length profile then internally administering an increased amount of an anti-rejection therapy to the subject, wherein a risk of rejection in a subject with a transplant is lower following the administration of the anti-rejection therapy. If the second fragment length profile is similar to the baseline fragment length profile, then maintaining or reducing an anti-rejection therapy, wherein the risk of a side-effect of the anti-rejection therapy in the subject is lower than it would be if the subject received an increased amount of the anti-rejection therapy. Aspects of the method comprise the step of comparing a fragment length profile for target nucleic acids in a nucleic acid library or the entire library from a sample obtained from a subject with a transplant and comparing the profile to a reference fragment length profile.

Methods of monitoring toxicity of a compound administered to a subject are provided. The methods comprise the steps of generating a fragment length profile for a nucleic acid library or for target nucleic acids in the nucleic acid library prepared from a sample obtained from the subject and comparing the fragment length profile to one or more reference fragment length profiles. In aspects of the method, the subject has cancer, is at risk for cancer or exhibits a cancer related symptom. In aspects of the method, the one or more reference fragment length profiles were generated from a nucleic acid library obtained from a subject or cell exposed to the compound. In aspects of the method, the one or more reference fragment length profiles comprises a baseline fragment length profile. In aspects of the method, the compound is a chemotherapeutic agent. In embodiments of the method, the step of generating a fragment length profile for a nucleic acid library comprises the steps of preparing a nucleic acid library from an initial sample using a bias-corrected recovery method; determining the number of reads of multiple fragment lengths within the nucleic acid library; determining one or more fragment length characteristics of the nucleic acid library; and generating a fragment length profile for the nucleic acid library using one or more fragment length characteristics. Aspects of the methods may comprise nucleic acid sequencing as a step following the nucleic acid preparation and preceding determining the fragment length profile. In aspects of the embodiment, the fragment length profile comprises one or more fragment length characteristics selected from the group comprising shape of the distribution, segment amplitude, peak shape, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, and fragment length distribution within a subset of reads. In embodiments of the methods, generating a fragment length profile for the nucleic acid library comprises the steps of preparing a nucleic acid library from an initial sample further comprising adding one or more process control molecules to the initial sample to provide a spiked initial sample and generating a nucleic acid library from the spiked initial sample, wherein nucleic acids used to generate the nucleic acid library are not extracted from the initial sample before preparing the nucleic acid library; quantifying the number of reads of multiple fragment lengths within the nucleic acid library; determining one or more fragment length characteristics of the nucleic acid library; and generating a fragment length profile for the nucleic acid library using one or more fragment length characteristics. In aspects of the embodiment, the fragment length profile comprises one or more fragment length characteristics selected from the group comprising shape of the distribution, segment amplitude, peak shape, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, and fragment length distribution within a subset of reads.

The present invention is directed to methods to predict the risk that an organism (or multiple organisms) present in a host create a localized or systemic environmental change or invasion of organs or anatomical systems with substantially negative health outcomes. An organism is invasive if it passes a barrier or translocates from one organ or anatomical structure to another, invades a structure beyond the tissue layer it occupied in a colonizing state to create a localized invasion, it changes the environment of a structure such that it creates significant negative impacts to the structure or causes DNA mutations or inflammation, or it otherwise overwhelms the host's immune system.

In certain embodiments, the risk level is based on the abundance of the organism in the host as compared to an asymptomatic control or infected control. In other embodiments, the abundance is a threshold or range. In yet other embodiments, the risk level is calculated as a clinical decision-making score based on one or more of the following: abundance of the organism, clinical history of the patient, chronicity of disease, genetic biomarker factors and patient characteristics (such as age, gender, etc.), fragment length distribution profile, and a fragment length distribution profile characteristic.

In an aspect there is provided a method to determine the infection stage of a subject suspected of having a microbial infection comprising:

(a) performing high throughput sequencing of nucleic acids from said biological sample;
(b) performing bioinformatics analysis to identify microbial nucleic acid sequences present in said biological sample; and
(c) calculating a measurement for the nucleic acids and comparing the measurement to a control, thereby determining the infection stage for any microbe identified in said biological sample.

In some embodiments the method further comprises one or more steps selected from the group consisting of (a) extracting nucleic acids from a portion of a biological sample obtained from the subject and (b) adding synthetic nucleic acid spike-ins.

In one embodiment, the measurement of step (c) is selected from an absolute abundance for the cell-free microbial nucleic acid sequences, a distribution of fragment lengths for the nucleic acids sequences, a characteristic of the nucleic acid fragment length distribution profile, or a combination thereof. In another embodiment, the measurement of step (c) is an absolute abundance and distribution of fragment lengths for the target pathogen.

In a second embodiment, the subject has symptoms of an infection or is at risk of having an infection.

In a third embodiment, the infection stage is an invisible phase, a symptomatic phase of an infection, a treatment phase or an eradication stage. In a fourth embodiment, the method further comprises repeating the method over time to monitor an infection, stage of infection, efficacy of a treatment for an infection, or detect the onset of an infection. In aspects, the methods may further comprise changing a therapeutic regimen.

In a fifth embodiment, the method further comprises administering a therapeutic regimen to the subject based on the determined infection stage.

In a sixth embodiment, the high-throughput sequencing assay is next generation sequencing, massively-parallel sequencing, pyrosequencing, sequencing-by-synthesis, single molecule real-time sequencing, polony sequencing, DNA nanoball sequencing, heliscope single molecule sequencing, nanopore sequencing, Sanger sequencing, shotgun sequencing, or Gilbert's sequencing.

In a seventh embodiment, the sample is blood, plasma, serum, cerebrospinal fluid, synovial fluid, bronchial-alveolar lavage, sputum, urine, stool, saliva, or a nasal sample.

In an eighth embodiment, method further comprises identifying antibiotic-resistant gene(s) of the target pathogen.

In a ninth embodiment, method further comprises identifying at least one risk factor in the subject's genomic DNA.

In a tenth embodiment, the nucleic acid is cell-free DNA and/or cell-free RNA. The nucleic acids may comprise cell-free pathogen DNA. The nucleic acids may comprise cell-free pathogen RNA. The nucleic acids may comprise cell-free microbial DNA. The nucleic acids may comprise cell-free microbial RNA.

In an eleventh embodiment, the target pathogen is *Heliobacter pylori, Clostridium difficile, Haemophilus influenza, Salmonella, Streptococcus pneumoniae*, Cytomegalovirus, hepatitis virus B, hepatitis virus C, human papillomavirus, Epstein-Barr virus, human T-cell lymphoma virus 1, Merkel cell polyomavirus, Kaposi's sarcoma virus, Human Herpesvirus 8, Chlamydia, Gonorrhea, Syphilis, or Trichomoniasis.

In a twelfth embodiment, the subject previously had another test or other clinical tests. In an embodiment, the other clinical test is stool antigen test, urea breath test, serology, urease testing, histology, bacterial culture and sensitivity testing, biopsy, or endoscopy.

In a thirteenth embodiment, the target pathogen nucleic acids is DNA and/or RNA. The pathogen nucleic acids comprise cell-free DNA. The nucleic acids comprise pathogen cell-free RNA.

In a fourteenth embodiment, synthetic nucleic acid spike-ins comprises at least 1000 unique synthetic nucleic acids to the sample, wherein each of the 1000 unique synthetic nucleic acids comprises (i) an identifying tag and (ii) a variable region comprising at least 5 degenerate bases. In a further embodiment, the method further comprises (a) optionally extracting the nucleic acids from the spiked-sample;
(b) generating a spiked-sample library;
(c) optionally enriching the spiked-sample library;
(d) conducting a high-throughput sequencing assay to obtain sequence reads from the spiked-sample library;
(e) calculating a diversity loss value of the 1,000 unique synthetic nucleic acids and;
(f) calculating a measurement for the nucleic acids and comparing the measurement to a control, thereby determining the infection stage in the subject.

In a yet further embodiment, the at least 1,000 unique synthetic nucleic acids are synthetic nucleic acids as described in U.S. Pat. No. 9,976,181.

In another aspect there is a method of determining the infection stage of *Heliobacter pylori* in a subject comprising:

a) optionally, extracting cell-free nucleic acids from a biological sample obtained from said subject;
b) adding synthetic nucleic acid spike-ins to the sample;
c) performing high throughput sequencing of nucleic acids from said biological sample;
d) performing bioinformatics analysis to identify *Heliobacter pylori* nucleic acid sequences present in said biological sample; and
e) calculating a measurement for the *Heliobacter pylori* nucleic acids and comparing the measurement to a control, thereby determining the infection stage for *Heliobacter pylori* in said subject.

In a first embodiment, the measurement is an absolute abundance or a distribution of fragment lengths or combination thereof for *Heliobacter pylori*. In an embodiment, the measurement is an absolute abundance for *Heliobacter pylori*. In another embodiment, the measurement is a distribution of fragment lengths for *Heliobacter pylori*. In yet another embodiment, the measurement is an absolute abundance and distribution of fragment lengths for *Heliobacter pylori*. In various embodiments, the steps of the method may be carried out in varying order.

In a second embodiment, the subject has symptoms of a *Heliobacter pylori* infection or is at risk of having a *Heliobacter pylori* infection. In an embodiment, the infection stage is an invisible phase, a symptomatic phase of an infection, a treatment phase or an eradication stage.

In a third embodiment, the method further comprises repeating the method over time to monitor an infection or efficacy of a treatment for an infection.

In an aspect there is a method of determining the infection stage of *Heliobacter pylori* in subject comprising:

(a) making a spiked-sample by obtaining a sample from a subject comprising cell-free nucleic acids and adding one or more process control molecules;
(b) optionally, extracting the nucleic acids from the spiked-sample;
(c) generating a spiked-sample library, wherein the generating comprises
(i) attaching an adapter to nucleic acids and (ii) amplifying;
(d) optionally, enriching the spiked-sample library;
(e) conducting a high-throughput sequencing assay to obtain sequence reads from the spiked-sample library;
(f) calculating a diversity loss value of the 1,000 unique synthetic nucleic acids and;
(g) calculating a measurement for the cell-free nucleic acids and comparing the measurement to a control, thereby determining the infection stage of *Heliobacter pylori* in the subject.

In a yet further embodiment, the at least 1,000 unique synthetic nucleic acids are synthetic nucleic acids as described in U.S. Pat. No. 9,976,181.

In a second embodiment, the high-throughput sequencing assay is next generation sequencing, massively-parallel sequencing, pyrosequencing, sequencing-by-synthesis, single molecule real-time sequencing, polony sequencing, DNA nanoball sequencing, heliscope single molecule sequencing, nanopore sequencing, Sanger sequencing, shotgun sequencing, or Gilbert's sequencing.

In a third embodiment, the sample is blood, plasma, serum, cerebrospinal fluid, synovial fluid, bronchial-alveolar lavage, urine, stool, saliva, or a nasal sample.

In a fourth embodiment, the method further comprises administering a therapeutic regimen to the subject, wherein the treatment can be administered at any stage of the infection cycle.

In a fifth embodiment, the method further comprises identifying antibiotic-resistant gene(s) of the target pathogen.

In a sixth embodiment, the cell-free nucleic acid is DNA and/or RNA. The nucleic acids comprise cell-free pathogen DNA. The nucleic acids comprise cell-free pathogen RNA.

In a seventh embodiment, the subject previously had another other clinical test. In an embodiment, the other clinical test is stool antigen test, urea breath test, serology, urease testing, histology, bacterial culture and sensitivity testing, biopsy, or endoscopy.

In an eighth embodiment, the target pathogen nucleic acids is DNA and/or RNA. The pathogen nucleic acids comprise cell-free DNA. The nucleic acids comprise pathogen cell-free RNA. The target pathogen nucleic acids comprise a mixture of cell-free DNA and cell-free RNA.

Another aspect provides a method of determining a site of localization in a subject infected by a pathogen comprising:

(a) obtaining a sample from a subject comprising nucleic acids and adding one or more process control molecules, thereby generating a spiked sample;
(b) optionally, extracting the nucleic acids from the spiked-sample;
(c) generating a library from the spiked-sample, where in generating comprises attaching an adapter to nucleic acids and amplifying;
(d) optionally, enriching the spiked-sample;
(e) conducting a high-throughput sequencing assay to obtain sequence reads from the spiked-sample by comparing to a reference genome;
(f) optionally, calculating a diversity loss value and;
(g) calculating a measurement for the nucleic acids and comparing the measurement to a control, thereby determining a site of localization in the subject.

In a first embodiment, the measurement is an absolute abundance or a distribution of fragment lengths or combination thereof for a target pathogen. In an embodiment, the measurement is an absolute abundance for a target pathogen. In another embodiment, the measurement is a distribution of fragment lengths for a target pathogen. In yet another embodiment, the measurement is an absolute abundance and distribution of fragment lengths for a target pathogen.

In a second embodiment, the site of localization is a tissue. In a further embodiment, the site of localization is a tissue type. In a yet further embodiment, the site of localization is an organ. In another further embodiment, the site of localization is a tissue type comprising an organ.

In a third embodiment, the subject has symptoms of an infection or at risk of having an infection. In a further embodiment, the subject has been previously identified as being infected with *Heliobacter pylori, Clostridium difficile, Haemophilus influenza, Salmonella, Streptococcus pneumoniae*, Cytomegalovirus, Hepatitis B Virus, Hepatitis C Virus, Human papillomavirus, Epstein-Barr virus, Human T-cell lymphoma virus 1, Merkel cell polyomavirus, Kaposi's sarcoma virus, Human Herpesvirus 8, *Chlamydia*, Herpes Simplex Virus, *Neisseria* species, *Treponema* species, or *Trichomonas* species.

In a fourth embodiment, the method is repeated over time to monitor an infection or efficacy of a treatment for an infection.

In a fifth embodiment, the method further comprises administering a therapeutic regimen to the subject based on the determined infection stage.

In a sixth embodiment, the at least 1,000 unique synthetic nucleic acids are synthetic nucleic acids as described in U.S. Pat. No. 9,976,181.

In a seventh embodiment, the high-throughput sequencing assay is next generation sequencing, massively-parallel sequencing, pyrosequencing, sequencing-by-synthesis, single molecule real-time sequencing, polony sequencing, DNA nanoball sequencing, heliscope single molecule sequencing, nanopore sequencing, Sanger sequencing, shotgun sequencing, or Gilbert's sequencing.

In an eighth embodiment, the sample is blood, plasma, serum, cerebrospinal fluid, synovial fluid, bronchial-alveolar lavage, urine, stool, saliva, nasal, or tissue sample.

In a ninth embodiment, the method further comprises identifying antibiotic-resistant gene(s) of the pathogen.

In a tenth embodiment, the method further comprises identifying risk factor in the subject's genomic DNA.

In an eleventh embodiment, the target pathogen nucleic acids is DNA and/or RNA. The pathogen nucleic acids comprise cell-free DNA. The nucleic acids comprise pathogen cell-free RNA. The target pathogen nucleic acids comprise a mixture of cell-free DNA and cell-free RNA.

In a twelfth embodiment, the cell-free nucleic acid is DNA and/or RNA. The nucleic acids comprise cell-free pathogen DNA. The nucleic acids comprise cell-free RNA. The nucleic acids comprise cell-free pathogen RNA. The nucleic acids comprise cell-free subject RNA. The nucleic acids comprise pathogen and subject cell-free RNA.

In an aspect, there is provided a method to determine the infection stage of a subject suspected of having a microbial infection comprising (a) Providing a sample from said subject comprising nucleic acids
(b) Adding at least 1000 unique synthetic nucleic acids to the sample, thereby generating a spiked-sample;
(c) generating a library from the spiked-sample;
(d) conducting a high-throughput sequencing assay to obtain sequence reads from the spiked-sample;
(e) determining the infection stage of said subject based upon the sequence reads.

In an embodiment, the sample is selected from blood, plasma, serum, cerebrospinal fluid, synovial fluid, bronchial-alveolar lavage, urine, stool, saliva, nasal, and tissue sample. The sample is a blood, plasma, serum, cerebrospinal fluid, or synovial fluid.

In a yet further embodiment, the at least 1,000 unique synthetic nucleic acids are synthetic nucleic acids as described in U.S. Pat. No. 9,976,181.

In a further embodiment, the high-throughput sequencing assay is next generation sequencing, massively-parallel sequencing, pyrosequencing, sequencing-by-synthesis, single molecule real-time sequencing, polony sequencing, DNA nanoball sequencing, heliscope single molecule sequencing, nanopore sequencing, Sanger sequencing, shotgun sequencing, or Gilbert's sequencing.

In another further embodiment, the determination of the infection stage is based on an absolute abundance or a fragment length distribution profile or combination thereof for a target pathogen. In an embodiment, the determination based on an absolute abundance for a target pathogen. In another embodiment, the determination based on a distribution of fragment lengths for a target pathogen. In yet another embodiment, the determination based on an absolute abundance and distribution of fragment lengths for a target pathogen.

An aspect of the application provides a method of determining infection stage in a subject. The method comprises the steps of generating a fragment length profile for a nucleic acid library generated from a sample obtained from said subject, comparing the fragment length profile to a reference fragment length profile, and if the fragment length profile from the sample is similar to a fragment length profile from a symptomatic subject, then determining the infection stage indicates the subject has an increased risk of exhibiting a microbe related symptom and if the fragment length profile from the sample is similar to a fragment length profile from an asymptomatic subject, then determining the infection in the invisible stage. In an aspect, the fragment length profile is a non-microbial host nucleic acid library fragment length profile. In various aspects, the method further comprises the steps of determining an abundance of at least one significant microbe in a sample from the subject, comparing the abundance to a threshold and comparing the fragment length profile to a reference fragment length profile. If the fragment length profile from the sample is similar to a fragment length profile from a symptomatic subject and said abundance is comparable to or above a threshold, then determining the infection stage indicates the subject has an increased risk of exhibiting a microbe related symptom. If the fragment length profile from the sample is similar to a fragment length profile from an asymptomatic subject, then determining the infection is in the invisible stage. In an aspect, the method further comprises the step of administering an anti-microbial agent to a subject determined to have an increased risk of exhibiting a microbe-related symptom.

A method of determining the infection stage of a subject suspected of having a microbial infection comprising performing high-throughput sequencing of nucleic acids from the biological sample, performing bioinformatics analysis to identify nucleic acid sequences present in the biological sample and calculating a measurement for the nucleic acids and comparing the measurement to a control thereby determining the infection stage for a microbe identified in the biological sample. The method may further comprise one or more steps selected from the group consisting of (i) extracting nucleic acids from a biological sample obtained from the subject and (ii) adding synthetic nucleic acid spike-ins to biological sample obtained from the subject. In an aspect, the nucleic acids comprise microbial nucleic acids, host nucleic acid or both microbial and host nucleic acids. In an aspect, the nucleic acids comprise cell-free microbial nucleic acids, host nucleic acid or both microbial and host nucleic acids. In an aspect the measurement is selected from the group of measurements consisting of an absolute abundance for the nucleic acids, a fragment length distribution profile for the nucleic acids and both an absolute abundance and a fragment length distribution profile. In an aspect, the infection stage is selected from an invisible stage of infection, colonization stage, symptomatic stage, active stage, invasive disease stage, resolution stage, treatment phase or an eradication stage. In an aspect, the method further comprises administering a therapeutic regimen to a subject based on the determined infection stage. The method may further comprise repeating the method over time to monitor the infection or efficacy of a treatment for the infection. In some aspects, the microbe is selected from the group comprising *Heliobacter pylori, Clostridium difficile, Haemophilus influenza, Salmonella, Streptococcus pneumoniae*, Cytomegalovirus, Hepatitis B Virus, Hepatitis C Virus, Human papillomavirus, Epstein-Barr virus, Human T-cell lymphoma virus 1, Merkel cell polyomavirus, Kaposi's sarcoma virus, Human Herpesvirus 8, *Chlamydia*, Herpes Simplex Virus, Neisseria species, *Treponema* species, or *Trichomonas* species. In aspects adding the synthetic nucleic acid spike-ins further comprises making a spiked-sample by obtaining a sample from a subject comprising cell-free nucleic acids and adding one or more process control molecules; extracting the nucleic acids from the spiked-sample; generating a spiked-sample library; enriching the spiked-sample library; conducting a high-throughput sequencing assay to obtain sequence reads from the spiked-sample library; calculating a diversity loss value of the 1,000 unique synthetic nucleic acids and; calculating a measurement for the cell-free nucleic acids and comparing the measurement to a control, thereby determining the infection stage in the subject.

In an embodiment, the application provides a method of determining the infection stage of *Heliobacter pylori* in a subject comprising extracting nucleic acids from a biological sample obtained from the subject, adding synthetic nucleic acid spike-ins to the sample, performing high throughput sequencing of nucleic acids from the biological sample, performing bioinformatic analysis to identify cell-free *Heliobacter pylori* nucleic acid sequences present in a biological sample and calculating a measurement for the cell-free *Heliobacter pylori* nucleic acids and comparing the measurement to a control, thereby determining the infection stage for *Heliobacter pylori* in the subject.

In an embodiment the application provides a method of determining the infection stage of *Heliobacter pylori* in subject comprising: making a spiked-sample by obtaining a sample from a subject comprising cell-free nucleic acids and adding one or more process control molecules; extracting the nucleic acids from the spiked-sample; generating a spiked-sample library, wherein the generating comprises (i) attaching an adapter to nucleic acids and (ii) amplifying; optionally, enriching the spiked-sample library; conducting a high-throughput sequencing assay to obtain sequence reads from the spiked-sample library; calculating a diversity loss value of the 1,000 unique synthetic nucleic acids and calculating a measurement for the cell-free nucleic acids and comparing the measurement to a control, thereby determining the infection stage of *Heliobacter pylori* in the subject.

An embodiment provides methods of determining a site of localization in a subject infected by a pathogen comprising obtaining a sample from a subject comprising nucleic acids, adding one or more process control molecules to the initial sample to provide a spiked sample, optionally extracting the nucleic acids from the spiked sample, generating a library from the spiked sample, wherein generating comprises attaching an adapter to said nucleic acids and amplifying; optionally, enriching the spiked sample, conducting a high-throughput sequencing assay to obtain sequence reads from the spiked sample by comparing to a reference genome; determining one or more fragment length characteristics of the nucleic acid library, generating a fragment length profile for a nucleic acid library generated from the sample, comparing the fragment length profile to a reference fragment length profile of one or more source sites and if the fragment length profile from the sample is similar to a fragment length profile from a first source site, then identifying the first site as a site of localization; if the fragment length profile from the sample is similar to a fragment length profile from a second source site, then identifying the second site as a site of localization.

An aspect provides a method of determining a site of localization in a subject infected by a pathogen comprising obtaining a sample from a subject comprising cell-free nucleic acids and adding one or more process control molecules, thereby generating a spiked-sample; optionally extracting the nucleic acids from the spiked-sample; generating a library from the spiked-sample, wherein generating comprises attaching an adapter to said nucleic acids and amplifying; optionally, enriching the spiked sample; conducting a high-throughput sequencing assay to obtain sequencing reads from the spiked-sample by comparing to a reference genome; calculating a diversity loss value of the 1000 unique synthetic nucleic acids and calculating a measurement for the cell-free nucleic acids and comparing the measurement to a control, thereby determining the site of localization in the subject.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15A provides plots of abundance in units of molecules per microliter (MPM) for the microbes found at significant levels in the indicated sample type. FIG. 15B provides plots of MPM abundances in asymptomatic samples (AP) and diagnostic positive samples (DP) for the microbes of the same species present in both types of samples. FIG. 15C provides an example of a representative TapeStation electropherogram of a library obtained from a diagnostic positive sample included in this study. The data was obtained on TapeStation using a HS TapeStation tape D1000 with the Loading Buffer and DNA Ladder according to the manufacturer's instructions. The Upper and Lower DNA markers are indicated in the plot. A subset of regions of interests in the fragment length ranges are indicated in the plot for orientation (note that the fragment lengths in an electropherogram of a library reflect the lengths of fully adapted nucleic acid molecules rather than the actual lengths of the endogenous originals). Library fragment length is shown on the x-axis; normalized intensity (FU) is shown on the y-axis. FIG. 15D provides plots of the molar fractions of the sequencing reads mapping to human reference and longer than 64 bp (i.e. the majority of these reads are of nucleosomal length) after the adapter sequence trimming step for asymptomatic samples (AP) and diagnostic positive samples (DP) included in this study. FIG. 15E provides a summary comparison of the maximum MPM abundance for the microbes found at significant levels in each asymptomatic (AP) and diagnostic positive (DP) sample in this study with the fraction of the long human reads as defined in the caption to FIG. 15D and found in the same samples. Only AP and DP samples where our assay detected microbes at the significant levels were included in this analysis. Arrows indicate the AP samples that showed maximum MPMs and long human read fraction higher than 3000, and 0.4, respectively. FIG. 15F provides a summary comparison of the maximum MPM abundances for the microbes found at significant levels in asymptomatic samples (AP) and diagnostic negative samples (DN), with the fraction of the long human reads as defined for FIG. 15D and found in the same samples. Only AP and DN samples where our assay detected microbes at the significant levels were included in this analysis.

FIG. 16D depicts the results of training a predictor of an infection state based on the significant pathogen fragments recovered for sequencing from asymptomatic and symptomatic patients. The left panel shows probabilities for a sample to be asymptomatic based the model trained only on the reads derived from the significant pathogens. The right panel depicts the regions of the fragment lengths relevant to each infection state recognized by model trained on the significant pathogens. FIG. 16E depicts the results of training a predictor of an infection state based on the bacterial fragments recovered for sequencing from asymptomatic and symptomatic patients. The left panel shows probabilities for a sample to be asymptomatic based on bacteria-trained model. The right panel depicts the regions of the fragment lengths relevant to each infection state recognized by the bacteria-trained model. FIG. 16F depicts the results of training a predictor of an infection state based on the eukaryotic microbial fragments recovered for sequencing from asymptomatic and symptomatic patients. The left panel shows probabilities for a sample to be asymptomatic based on eukaryota-trained model. The right panel depicts the regions of the fragment lengths relevant to each infection state recognized by the eukaryota-trained model. FIG. 16G depicts the results of training a predictor of an infection state based on the viral fragments recovered for sequencing from asymptomatic and symptomatic patients. The left panel shows probabilities for a sample to be asymptomatic based on virus-trained model. The right panel depicts the regions of the fragment lengths relevant to each infection state recognized by the virus-trained model.

FIG. 17A1-17A10 depict the normalized fragment length distributions for the microbes suspected to be infecting lungs are shown with each panel showing one distribution for the indicated species of microbe and a Sample ID indicated at the top of each panel. The frequency is defined as the count of the reads aligning to the reference of the indicated microbe of a particular read (fragment) length normalized by the total count of the reads aligning to the reference of the indicated microbe. FIG. 17B1-17B10 depict the normalized fragment length distributions for the microbes suspected of infecting the bloodstream are shown with each panel showing one distribution for the indicated species of microbe and a Sample ID indicated at the top of each panel. The frequency is defined as the count of the reads aligning to the reference of the indicated microbe of a particular read (fragment) length normalized by the total count of the reads aligning to the reference of the indicated microbe.

FIG. 18A1-18A2 depict representative normalized fragment length distribution for two microbes detected in the venous draws of two different donors. The normalized fragment length distribution of the reads mapping to *Haemophilus influenzae*, a microbe detected in the plasma obtained from the venous blood draw of Donor 1 is shown in the left panel. The normalized fragment length distribution of the reads mapping to *Streptococcus thermophilus*, a microbe detected in the plasma obtained from the venous blood draw of Donor 2 is shown in the right panel. FIG. 18B1-18B4 depict normalized fragment length distributions for the microbes detected in the biological samples obtained during the capillary draw collection process from the same two donors and drawn at the same sampling time as the venous draws in FIG. 18A. The upper left panel shows the normalized fragment length distribution of *Haemophilus influenzae* as detected in the biological sample obtained during the capillary draw collection process from Donor 1. The lower left panel shows the normalized fragment length distributions for the additional microbes detected in the biological sample obtained during the capillary draw collection process from Donor 1. Their mean distribution pattern is shown in bold black line. The upper right panel shows the normalized fragment length distribution of *Strep-*

*tococcus thermophilus* as detected in the biological sample obtained during the capillary draw collection process from Donor 2. The lower right panel shows the normalized fragment length distributions for the additional microbes detected in the biological sample obtained during the capillary draw collection process from Donor 2. Their mean distribution pattern is shown in bold black line. FIG. 18C1-18C2 compare the abundances for the co-occurring microbes in the two replicates of the biological sample obtained during the capillary draw collection process for Donor 1 (left panel) and Donor 2 (right panel). FIG. 18D1-18D2 depict a comparison of the microbial abundances for the microbes detected in the biological sample obtained with a capillary blood draw procedure (x-axis) to the microbial abundance in the Negative Microvette® Samples. The results obtained for Donor 1, and Donor 2 are shown in the left and right panel, respectively.

FIG. 19A1-19A3 Subject RD-02 was orthogonally confirmed to have a bloodstream infection by *Enterobacter* species. The panels depict normalized fragment length distributions for the sequences aligning to *Enterobacter cloacae* complex in nucleic acid libraries generated from plasma samples collected at different collection times indicated above each panel. FIG. 19B1-19B5 Subject RD-11 was orthogonally confirmed to have endocarditis caused by *Staphylococcus aureus* infection. The panels depict normalized fragment length distributions for the sequences aligning to *Staphylococcus aureus* in nucleic acid libraries generated from plasma samples collected at different collection times indicated above each panel. FIG. 19C1-19C4 Subject RD-13 was orthogonally confirmed to febrile neutropenia caused by *Escherichia coli* infection. The panels depict normalized fragment length distributions for the sequences aligning to *Escherichia coli* in nucleic acid libraries generated from plasma samples collected at different collection times indicated above each panel.

FIG. 21A1-21A4 show pairs of orthogonally confirmed and orthogonally unconfirmed microbes in the plasma sample collected at the admission time point (t=0) for two subjects, RD-06 and RD-13. The orthogonally confirmed microbe in RD-06 (*Staphylococcus aureus*) is shown in the upper left panel. The unconfirmed microbe in RD-06 (*Haemophilus influenzae*) is shown in the lower left panel. The orthogonally confirmed microbe in RD-13 (*Escherichia coli*) is shown in the upper right panel. The unconfirmed microbe in RD-13 (*Prevotella melaninogenica*) is shown in the lower right panel. FIG. 21B1-21B2 The normalized fragment length distributions for *Enterococcus gallinarum*, an orthogonally unconfirmed microbe detected at several post-admission time points in plasma samples collected from subject RD-15. The time points are indicated above the panels.

FIG. 22A shows an example where the long human fraction (>60 bp) decreased during the treatment. FIG. 22B shows an example where the long human fraction (>60 bp) fluctuated during the treatment. FIG. 22C shows an example where the long human fraction (>60 bp) increased during the treatment.

DETAILED DESCRIPTION

Figure 1:
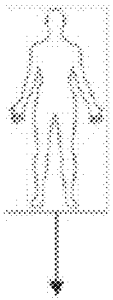
FIG. 1 depicts one of the methods of this disclosure.

Next generation sequencing (NGS) can be used to gather massive amounts of data about the nucleic acid content of a sample. It can be particularly useful for analyzing nucleic acids in complex samples, such as clinical samples. Heretofore, these NGS systems focused on determining the abundance of individual reads. The primary properties of interest prior to this work has been the sequence of each read and the abundance of reads associated with a particular source. This is particularly true for microbial nucleic acids, and cell-free microbial nucleic acids. In part this has been due to the fact that previous sample processing required for many NGS systems often result in errors and biases particularly for low abundance nucleic acids. Karius developed methods of preparing nucleic acid libraries from initial samples that reduce bias in the recovery of the nucleic acid libraries from an initial sample or that allow correction of the bias. The reduced bias in the nucleic acid libraries obtained from the initial samples has allowed development of fragment length profiles and methods of generating fragment length profiles for nucleic acid libraries or target nucleic acids within the nucleic acid libraries. There is a need for efficient and accurate methods for generating fragment length profiles for nucleic acid libraries. This need can be seen, for example, with respect to distinguishing between closely related microbes, determining whether a microbe is present as a pathogen or a commensal microorganism, determining microbe's biological relationship with a host, predicting infection or colonization site in a subject, monitoring transplant status, monitoring fetal development and status, tumor monitoring, monitoring the status and response of the immune system, and monitoring toxicity of a compound administered to a subject.

A fragment length profile comprises one or more fragment length characteristics for a nucleic acid library or a subset of reads from within a nucleic acid library. A fragment length profile may comprise 1, 2, 3, 4, 5, 6, 7, 8, 9, 10, 11, 12, 13, 14, 15, 16, 17, 18, 19, 20 or more fragment length characteristics. A weighted value may be assigned to one or more fragment length characteristics in a fragment length profile such that one or more fragment length characteristics may have equal or different weights or values within the fragment length profile. Fragment length characteristics include, but are not limited to shape of the distribution, segment amplitude, peak shape, the fragment count ratio for two or more segments, the height of helical phasing peaks, fragment count ratio at two different fragment lengths, ratio of fragment counts within two different fragment length ranges, the fragment length range within a segment, the ratio of maximum amplitudes for two or more segments, position of a peak or peaks, and fragment length distribution within a subset of reads. It is intended that ratios "between 2 or more segments" encompasses, but is not limited to, two or more segments from one nucleic acid library, two or more segments from two or more nucleic acid libraries, two or more segments of the same peak shape, two or more segments of different peak shapes, two or more segments from similar or different nucleic acid library types and two or more segments from similar or different subsets of reads from a nucleic acid library.

Distribution types include, but are not limited to, a single peak shape, a multiple peak shape, exponential or exponential-like distributions, distributions inflated for long or short fragments, flat or uniform distributions, complex distribution shapes and combinations thereof. Complex distribution may include aspects of at least 2, at least 3, at least 4, at least 5, at least 6, at least 7, at least 8 or more peak shapes. A single peak shape may occur around any fragment length including but not limited to around the 50 base pair fragment length. Long fragments may include fragment lengths greater than about 60 base pairs, about 65 base pairs, about 70 base pairs, about 75 base pairs, about 80 base pairs, about 85 base pairs, about 90 base pairs, about 95 base pairs, about 100 base pairs, about 150 base pairs, about 175 base pairs, about 200 base pairs, about 250 base pairs, about 300 base pairs, about 350 base pairs and about 400 base pairs. Short fragments may include fragment lengths shorter than about 500 bp, about 400 bp, about 300 bp, about 200 bp, about 100 bp, about 50 bp, about 40 bp, about 35 bp, about 30 bp, about 25, about 20 bp. Aspects of peak shape include but are not limited to the segment range, segment amplitude and the total number of reads within the segment, peak width, slope of the peak, derivative of the peak; aspects of peak shape may vary.

A single peak shape distribution may encompass a range of fragment lengths including but not limited to at least about 5 base pairs, at least about 10 base pairs, at least about 15 base pairs, at least about 20 base pairs, at least about 30 base pairs, at least about 35 base pairs, at least about 40 base pairs, or more than at least about a 45 base pair fragment length range within a segment. Fragment length range within a segment may vary. For example, the range of fragment length around a 50 base pair single peak distribution includes but is not limited to fragment lengths from 30 to 60 base pairs, 35 to 60 base pairs, 40 to 60 base pairs, and 45 to 55 base pairs.

Segment amplitude encompasses the abundance or relative abundance of reads for a fragment length within a defined segment. In some aspects the distribution amplitude may be the highest abundance or relative abundance within a defined fragment length range; distribution amplitude may also encompass the average highest abundance or relative abundance within a defined fragment length range. In some aspects of the application, a fragment length distribution or fragment length distribution profile is obtained for a subset of reads from a nucleic acid library. A subset of reads from a nucleic acid library is intended to encompass less than the full set of reads from a nucleic acid library. Subsets may reflect reads determined to be from a particular microbe type, from particular microbe species, host reads, maternal reads, fetal reads, organ donor reads, non-host reads, microbial cell-free nucleic acid reads, cell-free nucleic acid reads, microbial reads or any other group; alternatively, a subset of reads may reflect the full set of reads minus those from a particular microbe type, maternal read, fetal read or any other group. In some aspects of the application, a fragment length distribution is obtained for target nucleic acids. "Target nucleic acids" can be nucleic acid fragments derived from microbes, transplanted organ, tumor cells, cancer cells, host or non-host mitochondrial DNA, antibiotic resistance gene sequences, host genomic DNA, microbial sequences integrated into the host genome or any other sequence or sequences of interest in a nucleic acid library. A target sequence may have migrated from another site, such as a site of infection or donated organ.

In some cases, the target nucleic acid may make up only a very small portion of the entire sample, e.g., less than 0.1%, less than 0.01%, less than 0.001%, less than 0.0001%, less than 0.00001%, less than 0.000001%, less than 0.0000001% of the total nucleic acids in a sample. Often, the total nucleic acids in an original sample may vary. For example, total cell-free nucleic acids (e.g., DNA, mRNA, RNA) may be in a range of 0.01-10,000 ng/ml, e.g., (about 0.01, 0.1, 1, 5, 10, 20, 30, 40, 50, 80, 100, 1000, 5000, 10000 ng/ml). In some cases, the total concentration of cell-free nucleic acids in a sample is outside of this range (e.g., less than 0.01 ng/ml; in other cases, the total concentration is greater than 10,000 ng/ml). This may be the case with cell-free nucleic acid (e.g., DNA) samples that are predominantly made up of human DNA and/or RNA. In such samples, pathogen target nucleic acids may have scant presence compared to the human or host nucleic acids.

The length of target nucleic acids can vary. In some particular embodiments, the target nucleic acids are relatively short; in other embodiments, the targets are relatively long. In some particular embodiments, the target nucleic acids are shorter than 110 bp.

As used herein, "nucleic acid" refers to a polymer or oligomer of nucleotides and is generally synonymous with the term "polynucleotide" or "oligonucleotide." Nucleic acids may comprise, consist of, or consist essentially of a deoxyribonucleotide, a ribonucleotide, a deoxyribonucleotide analog, chemically modified canonical deoxyribonucleotides, ribonucleotides, and/or ribonucleotide analog, nucleic acids with modified backbones, or any combination thereof.

Nucleic acids may be any type of nucleic acid including but not limited to: double-stranded (ds) nucleic acids, single stranded (ss) nucleic acids, DNA, RNA, cDNA, mRNA, CRNA, tRNA, ribosomal RNA, dsDNA, ssDNA, miRNA, siRNA, short hairpin RNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating microbe or pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, bacterial nucleic acids, fungal nucleic acids, parasite nucleic acids, viral nucleic acids, cell-free bacterial nucleic acids, cell-free fungal nucleic acids, cell-free parasite nucleic acids, viral particle-associated nucleic acids, mitochondrial DNA, host nucleic acids, host cell-free nucleic acids, intercellular signal nucleic acids, exogenous nucleic acids, DNA enzymes, RNA enzymes, therapeutics nucleic acids, or any combination thereof. Nucleic acids may be nucleic acids derived from microbes or pathogens including but not limited to viruses, bacteria, fungi, parasites and any other microbe, particularly an infectious microbe or potentially infectious microbe. Nucleic acids may derive from archaea, bacteria, fungi, molds, eukaryotes, and/or viruses. In some embodiments, nucleic acids may be derived directly from the subject or host, as opposed to a microbe or pathogen.

As used herein, a "nucleic acid library" refers to a collection of nucleic acid fragments. The collection of nucleic acid fragments may be used, for example, for sequencing. A nucleic acid library may be prepared from an initial sample using a bias-corrected recovery method of generating a sequencing library or using a biased recovery method of generating a sequencing library enabling bias correction. As used herein "bias-corrected recovery" methods are methods with consistent fragment length production that generally recover sample nucleic acids fragments within a targeted length and GC range without appreciable length and GC bias, methods enabling bias correction, methods capable of accounting for the bias from a sample, and methods capable of accounting for a bias introduced by a process of the method of generating a nucleic acid library. Bias-corrected recovery methods may include but are not limited to adding a process control molecule, extracting, generating a library, sequencing, amplifying, and any combination thereof. Unbiased recovery methods include, but are not limited to those described in U.S. Provisional No. 62/770,181 and 62/644,357. Methods of generating a nucleic acid library from an initial sample without extracting the nucleic acids before starting the nucleic acid library generation process from the initial sample are provided. In some embodiments, substances that may decrease yield or inhibit generation of a nucleic acid library, themselves, may be extracted or removed, but the nucleic acids are not extracted from the initial sample before the nucleic acid library is generated. The method comprises, consists of, or consists essentially of adding one or more process control molecules to an initial sample and generating the nucleic acid library from the spiked initial sample. The method comprises, consists of, or consists essentially of generating the nucleic acid library from the spiked initial sample. Nucleic acid libraries may utilize single-stranded and/or double-stranded nucleic acids.

Methods of generating a nucleic acid library from a sample with extraction are also encompassed.

Process control molecules can be one or more of ID Spike(s), SPANKs, Sparks or GC Spike-in Panel, dephosphorylation control molecules, denaturation control molecules, and/or ligation control molecules. See for example Published U.S. Patent Application No. 2015-0133391 and Published U.S. Patent Application No. 2017-0016048, the full disclosures of each is incorporated herein by reference in its entirety for all purposes). In some embodiments, the initial sample comprises, consists of, or consists essentially of circulating donor nucleic acids (See, for example, US20150211070, which is incorporated by reference herein in its entirety, including any drawings).

As used herein, "denaturing" refers to a process in which biomolecules, such as proteins or nucleic acids, lose their native or higher order structure. Native and higher order structure may include, for example, without limitation, quaternary structure, tertiary structure, or secondary structure. For example, a double-stranded nucleic acid molecule can be denatured into two single-stranded molecules.

As used herein, the term "dephosphorylation" or "dephosphorylating" refers to removal of a phosphate, such as the 5'- and/or 3'-end phosphate, from a nucleic acid, such as e.g. DNA.

As used herein, "detect" refers to quantitative or qualitative detection, including, without limitation, detection by identifying the presence, absence, quantity, frequency, concentration, sequence, form, structure, origin, or amount of an analyte.

In some embodiments, attaching a 3'-end adapter to nucleic acids, for example, denatured or dephosphorylated nucleic acids, and/or attaching a 5'-end adapter comprises, consists of, or consists essentially of ligating with an enzyme comprising, consisting of, or consisting essentially of a ligase, e.g., a T4 DNA ligase, CircLigase™ II. In some embodiments, the ligase is a single-stranded ligase. In some embodiments, attaching a 3'-end adapter to nucleic acids, for example, denatured or dephosphorylated nucleic acids, and/or attaching a 5'-end adapter comprises, consists of, or consists essentially of utilizing template-switching reaction. In some embodiments, attaching a 3'-end adapter to nucleic acids, for example, denatured or dephosphorylated nucleic acids comprises, consists of, or consists essentially of extending with an enzyme comprising, consisting of, or consisting essentially of a polymerase, e.g., a TdT polymerase. In some embodiments, the method further comprises, consists of, or consists essentially of utilizing a DNA polymerase, e.g., Klenow fragment, SuperScript™ IV reverse transcriptase, SMART® MMLV Reverse Transcriptase, etc. to extend a primer hybridized to nucleic acids or adapted nucleic acids and to generate complementary strands. In some embodiments, a target nucleic acid may be attached to one or more adapters. In some embodiments, a target nucleic acid is attached to the same adapter or different adapters at both ends.

As used herein, "GC-bias" refers to differential performance, treatment, or recovery of nucleic acids of different GC content but having identical length.

As used herein, "GC-content" or "guanine-cytosine content" refer to the percentage of nitrogenous bases in a nucleic acid, such as a DNA or RNA molecule, that are either guanine or cytosine or their chemical modifications.

As used herein, "host" refers to an organism that harbors another organism. The latter is defined as "non-host" organism. For example, a human can be a host that harbors a microbe, pathogen or fetus, the microbe, pathogen or fetus being the non-host. Host nucleic acids or materials are derived from a host. Non-host nucleic acids or materials may derive from a non-host organism, from transplanted material or from a fetus or fetal material within a host.

As used herein, "microbe," "microbial," or "microorganism" refers to an organism, such as, for example, a microscopic or macroscopic organism, which may exist as a single cell or as a colony of cells, capsids, spores, filaments, or multicellular organisms. Microbes include all unicellular organisms and some multicellular organisms, such as, for example, those from archaea, bacteria, protozoa, nematodes, viruses and eukaryotes. Microbes are often pathogens responsible for disease, but may also exist in a non-pathogenic, symbiotic relationship with a host, such as a human. A "commensal microorganism" is intended to include microbes that exist in a non-pathogenic, symbiotic relationship with a host. A host organism may harbor multiple types of non-host organisms simultaneously. In co-infection a host organism harbors multiple types of non-host organisms. The multiple types of non-host organisms may include one or more pathogens, one or more commensal microorganisms, or at least one pathogen and at least one commensal microorganism. The methods of the current application may be used to distinguish between closely related microorganisms, distinguish between microbes present as a pathogen, a commensal microorganism, or as incidental but clinically unimportant microbes.

Microbes or pathogens may include archaea, bacteria, yeast, fungi, molds, protozoans, nematodes, eukaryotes, and/or viruses. Microbes or pathogens may also include DNA viruses, RNA viruses, culturable bacteria, additional fastidious and unculturable bacteria, mycobacteria, and eukaryotic pathogens (See, Bennett J. E., D., R., Blaser, M. J. Mandell, Douglas, and Bennett's Principles and Practice of Infectious Diseases; Saunders, Philadelphia, PA, 2014; and Netter's Infectious Disease, 1st Edition, edited by Elaine C. Jong, MD and Dennis L. Stevens, MD, PhD (2015)). Microbes or pathogens may also include any of the microbes set forth in ncbi.nlm.nih.gov/genome/microbes/or ncbi.nlm-.nih.gov/biosample/.

Examples of microbes are one or more of the species or strains from one or more of the following genera: Coniosporium, Hantavirus, Talaromyces, Machlomovirus, Betatetravirus, Raoultella, Aeromonas, Ephemerovirus, Empedobacter, Loa, Macluravirus, Stenotrophomonas, Alfamovirus, Rosavirus, Emmonsia, Aggregatibacter, Orthopneumovirus, Weeksella, Nairovirus, Salivirus, Weissella, Mosavirus, Gammapartitivirus, Strongyloides, Passerivirus, Erysipelatoclostridium, Bacillarnavirus, Iotatorquevirus, Taenia, Trypanosoma, Olsenella, Cladosporium, Rhizobium, Prevotella, Leclercia, Paracoccus, Ilarvirus, Lagovirus, Rasamsonia, Plasmodium, Acremonium, Chlamydia, Clonorchis, Vibrio, Bartonella, Nakazawaea, Franconibacter, Anisakis, Norovirus, Nocardia, Solobacterium, Parechovirus, Avenavirus, Orthohepevirus, Aphthovirus, Hepandensovirus, Microbacterium, Lichtheimia, Lomentospora, Achromobacter, Ipomovirus, Tsukamurella, Elizabethkingia, Hepevirus, Seadornavirus, Alternaria, Trueperella, Gammatorquevirus, Bifidobacterium, Chrysosporium, Thogotovirus, Curtovirus, Deltatorquevirus, Balamuthia, Mastrevirus, Bdellomicrovirus, Mupapillomavirus, Pseudozyma, Wickerhamiella, Aquamavirus, Alloscardovia, Thielavia, Idaeovirus, Henipavirus, Coxiella, Haemophilus, Gammacoronavirus, Negevirus, Brevibacterium, Peptoniphilus, Alphacarmotetravirus, Nosema, Trichovirus, Arenavirus, Thermomyces, Necator, Waikavirus, Blosnavirus, Jonesia, Tetraparvovirus, Emaravirus, Plectrovirus, Sclerodarnavirus, Toxocara, Umbravirus, Burkholderia, Chromobacterium, Paracoccidioides, Brugia, Eragrovirus, Macrococcus, Absidia, Colletotrichum, Inovirus, Phycomyces, Wickerhamomyces, Acidaminococcus, Moraxella, Rothia, Phlebovirus, Slackia, Purpureocillium, Betapapillomavirus, Tupavirus, Cryspovirus, Saksenaea, Erysipelothrix, Kobuvirus, Mimoreovirus, Echinococcus, Mannheimia, Bergeyella, Cyclospora, Xylanimonas, Leptospira, Finegoldia, Curvularia, Cryptosporidium, Babuvirus, Pecluvirus, Lambdatorquevirus, Pythium, Carlavirus, Entomobirnavirus, Kocuria, Anaplasma, Ampelovirus, Avihepatovirus, Nepovirus, Rhodococcus, Bordetella, Mischivirus, Scedosporium, Gardnerella, Maculavirus, Trichoderma, Aveparvovirus, Salmonella, Avastrovirus, Copiparvovirus, Trachipleistophora, Clostridioides, Nanovirus, Siccibacter, Leptotrichia, Citrivirus, Odoribacter, Sanguibacter, Novirhabdovirus, Acremonium, Hafnia, Chaetomium, Tenuivirus, Yokenella, Rubulavirus, Varicellovirus, Alphamesonivirus, Sicinivirus, Leuconostoc, Microvirus, Gallantivirus, Morbillivirus, Lolavirus, Pantoea, Hepatovirus, Nupapillomavirus, Metschnikowia, Barnavirus, Kytococcus, Tritimovirus, Tannerella, Respirovirus, Pneumocystis, Dirofilaria, Pediococcus, Lactococcus, Blastomyces, Dianthovirus, Actinobacillus, Teschovirus, Oscivirus, Begomovirus, Potyvirus, Byssochlamys, Alphacoronavirus, Molluscipoxvirus, Lymphocryptovirus, Sapelovirus, Parabacteroides, Pyrenochaeta, Listeria, Senecavirus, Brevidensovirus, Potexvirus, Parvimonas, Flavivirus, Recovirus, Toxoplasma, Yatapoxvirus, Opisthorchis, Trichuris, Cyphellophora, Morganella, Perhabdovirus, Micrococcus, Pequenovirus, Mastadenovirus, Anaeroglobus, Tropheryma, Dolosigranulum, Wolbachia, Lelliottia, Mycoplasma, Tobravirus, Shewanella, Paeniclostridium, Erythroparvovirus, Sutterella, Sporopachydermia, Narnavirus, Nyavirus, Francisella, Arthroderma, Epsilontorquevirus, Sigmavirus, Amdoparvovirus, Actinomyces, Alphapermutotetravirus, Cardiobacterium, Influenzavirus C, Orthopoxvirus, Poacevirus, Phialophora, Lactobacillus, Polyomavirus, Debaryomyces, Foveavirus, Bymovirus, Mycoflexivirus, Grimontia, Mucor, Rhytidhysteron, Quadrivirus, Thermoascus, Aureusvirus, Trichosporon, Myceliophthora, Dermacoccus, Dysgonomonas, Pseudoramibacter, Becurtovirus, Gordonia, Sapovirus, Orthobunyavirus, Spiromicrovirus, Pomovirus, Exophiala, Sneathia, Helicobacter, Photorhabdus, Mogibacterium, Betapartitivirus, Avibirnavirus, Ambidensovirus, Oleavirus, Orientia, Deltacoronavirus, Anulavirus, Trichomonasvirus, Budvicia, Geotrichum, Enamovirus, Lachnoclostridium, Schistosoma, Paecilomyces, Panicovirus, Rhizoctonia, Brevibacillus, Beauveria, Pestivirus, Tombusvirus, Cilevirus, Cokeromyces, Peptostreptococcus, Phanerochaete, Proteus, Idnoreovirus, Aspergillus, Pasteurella, Malassezia, Hanseniaspora, Endornavirus, Azospirillum, Velarivirus, Cystovirus, Avisivirus, Bacteroides, Picobirnavirus, Myroides, Circovirus, Arterivirus, Aquaparamyxovirus, Onchocerca, Cosavirus, Kluyveromyces, Fijivirus, Candida, Hepacivirus, Dermabacter, Ourmiavirus, Allexivirus, Enterobacter, Acidovorax, Bracorhabdovirus, Carmovirus, Pluralibacter, Coltivirus, Fonsecaea, Streptobacillus, Corynebacterium, Macrophomina, Marburgvirus, Comovirus, Fabavirus, Alphanodavirus, Cellulomonas, Enterobius, Catabacter, Moellerella, Nakaseomyces, Cucumovirus, Valsa, Deltapartitivirus, Plesiomonas, Pseudomonas, Torovirus, Cuevavirus, Hypovirus, Trichomonas, Influenzavirus D, Giardiavirus, Crinivirus, Tepovirus, Sakobuvirus, Cyberlindnera, Paenalcaligenes, Bafinivirus, Rymovirus, Pegivirus, Yarrowia, Treponema, Borreliella, Rubivirus, Aureobasidium, Angiostrongylus, Filobasidium, Photobacterium, Rhizopus, Orthoreovirus, Ustilago, Simplexvirus, Aquareovirus, Protoparvovirus, Propionibacterium, Sprivivirus, Hunnivirus, Apophysomyces, Meyerozyma, Alphapapillomavirus, Candida, Brucella, Gallivirus, Dinovernavirus, Anaerobiospirillum, Eubacterium, Tatlockia, Terrisporobacter, Quaranjavirus, Sobemovirus, Dicipivirus, Arcanobacterium, Macanavirus, Atopobium, Vesivirus, Lodderomyces, Dinornavirus, Betatorquevirus, Kerstersia, Aparavirus, Neisseria, Agrobacterium, Edwardsiella, Labyrnavirus, Totivirus, Actinomadura, Tobamovirus, Influenzavirus B, Mandarivirus, Anaerococcus, Kunsagivirus, Naegleria, Campylobacter, Veillonella, Yamadazyma, Filobasidiella, Oerskovia, Penicillium, Anncaliia, Leptosphaeria, Pneumovirus, Psychrobacter, Isavirus, Granulicatella, Torradovirus, Cladophialophora, Influenzavirus A, Ophiostoma, Aerococcus, Ureaplasma, Etatorquevirus, Bocaparvovirus, Megasphaera, Reptarenavirus, Comamonas, Capnocytophaga, Alphatorquevirus, Syncephalastrum, Wallemia, Betacoronavirus, Hyphopichia, Nocardiopsis, Legionella, Trichinella, Paraburkholderia, Mammarenavirus, Echinostoma, Sphingobacterium, Enterovirus, Methanobrevibacter, Ochroconis, Cheravirus, Pasivirus, Enterococcus, Mycoreovirus, Tospovirus, Betanodavirus, Phytoreovirus, Enterocytozoon, Ferlavirus, Stemphylium, Filifactor, Leishmaniavirus, Gemella, Bromovirus, Alloiococcus, Cunninghamella, Cronobacter, Oribacterium, Orbivirus, Chrysovirus, Cripavirus, Tatumella, Pandoraea, Ogataea, Dracunculus, Volvariella, Iflavirus, Benyvirus, Rhadinovirus, Histoplasma, Rahnella, Morococcus, Verticillium, Janibacter, Gyrovirus, Alphapartitivirus, Mycobacterium, Roseomonas, Varicosavirus, Chryseobacterium, Parapoxvirus, Rhizomucor, Aureimonas, Levivirus, Leishmania, Luteovirus, Cypovirus, Ochrobactrum, Microsporum, Piscihepevirus, Ceratocystis, Sporothrix, Vesiculovirus, Cupriavidus, Cryptococcus, Metapneumovirus, Alphanecrovirus, Eikenella, Brevundimonas, Escherichia, Leifsonia, Schizophyllum, Granulibacter, Gordonibacter, Lachancea, Madurella, Ophiovirus, Phellinus, Nebovirus, Acanthamoeba, Fusobacterium, Pichia, Verruconis, Ehrlichia, Tibrovirus, Higrevirus, Wohlfahrtiimonas, Rhinocladiella, Neorickettsia, Sadwavirus, Roseobacter, Sequivirus, Pannonibacter, Rotavirus, Turicella, Cardiovirus, Propionimicrobium, Furovirus, Naumovozyma, Closterovirus, Fluoribacter, Zeavirus, Clavispora, Megrivirus, Gammapapillomavirus, Rickettsia, Polemovirus, Corynespora, Encephalitozoon, Shimwellia, Fusarium, Yersinia, Capronia, Delftia, Victorivirus, Marafivirus, Kluyvera, Iteradensovirus, Isoptericola, Vitivirus, Roseolovirus, Conidiobolus, Abiotrophia, Babesia, Phoma, Sanguibacteroides, Staphylococcus, Rhodotorula, Zetatorquevirus, Hymenolepis, Fasciola, Cytorhabdovirus, Cardoreovirus, Memnoniella, Trichophyton, Mitovirus, Phaeoacremonium, Providencia, Lysinibacillus, Giardia, Oligella, Streptomyces, Paraclostridium, Ralstonia, Coccidioides, Brambyvirus, Biatriospora, Allolevivirus, Acinetobacter, Starmerella, Omegatetravirus, Porphyromonas, Avulavirus, Streptococcus, Arcobacter, Topocuvirus, Mamastrovirus, Ancylostoma, Bornavirus, Capillovirus, Alphavirus, Tymovirus, Nucleorhabdovirus, Diaporthe, Chlamydiamicrovirus, Turncurtovirus, Saccharomyces, Riemerella, Betanecrovirus, Clostridium, Mobiluncus, Cercospora, Marnavirus, Mortierella, Aquabirnavirus, Xanthomonas, Dependoparvovirus, Ebolavirus, Neofusicoccum, Borrelia, Leminorella, Klebsiella, Blastocystis, Alcaligenes, Citrobacter, Eggerthella, Cedecea, Serratia, Penstyldensovirus, Bacillus, Laribacter, Wuchereria, Hordeivirus, Cytomegalovirus, Actinomucor, Ascaris, Shigella, Vittaforma, Torulaspora, Kingella, Oryzavirus, Polerovirus, Tremovirus, Erbovirus, Entamoeba, Lyssavirus, Paenibacillus, Facklamia, Kappatorquevirus, Metarhizium, Stachybotrys, Okavirus, Botrexvirus, Thetatorquevirus, and Basidiobolus.

As used herein, infection stage or stage of infection refers to the invisible phase of infection, the symptomatic phase of an infection, the resolution phase of an infection, the treatment phase, a recurrent phase, a recrudescent phase, an acute phase or infection, a chronic phase or infection, a slow or latent phase or infection, a persistent infection, a disseminated infection stage, a primary phase, a secondary phase or a tertiary phase of infection. The invisible phase of an infection occurs prior to emergence of the symptoms or before the symptoms are noticed by the subject or others. Synonyms of "invisible phase" would include "pre-symptomatic infection stage", "nascent stage of an infection" and "early stage of infection". A commensal organism may persist in the invisible stage of infection. The symptomatic phase of an infection occurs when the subject or others notice the symptoms or clinical change such as for example fever, pain, rash, headache, aches, respiratory problems, etc. The resolution phase of an infection during which an infection resolves by itself or by administering a treatment. The treatment phase may be part of the resolution phase if a treatment is administered. A recurrent phase occurs if a subject experiences a recurrence of an infection in any of the above stages. A recrudescent phase occurs if the infection is not treated properly or sufficiently the first time and comes back. Chronic infection are a type of persistent infection that is eventually cleared. An acute phase or infection occurs suddenly such as Hepatitis. A slow or latent phase or infection is an infection that lasts for the rest of the life of the host. A persistent infection is an infection that lasts for long periods; persistent infections occur when the primary infection is not cleared by the host. Some microbes infect hosts with primary, secondary and tertiary phase infections; an example is infection by *Treponema pallidum*. An infection may stay at any of the above stages for an indefinite period of time without necessarily progressing to a different phase. A commensal or symbiotic microbe may remain in the invisible stage of infection indefinitely or may not infect.

A variety of host-microbe biological relationships or interactions are known in the art. Host-microbe biological interactions include but are not limited to commensalism, mutualism, amensalism, parasitism, symbiosis and competition. It is recognized that a microbe may exhibit one type of interaction with the host when it is localized to certain sites but may exhibit another type of interaction with the host when it is localized to another site within the host. For example a microbe may exist in a commensalistic relationship to the host on the skin of the host but could exist in a parasitic or competitive relationship internal to the host. As used herein, "pathogen" refers to a microorganism that causes, or can cause, or is suspected to cause disease.

As used herein, the phrase "spiked initial sample" refers to an initial sample to which process control molecules have been added prior to the start of generating a sequencing library.

The term "derived from" encompasses the terms "originated from," "obtained from," "obtainable from," and "created from," generally indicates that one specified material finds its origin in another specified material or has features that can be described with reference to the another specified material. For example, an initial sample may be derived from a raw biological sample.

In some embodiments, the initial sample comprises, consists of, or consists essentially of a solid or a body fluid such as blood, plasma, serum, cerebrospinal fluid, synovial fluid, bronchoalveolar lavage, urine, stool, saliva, abdominal fluid, ascites fluid, peritoneal lavage, gastric fluid, interstitial fluid, lymph fluid, bile, abscess fluid, tissue, amniotic fluid, meconium, sinus aspirate, lymph node, bone marrow, hair, nails, cheek swab, skin swab, urethral swab, cervical swab, nasopharyngeal swab, nasopharyngeal aspirate, vaginal swab, epithelial cells, semen, vaginal discharge, intercellular fluid, pericardial fluid, rectal swab, bone, skin tissue, soft tissue, tears, and/or a nasal sample. In some embodiments, the initial sample comprises, consists of, or consists essentially of plasma. In some embodiments, the initial sample comprises, consists of, or consists essentially of urine. In some embodiments, the initial sample comprises, consists of, or consists essentially of cerebrospinal fluid. In some embodiments, the initial sample is from a human subject.

In some embodiments, an initial sample can be made up of, in whole or in part, cells and/or tissue. The initial sample may be cell-free or cell-depleted. The initial cell-free sample may comprise, consist of, or consist essentially of nucleic acids that originated from a different site in the body, such as a site of pathogenic infection. In the case of blood, serum, lymph, or plasma, the cell-free sample or cell-depleted initial sample may contain "circulating" cell-free nucleic acids that originated at anatomic locations other than the site of bodily fluid collection of the fluid in question. In the case of urine, the cell-free nucleic acids may be cell-free nucleic acids that originated in a different site in the body. The cell-free samples or cell-depleted initial samples can be obtained by depleting or removing cells, cell fragments, or exosomes by a known technique such as by centrifugation or filtration.

As used herein, the term "invasive disease" refers to a disease based, in part, on the ability of particular pathogens to seriously compromise the health of certain infected subjects, as opposed to merely colonizing other infected subjects, either as a commensal or infection with no or minor symptoms. For example, certain microbes can locally colonize tissues without causing any health problems in some hosts, while, in other hosts, they may invade tissues to the point where they cause serious inflammation, tissue or organ damage, sepsis, cancer, and other serious health issues. Microbes may also colonize a subject who is asymptomatic at one time point, but at a later point develops serious symptoms when the microbe translocates and/or becomes "active."

As used herein, the term "cell-free" refers to the condition of the nucleic acid outside a cell, viral particle or virion as it appeared in the body immediately before the sample is obtained from the body. For example, circulating cell-free nucleic acids in a sample may have originated as cell-free nucleic acids circulating in the bloodstream of a subject. In contrast, nucleic acids that are extracted post-collection from an intact microorganism, such as a blood-borne pathogen, or removed post-collection from intact virions in a plasma sample, are generally not considered to be "cell-free."

The present application provides methods of determining a site of localization in a subject. Nucleic acids from microbes or microoganisms from different sites within a subject may exhibit different fragment length profiles. The fragment length profile of a nucleic acid library or a subset of the nucleic acid library containing microbial nucleic acids differs if the microbial infection is circulating rather than located at one or more sites of localization. Thus, comparing a fragment length profile to a reference fragment length profile of one or more source sites may predict a site of localization if the fragment length profile from the sample is similar to a reference fragment length profile from a source site. By "site of localization" is intended any source site within a subject where a microbe occurs, persists, survives or proliferates. Source sites include, but are not limited to the bloodstream, blood, deep tissue, such as but not limited to the kidneys, liver, stomach, bladder, digestive organs, nerve cells, lung, bone, brain, heart, heart lining, sinus, GI tract, spleen, skin, joint, ear, nose, and mouth. It is envisioned that a subject may have more than one site of localization for a particular microbe. It is further understood that some sites of localization for a particular microbe may not contribute to a disease state or condition. Rather, some sites of localization for a particular microbe may indicate a commensal relationship between the microbe and host, while other sites of localization for a particular microbe may indicate a parasitic or amensal relationship between the microbe and host. It is further recognized that the occurrence of multiple sites of localization for a particular microbe may indicate a systemic infection of the host. Additionally it is recognized that site of localization for a particular microbe or pathogen of interest may impact a decision to treat or not to treat and may impact selection of appropriate treatment options. For example and without being limited by mechanism a fungal pathogen localized to the skin may be treated differently than a fungal pathogen localized to the lung and a bacterial microbe localized to heart tissue including but not limited to the lining of the hear may be treated differently than a bacterial microbe localized to the blood or blood stream.

In some embodiments, an initial sample comprises, consists of, or consists essentially of circulating tumor or fetal nucleic acids. (See, for example, Analysis of serum or blood borne nucleic acids, such as circulating tumor or fetal nucleic acids, e.g., as described in U.S. Pat. Nos. 8,877,442 and 9,353,414, or in pathogen identification through, e.g., analysis of circulating microbial or viral nucleic acids, e.g., as described in Published U.S. Patent Application No. 2015-0133391 and Published U.S. Patent Application No. 2017-0016048, the full disclosures of each is incorporated herein by reference in its entirety for all purposes). In some embodiments, the initial sample comprises, consists of, or consists essentially of circulating donor nucleic acids (See, for example, US20150211070, which is incorporated by reference herein in its entirety, including any drawings).

An initial sample can be derived from any subject (e.g., a human subject, a non-human subject, etc.). The subject can be healthy. In some embodiments, the subject is a human patient having, suspected of having, or at risk of having, a disease or infection. In some embodiments, the disease or infection is pathogen-related.

A human subject can be a male or female. In some embodiments, the sample can be from a human embryo or a human fetus. In some embodiments, the human can be an infant, child, teenager, adult, or elderly person. In some embodiments, the subject is a female subject who is pregnant, suspected of being pregnant, or planning to become pregnant.

In some embodiments, the subject is a human subject who has undergone an organ transplant or who is planning to undergo organ transplant.

In some embodiments, the subject is a farm animal, a lab animal, or a domestic pet. In some embodiments, the animal can be an insect, a dog, a cat, a horse, a cow, a mouse, a rat, a pig, a fish, a bird, a chicken, or a monkey.

The subject can be an organism, such as a single-celled or multi-cellular organism. In some embodiments, the sample may be obtained from a plant, fungi, eubacteria, archeabacteria, protist, or any multicellular organism. The subject may be cultured cells, which may be primary cells or cells from an established cell line.

In some embodiments, the subject has a genetic disease or disorder, is affected by a genetic disease or disorder, or is at risk of having a genetic disease or disorder. A genetic disease or disorder can be linked to a genetic variation such as mutations, insertions, additions, deletions, translocations, point mutations, trinucleotide repeat disorders, single nucleotide polymorphisms (SNPs), or a combination of genetic variations.

In some aspects, the subject is healthy or asymptomatic, or exhibits mild or non-specific clinical symptoms. In some cases a subject may be infected or suspected of being infected by a particular pathogen. In other cases, the subject is suspected of having an infection of unknown origin. In some cases the subject has been exposed to a pathogen, or suspected to have been exposed to a pathogen such as by living conditions, by travel to a particular geographic region or by interaction or sexual interaction with an infected individual.

The initial sample can be from a subject who has a specific disease, condition, or infection, or is suspected of having (or at risk of having) a specific disease, condition, or infection. For example, the initial sample can be from a cancer patient, a patient suspected of having cancer or a patient at risk of having cancer. In some embodiments, the initial sample can be from a patient with an infection, a patient suspected of an infection, or a patient at risk of having an infection. In some embodiments, the initial sample is from a subject who has undergone, or will undergo, an organ transplant.

Primer extension reactions can be carried out with a DNA-dependent polymerase or an RNA-dependent polymerase or reverse transcriptase or a combination thereof. In some embodiments, the primer extension reaction can be carried out by a DNA or RNA polymerase having strand displacing activity. In some embodiments, the primer extension reaction is carried out by a DNA or RNA polymerase that has non-templated activity. In some other embodiments, the primer extension reaction can be carried out by a DNA or RNA polymerase having strand displacing activity and a DNA or RNA polymerase that has non-templated activity. In some embodiments, primer extension is carried out with a Klenow fragment.

Reference fragment length profiles are generally predetermined. Suitable reference fragment length profile or profiles may vary depending on the method, type of comparison or purpose of method. One skilled in the art would select an appropriate reference fragment length profile or profiles. Reference fragment length profiles may be obtained from a subject or cell exposed to a compound of interest, a subject or cell exposed to a similar compound, from a subject or cell similar to said subject, from a subject or cell hosting a known microbe, from a subject or cell previously determined to have an infection in a source site, or a subject or cell in any other condition of interest suitable for use as determined by one skilled in the art.

Subjects with a transplant are at risk for transplant rejection even when provided with therapies to reduce the risk of rejection. Transplant rejection and transplant rejection disorder are significant, often life-threatening, risks to subjects with a transplant. Many anti-rejection therapies suppress the immune system of the subject thus increasing the subject's risk of infection or disease. Therefore there is a need to balance the use and dose of anti-rejection therapies. The current application provides methods of monitoring transplant status in a subject with a transplant. The methods comprise the steps of generating a baseline fragment length profile for a target nucleic acid within the nucleic acid library or the whole nucleic acid library generated from a sample obtained from said subject or donor. Target nucleic acids of particular interest in monitoring transplant status include, but are not limited to, donor and recipient mitochondrial DNA (mtDNA). Methods of monitoring transplant status may further comprise evaluating abundance of mitochondrial DNA from the transplant. Monitoring transplant status encompass monitoring anything related to the status of a transplant including, but not limited to, host rejection of the transplant, host immune reaction to the transplant, host reaction to the transplant, transplant deterioration, transplant health, transplant vascularization, transplant oxygenation and transplant breakdown. A baseline fragment length profile may be generated from a donor and/or recipient sample obtained before transplant, upon transplant or after transplant. The methods further comprise the step of generating a second fragment length profile from a sample obtained from the subject and comparing the second fragment length profile to the baseline fragment length profile. If the second fragment length profile differs from the baseline fragment length profile then an increased amount of an anti-rejection therapy may be internally administered to the subject.

Methods and systems of the present disclosure can be implemented by way of one or more algorithms. An algorithm can be implemented by way of software upon execution by a central processing unit. The algorithm can, for example, facilitate the enrichment, sequencing and/or detection of pathogen or microbe or other target nucleic acids, or generation of a fragment length profile.

A compound may include, but is not limited to a chemotherapeutic agent, an antiviral agent, an antibiotic agent, an anti-fungal agent, an agent of interest, a small molecule, an experimental agent, a clinical trial compound, a medicine, drug, and active ingredient.

Toxicity includes but is not limited to cytotoxicity. It is further recognized that toxicity may occur preferentially in particular classes of cells including but not limited to cancer cells and pathogens.

The fragment length profiles and methods of the present application may be used in noninvasive prenatal testing (NIPT). The methods allow non-invasive monitoring, diagnosis and tracking of fetal condition.

In some embodiments, separating the adapted nucleic acids comprises, consists of, or consists essentially of immobilizing the adapted nucleic acids. In some embodiments, immobilization occurs on magnetic beads or functionalized magnetic beads. In some embodiments, immobilization occurs on a modified glass, modified capillary surfaces, and/or modified columns. In some embodiments, separating the adapted nucleic acids comprises, consists of, or consists essentially of purifying the adapted nucleic acids. In some embodiments, separating the adapted nucleic acids comprises, consists of, or consists essentially of precipitating the adapted nucleic acids. In some embodiments, separating the adapted nucleic acids comprises, consists of, or consists essentially of using a 3'-end protected 3'-end adapter. In some embodiments, separating the adapted nucleic acids comprises, consists of, or consists essentially of separating adapted nucleic acids from unadapted nucleic acids by digesting unadapted nucleic acids with a 3'end exonuclease, the adapted nucleic acids comprising, consisting of, or consisting essentially of a 3'-end protected 3'-end adapter. Some embodiments further comprise, consist of, or consist essentially of enriching nucleic acids for fragments of a certain length. In some embodiments, denaturation is used to further separate nucleic acids or target nucleic acids. In some embodiments, denaturation comprises, consists of, or consists essentially of selective denaturation. In some embodiments, selective denaturation comprises, consists of, or consists essentially of one or more denaturation steps effective for the selection of fragments of a certain length and/or GC-content. In some embodiments, separating for fragments of a certain length may occur through the use of proteinases, detergents, heparin, hemolysis and plasma concentration.

The methods provided herein include various non-invasive methods for subject's suffering from an infection, a subject at risk for contracting an infection, and/or for a subject experiencing undefined symptoms that are mimicking multiple other diseases. The methods provided herein can be applied for a variety of purposes such as to diagnose or detect an infection, to determine the infection stage, to predict the infecting stage of the microbe, to predict if the infection will progress to an invasive disease stage, to monitor the efficacy and/or response to a treatment or procedure, to stop the treatment, to determine the site of infection, to determine the site of colonization, or to modify, or optimize a therapy for a better clinical response. Consequently, the methods provided herein may reduce adverse effects caused by a misdiagnosis or by an invasive procedure such as a biopsy to determine if, what, and how an organ has been infected in the subject.

FIG. 1 provides a general overview of some of the methods provided herein. Often, the methods can comprise, obtaining a clinical sample from an infected subject or a subject at risk of having an infection; making a "spiked-sample" by adding the synthetic nucleic acids provided by the disclosure; optionally, extracting the nucleic acids from the spiked-sample; generating a spiked-sample library; optionally, enriching for a target nucleic acid of interest; conducting a detection assay, such as a sequencing assay to obtain sequence reads from the spiked-sample library; and determining a measurement from the detected nucleic acids, and comparing this measurement to a control or a reference to determine the infection stage, biological relationship between microbe and host, or site of localization (e.g., organ, or tissue type) in a subject. In some cases, the comparison of the absolute abundance for a target nucleic acid to a control or reference can indicate an infection stage or site of localization in the subject. In some cases, the comparison of the distribution of fragment lengths for the target nucleic acid to a control or reference can indicate the infection stage or site of localization in the subject. In some cases, the comparison of the absolute abundance and distribution of fragment lengths for a target nucleic acid to a control or reference can indicate the infection stage or site of localization in the subject.

Figure 2:
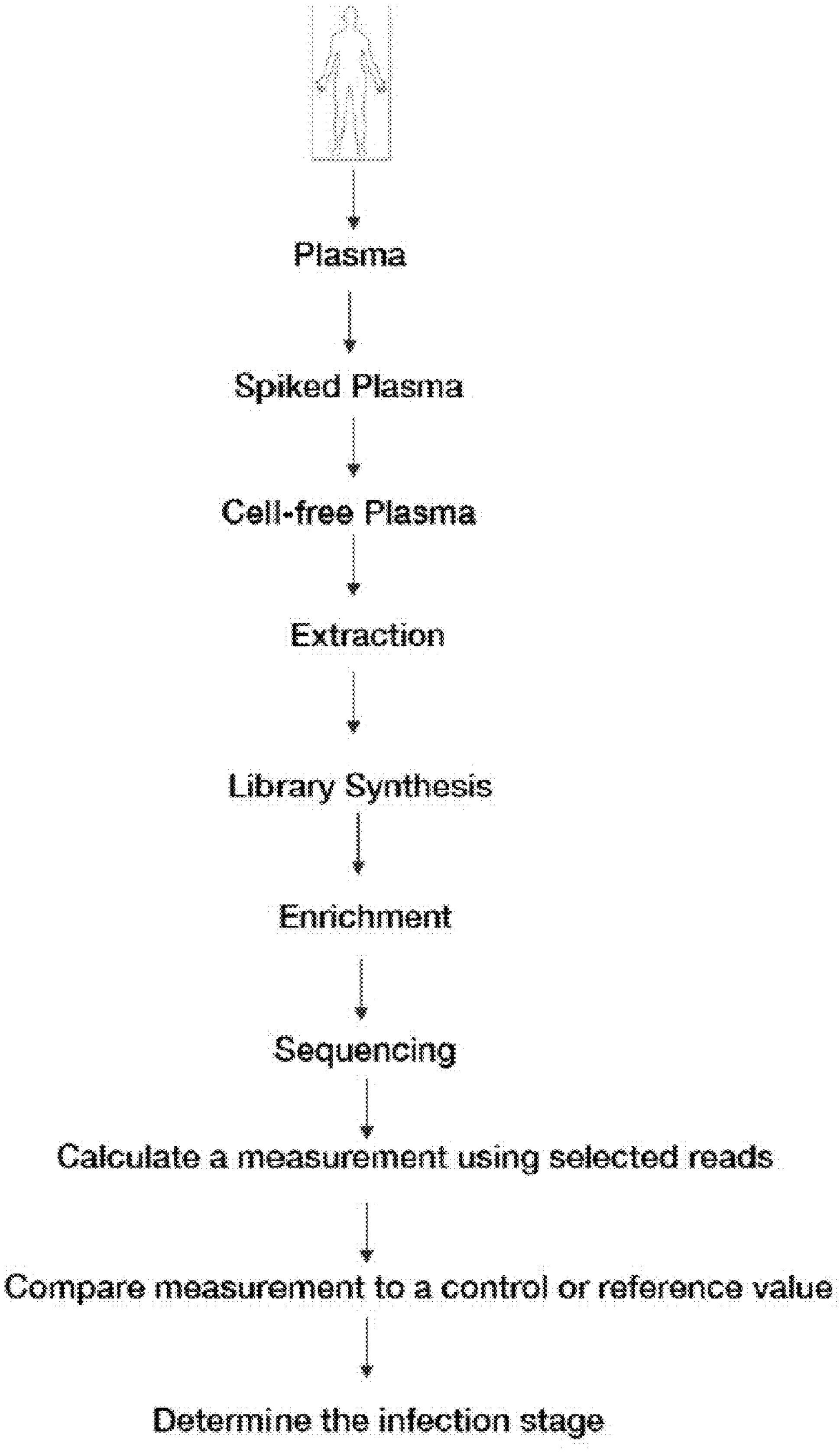
FIG. 2 depicts one of the cell-free methods of this disclosure.

The methods provided herein can be applied to any type of nucleic acid found in a clinical sample. FIG. 2 provides an overview of an example of a cell-free method. FIG. 17 provides a schematic of an exemplary infection in a subject. A source of a pathogen infection may be, for example in the lung or any other organ (e.g, brain, skin, heart tissue, stomach, liver, intestine). Cell-free nucleic acids, such as cell-free DNA, derived from the pathogen may travel through the bloodstream and can be collected in a plasma sample for analysis. Some of the cell-free methods provided herein can comprise obtaining a clinical sample from an infected subject or a subject at risk of having an infection; making a "spiked-sample" by adding the synthetic nucleic acids provided by the disclosure; isolating the cell-free nucleic acids, optionally, extracting the cell-free nucleic acids from the spiked-sample; generating a spiked-sample library; optionally, enriching for a target nucleic acid of interest; conducting a detection assay, such as a sequencing assay to obtain sequence reads from the spiked-sample library; and determining a measurement from the detected cell-free nucleic acids, and comparing this measurement to a control or a reference to determine the infection stage or site of localization in the subject.

Figure 4:
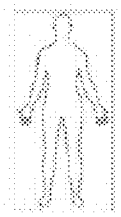
FIG. 4 depicts one of the infection site detection methods of this disclosure.

In some cases, the methods may be combined with a sequencing method to identify an organ or tissue that may be infected, or to rule out the possibility that an organ is infected in a subject (see, Koh W. et al, Noninvasive in vivo monitoring of tissue-specific global gene expression in humans, PNAS 2014:111 (7361-7366), which publication is hereby incorporated by reference in its entirety for all purposes). FIG. 4 provides an example of an organ-site method using cell-free RNA sequencing. An organ-site detection assay may be used in a case where the methods of the disclosure or another clinical test determines that the subject has an infection at the invasive disease stage. In this case, the method may further comprise conducting one of the organ-site methods provided herein to detect if an organ has been infected.

The present disclosure also provides methods for individualized treatment for an infected subject or a subject who is susceptible or at risk for infections (e.g., immunosuppressed, immunocompromised, living conditions, or genetic variations resulting in increased susceptibility for infection). Individualized treatment provided by the present disclosure includes methods of predicting if an infection will progress to an invasive disease stage, methods for monitoring the efficacy of a therapy in a subject, modifying a therapeutic regimen depending on the subject's response to the therapy, and determining the pathogen's resistance to a particular therapeutic or a subject's genetic predisposition for a response to a given therapeutic.

The nucleic acids produced according to the present methods may be analyzed to obtain various types of information including genomic, epigenetic (e.g., methylation), and RNA expression. Methylation analysis can be performed by, for example, conversion of methylated bases followed by DNA sequencing. RNA expression analysis can be performed, for example, by polynucleotide array hybridization, by RNA sequencing techniques, or by sequencing cDNA produced from RNA.

Sequencing may be by any method known in the art. Sequencing methods include, but are not limited to, Maxam-Gilbert sequencing-based techniques, chain-termination-based techniques, shotgun sequencing, bridge PCR sequencing, single-molecule real-time sequencing, ion semiconductor sequencing (e.g., Ion Torrent™ sequencing), nanopore sequencing, pyrosequencing (454), sequencing by synthesis, sequencing by ligation (SOLID sequencing), sequencing by electron microscopy, dideoxy sequencing reactions (Sanger method), massively parallel sequencing, polony sequencing, and DNA nanoball sequencing. The term "Next Generation Sequencing (NGS)" herein refers to sequencing methods that allow for massively parallel sequencing of nucleic acid molecules during which a plurality, e.g., millions, of nucleic acid fragments from a single sample or from multiple different samples are sequenced simultaneously. Non-limiting examples of NGS include sequencing-by-synthesis, sequencing-by-ligation, real-time sequencing, and nanopore sequencing. In some embodiments, sequencing involves hybridizing a primer to the template to form a template/primer duplex, contacting the duplex with a polymerase enzyme in the presence of detectably labeled or unlabeled nucleotides under conditions that permit the polymerase to add labeled or unlabeled nucleotides to the primer in a template-dependent manner, detecting a signal from the incorporated labeled nucleotide or detecting a signal resulting from the process of incorporating labeled or unlabeled nucleotide (e.g., proton release), and sequentially repeating the contacting and/or detecting steps at least once, wherein sequential detection of incorporated labeled or unlabeled nucleotide determines the sequence of the nucleic acid.

Exemplary detectable labels include radiolabels, fluorescent labels, protein labels, dye labels, enzymatic labels, etc. In some embodiments, the detectable label may be an optically detectable label, such as a fluorescent label. Exemplary fluorescent labels include cyanine, rhodamine, fluorescein, coumarin, BODIPY, Alexa Flour®, or conjugated multi-dyes.

In some embodiments, the sequencing comprises, consists of, or consists essentially of obtaining paired end reads. In some embodiments, the sequencing comprises, consists of, or consists essentially of obtaining consensus reads.

The accuracy or average accuracy of the sequence information may be greater than about 80%, about 90%, about 95%, about 99%, about 99.98%, or about 99.99%. The sequence accuracy or average accuracy may be greater than about 95% or about 99%. The sequence coverage may be greater than about 0.00001 fold, 0.0001 fold, 0.001 fold, about 0.01 fold, about 0.1 fold, about 0.5 fold, about 0.7 fold, or about 0.9 fold. The sequence coverage may be less than about 200,000 fold, about 100,000 fold, about 10,000 fold, about 1,000 fold, or about 500 fold.

In some embodiments, the sequence information obtained per nucleic acid template is more than about 10 base pairs, about 15 base pairs, about 20 base pairs, about 50 base pairs, about 100 base pairs, or about 200 base pairs. The sequence information may be obtained in less than 1 month, 2 weeks, 1 week, 2 days, 1 day, 14 hours, 10 hours, 3 hours, 1 hour, 30 minutes, 10 minutes, or 5 minutes.

Although the Examples (below) use specific sequences for certain sequencing systems, e.g., Illumina® sequencing systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent™ sequencing systems, Oxford Nanopore® sequencing systems, Genia Technologies™ sequencing systems, Pacific Biosciences® sequencing systems, Complete Genomics® sequencing systems, and the like.

The methods provided herein may include use of a system such as a system that contains a nucleic acid sequencer (e.g., DNA sequencer, RNA sequencer) for generating DNA or RNA sequence information. The system may include a computer comprising software that performs bioinformatic analysis on the DNA or RNA sequence information. Bioinformatic analysis can include, without limitation, assembling sequence data, detecting and quantifying genetic variants in a sample, including germline variants and somatic cell variants (e.g., a genetic variation associated with cancer or pre-cancerous condition, a genetic variation associated with infection).

Sequencing data may be used to determine genetic sequence information, ploidy states, the identity of one or more genetic variants, as well as a quantitative measure of the variants, including relative and absolute relative measures.

In some cases, sequencing of the genome involves whole genome sequencing or partial genome sequencing. The sequencing may be unbiased and may involve sequencing all or substantially all (e.g., greater than 70%, 80%, 90%) of the nucleic acids in a sample. Sequencing of the genome can be selective, e.g., directed to portions of the genome of interest. Sequencing of select genes, or portions of genes may suffice for the analysis desired. Polynucleotides mapping to specific loci in the genome that are the subject of interest can be isolated for sequencing by, for example, sequence capture or site-specific amplification.

Aligning Sequence Reads

Following sequencing, the dataset of sequences can be uploaded to a data processor for bioinformatics analysis to subtract host or host-related sequences, e.g., human, cat, dog, etc. from the analysis; and determine the presence and prevalence of pathogen or contaminant sequences (for example microbial sequences), for example by a comparison of the coverage of sequences mapping to a microbial reference sequence to coverage of the host reference sequence. The subtraction of host sequences may include the step of identifying a reference host sequence, and masking microbial sequences or microbial-mimicking sequences present in the reference host genome. Similarly, determining the presence of a microbial sequence by comparison to a microbial reference sequence may include the step of identifying a reference microbial sequence, and masking host sequences or host-mimicking sequences present in the reference microbial genome sequences.

The dataset can be optionally cleaned to check sequence quality, remove remnants of sequencer specific nucleotides (for example adapter sequences), and merge paired end reads that overlap to create a higher quality consensus sequence with less read errors. Duplicate sequences can be identified as those having identical start sites and length or identical or almost identical sequence. Optionally, duplicates may be removed from the analysis.

In some aspects, host or host-related (e.g., human) sequences can be subtracted from the analysis. In some aspects, host sequences are retained in the analysis. In some aspects, the amplification/sequencing steps can be unbiased and the preponderance of sequences in a sample will be host sequences. The subtraction process may be optimized in several ways to improve the speed and accuracy of the process, for example by performing multiple subtractions where the initial alignment is set at a coarse filter, e.g., with a fast aligner, and performing additional alignments with a fine filter such as a sensitive aligner or extended reference database.

The dataset of reads can be initially aligned against a host reference genome, including without limitation Genbank hg19 or Genbank hg38 reference sequences, to bioinformatically subtract the host DNA. Each sequence can be aligned with the best fit sequence in the host reference sequence. Sequences identified as host can be bioinformatically removed from the analysis.

The removal of host or host-related sequences can also be optimized by adding in contigs that have a high hit rate, including without limitation highly repetitive sequence present in the genome that are not well represented in reference databases. For example, it has been observed that of the reads that do not align to hg19 or hg38, a significant amount is eventually identified as human in a later stage of the pipeline, when a database that includes a large set of human sequences is used, for example the entire NCBI NT database. Removing these reads earlier in the analysis can be performed by building an expanded host or host-related reference. This reference can be created by identifying host contigs in a sequence database other than the reference, e.g., NCBI NT database, that have high coverage after the initial host read subtraction. Those contigs can be added to the host reference to create a more comprehensive reference set. Additionally, novel assembled host-related contigs from cohort studies can be used as a further reference to filter host-derived reads.

Regions of the host genome reference sequence that contain relevant non-host sequences may be masked, e.g., viral and bacterial sequences that are integrated into the genome of the reference sample.

Optionally, host or host-related sequences can be identified and removed by non-alignment based methods, such as identifying sequences by sequence characteristics including frequency of certain motifs, sequence patterns, word frequencies, or nucleotide biases.

Sequence reads identified as non-human can then be aligned to a nucleotide database of microbial reference sequences. The database may be selected for those microbial sequences known to be associated with the host, e.g., the set of human commensal and pathogenic microorganisms.

The microbial database may be optimized to mask or remove contaminating sequences. For example, many public database entries include artifactual sequences not derived from the microorganism, e.g., primer sequences, host sequences, and other contaminants. It may be desirable to perform an initial alignment or plurality of alignments on a database. Regions that show irregularities in read coverage when multiple samples are aligned can be masked or removed as an artifact. The detection of such irregular coverage can be done by various metrics, such as the ratio between coverage of a specific nucleotide and the average coverage of the entire contig within which this nucleotide is found. In general, a sequence that is represented as greater than about 5×, about 10×, about 25×, about 50×, about 100× the average coverage of that reference sequence can be artifactual. Alternatively, a binomial test can be applied to provide a per-base likelihood of coverage given the overall coverage of the contig. Removal of contaminant sequence from reference databases allows accurate identification of microbes.

Each high confidence read may align to multiple organisms in the given microbial database. To correctly assign organism abundance based upon this possible mapping redundancy, an algorithm can be used to compute the most likely organism (for example, see Lindner et al. Nucl. Acids Res. (2013) 41 (1): e10). For example, GRAMMy or GASiC algorithms can be used to compute the most likely organism that a given read came from.

Alignments and assignment to a host sequence or to a non-host (e.g., microbial) sequence may be performed in accordance with art-recognized methods. For example, a read of 50 nt. may be assigned as matching a given genome if there is not more than 1 mismatch, not more than 2 mismatches, not more than 3 mismatches, not more than 4 mismatches, not more than 5 mismatches, etc. over the length of the read. Publically available algorithms may be used for alignments and identification. A non-limiting example of such an alignment algorithm is the bowtie2 program (Johns Hopkins University).

These assignments of reads to an organism (e.g., host organism, non-host organism, microbe, pathogen, etc.) can then totaled and used to compute the estimated number of reads assigned to each organism in a given sample, in a determination of the prevalence of the organism in the sample (for example, a cell-free nucleic acid sample). This information can be used to determine an origin of a pathogen or contaminant. The analysis can normalize the counts for the size of the microbial genome to provide a calculation of coverage for the microbe. The normalized coverage for each microbe can be compared to the host sequence coverage in the same sample to account for differences in sequencing depth between samples.

Further, a dataset of microbial organisms represented by sequences in the sample, and the prevalence of those microorganisms can be optionally aggregated and displayed for ready visualization, e.g., in the form of a report.

The present disclosure provides normalization methods. In some cases, the methods of the present disclosure may comprise one or more normalization methods. The normalization methods provided by the present disclosure allow for efficient and improved measurements or amounts of disease-specific, pathogen-specific, or organ-specific nucleic acids detected in a sample.

The normalization methods of the present disclosure generally use spike-in synthetic nucleic acids. The spike-in synthetic nucleic acids may be used to normalize the sample in a number of different ways. The spike-in nucleic acids may normalize across all samples and all methods of measuring disease-specific nucleic acids, pathogen-specific nucleic acids or other target nucleic acids. In some cases, the spike-ins may be used to increase the precision of a relative abundance calculation of a pathogen nucleic acid (or disease-specific nucleic acid or target nucleic acid) in a sample compared to other pathogen nucleic acids in the sample.

In general, a known concentration (or concentrations) of species of synthetic nucleic acids may be spiked into each sample. In many cases, the species of synthetic nucleic acids can be spiked in at equimolar concentration of each species. In some cases, the concentrations of the species of synthetic nucleic acids can be different.

The abundance of the nucleic acid species may be altered due to the inherent biases of the sample handling, preparation, and measurement (e.g., detection). After measurement, the efficiency of recovering nucleic acids of each length can be determined by comparing the measured abundance of each "species" of spiked nucleic acid to the amount spiked in originally. This can yield a "length-based recovery profile".

The "length-based recovery profile" may be used to normalize the abundance of all (or most, or some) disease-specific nucleic acids, pathogen nucleic acids, or other target nucleic acids by normalizing the disease-specific nucleic acid abundances (or the abundances of the pathogen nucleic acids or other target nucleic acids) to the spiked molecule of the closest length, or to a function fitted to the spiked molecules of different lengths.

This process may be applied to target nucleic acids such as the pathogen-specific nucleic acids, and may result in an estimate of the "original length distribution of all pathogen-specific nucleic acids" at the time of spiking the sample. The "original length distribution of all target nucleic acids" may show the length distribution profile for the target nucleic acids (e.g., pathogen-specific nucleic acids or organ-specific nucleic acids) at the time of spiking the sample. It is this length distribution that the spiked nucleic acids can seek to recapitulate in order to achieve perfect or near-perfect abundance normalization. It is this length distribution that the spiked nucleic acids can seek to recapitulate in order to achieve determine endogenous fragment length distribution of target nucleic acids.

As it may not be possible to spike a sample with a mixture of known nucleic acids that exactly recapitulates the relative abundance profile of disease-specific nucleic acids, pathogen nucleic acids, or other target nucleic acids in that specific sample, in part because the sample may have been used up or time may have changed the relative abundance profile, each "species" of spike-in can be weighted in proportion to its relative abundance within the "original length distribution of all disease-specific nucleic acids". The sum of all "weighting factors" can equal 1.0.

Normalization can involve a single step or a series of steps. In some cases, the abundance of disease-specific nucleic acids (or pathogen nucleic acids or other target nucleic acids) may be normalized using the raw measurement of the closest sized spiked nucleic acid abundance to yield the "Normalized disease-specific nucleic acid (or pathogen nucleic acids or other target nucleic acid) abundance". Then, the "Normalized disease-specific nucleic acid abundance" (or pathogen nucleic acids or other target nucleic acid abundance) may be multiplied by the "weighting factor" to adjust for the relative importance of recovering that length, yielding the "Weighted normalized disease-specific (or pathogen-specific or other target) nucleic acid abundance". One advantage of this method of normalization may be that it allows comparable measurements of target nucleic acid (e.g., disease-specific nucleic acid, pathogen nucleic acid) abundance across all (or most) methods of measuring disease-specific nucleic acid abundance, regardless of method.

Such assays may involve measuring the amount of target nucleic acids (e.g., disease-specific nucleic acids) in biological samples (e.g., plasma) to detect the presence of a pathogen or identify disease states or to determine if a target nucleic acid is sample based, reagent based, or environmental based. The methods described herein can make these measurements comparable across samples, times of measurement, methods of nucleic acid extraction, methods of nucleic acid manipulation, methods of nucleic acid measurement, and/or a variety of sample handling conditions.

The present disclosure provides a diversity loss value measurement. In some cases, the methods of the present disclosure may comprise determining a diversity loss value.

Figure 5:
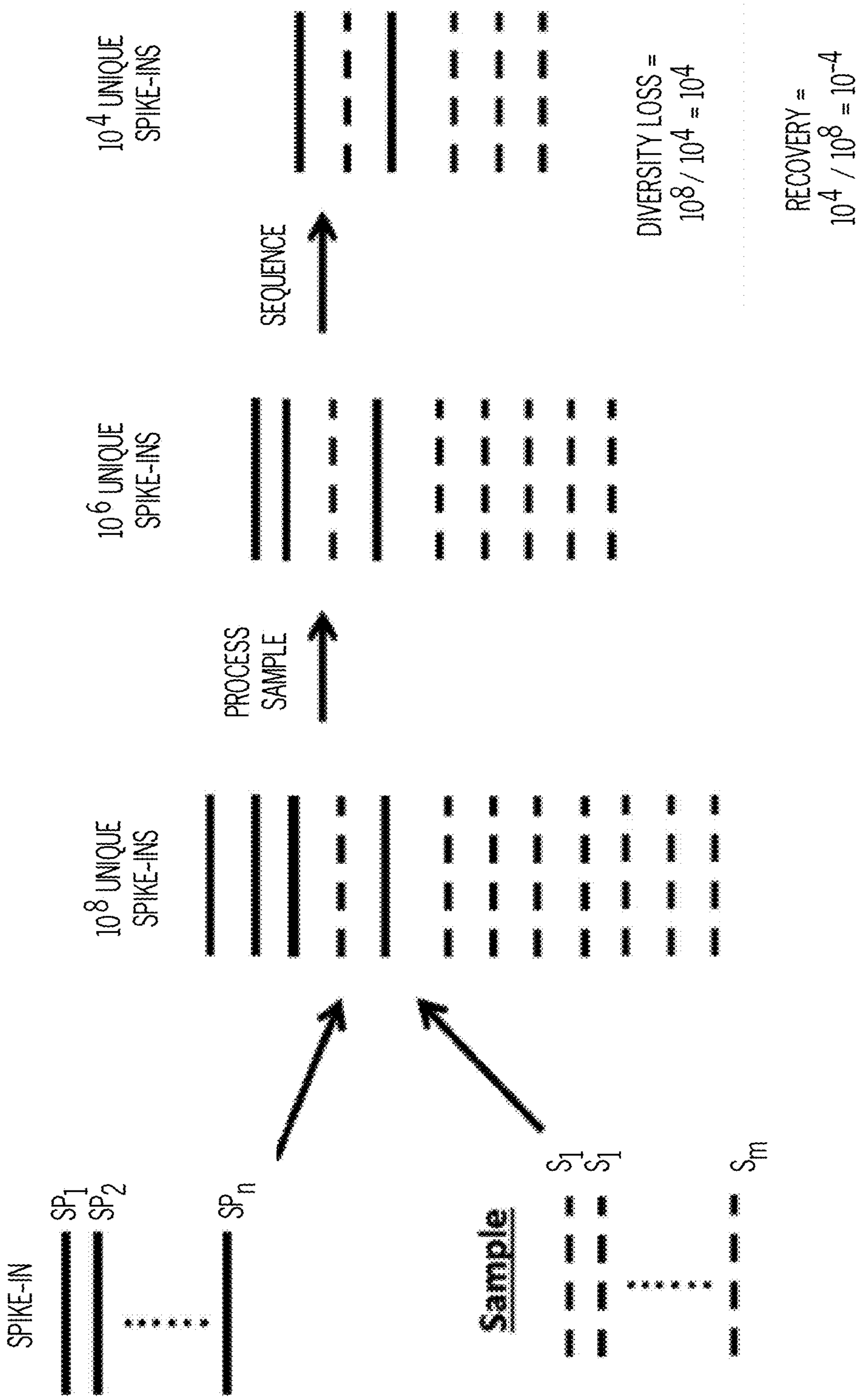
FIG. 5 depicts a general scheme of a method for determining diversity loss value.

The number of deduplicated (e.g., removed replicates) SPANK molecules detected in a particular library is a proxy for the minimum concentration detectable in that library. This can be useful for setting a threshold based on minimum concentration of the SPANK molecules detectable in that library. The threshold can be useful to ensure sufficient sequencing depth for detection of pathogen. The threshold can also be useful in making sure that pathogen signal was not due to cross contamination from other samples. For example, enrichment of pathogens relative to the threshold set by the SPANK molecules can be compared between different samples. More generally, it is proportional to the efficiency with which that library converted DNA molecules in the original sample to reads in the DNA sequencing data The spiked-in SPANK molecules provided by the disclosure may be used to calculate the diversity loss value. A diversity loss value may be determined as shown in FIG. 5. In some cases, if the diversity of the SPANK sequences is high enough, the SPANK sequences spiked into a sample can be assumed to be essentially all unique. Therefore, any duplicate SPANK sequences that are sequenced are likely due to PCR amplification and not due to multiple copies of the same SPANK sequence being added into the sample and can be removed from the analysis. In addition, if each SPANK sequence is unique, the total number of SPANK sequences originally added to a sample is known based on the nucleic acid concentration and volume added to the sample, and the total number of unique SPANK sequencing reads after sequencing is known; together these values can be used to calculate a diversity loss value.

C. Absolute Abundance (MPM)

The present disclosure provides an absolute abundance measurement (also referred to as "molecules per microliter" (MPMs)).

Generally, the absolute abundance of a target nucleic acid in a sample (e.g., DNA or RNA), may be determined by normalizing the number of sequence reads of a target nucleic acid with the empirically determined diversity loss value.

In some cases, an absolute abundance measurement may comprise spiking the sample with nucleic acids of various lengths or a single length and at known concentrations. In some cases, the fraction of information from the sample that is actually observed in the sequencing data can be observed for each spike-in length (e.g., by comparing observed reads with reads associated with the spiked nucleic acids, or by dividing the observed reads by the spike reads). The original numbers of non-host or pathogen molecules at each length can be back-calculated as well (e.g., inferred in part from the number of spike-in reads at each length). This load can be converted into a "molecules per microliter" measurement.

In many cases, the methods for detecting molecules per microliter (as well as other methods provided herein) may involve removal or sequestration of low-quality reads. Removal of low-quality reads may improve the accuracy and reliability of the methods provided herein. In some cases, the method may comprise removal or sequestration of (in any combination): un-mappable reads, reads resulting from PCR duplicates, low-quality reads, adapter dimer reads, sequencing adapter reads, non-unique mapped reads, and/or reads mapping to an uninformative sequence.

In some cases, the sequence reads can be mapped to a reference genome, and the reads not mapped to such reference genome can be mapped to the target or pathogen genome or genomes. The reads, in some instances, may be mapped to a human reference genome (e.g., hg19), while remaining reads are mapped to a curated reference database of viral, bacterial, fungal, and other eukaryotic pathogens (e.g., fungi, protozoa, parasites).

The present disclosure provides various control and references, which may be used to determine if a measurement provided by the present disclosure indicates that the subject has an infection at a certain infection stage or at a site of localization.

Often, the methods comprise processing a reference or a control using the methods of the present disclosure. In some cases, the control or reference values may be measured as a concentration or as a number of sequencing reads. The level may be a qualitative or a quantitative level. Based on sequence reads from the control or reference samples, a baseline level of the target nucleic acid (e.g., pathogen species, genetic variants, contaminants introduced from the laboratory environment, or organ-derived) may be determined.

In some cases, the control or reference values may be pathogen-dependent. For example, a control value for *H. pylori* may be different than a control value for *Clostridium difficile*. A database of levels or control values may be generated based on samples obtained from one or more subjects, for one or more pathogens, and/or for one or more time points. Such a database may be curated or proprietary.

In some cases, the control or reference value is a predetermined absolute value indicating the presence or absence of the cell-free pathogen nucleic acids or cell-free organ-derived nucleic acids. The control or reference value may be a value obtained by analyzing cell-free nucleic acid levels of a subject without an infection. In some cases, the control or reference value may be a positive control value and may be obtained by analyzing cell-free nucleic acids from a subject with a particular known infection, or with a particular known infection of a specific organ.

In some cases, a control can include identification of a set of commensal microorganisms or natural microflora that are or are not causative of an infection using control samples from healthy individuals. A threshold can be set based on the set of commensal microorganisms in control samples.

A Poisson model or other statistical model may be used to determine whether the determined baseline level of the clinical sample is significantly higher than reference control. Where the sequence reads from a clinical sample is significantly higher than the reference control this indicates that the read is informative. In some cases, such informative reads can be selected for determining a threshold for two different clinical groups.

Depending on the target nucleic acid and the level of background observed across the samples it may be desirable to subtract or filter out sequence reads using one or more references. Filtering can be done in combination with selecting, and before or after selecting. In some embodiments, the at least one reference value is based on levels of the pathogen nucleic acids detected in one or more samples selected from the group consisting of water sample, blood sample, plasma sample, serum sample, urine sample, body fluid sample, reagent sample, sample from a healthy subject or any combination thereof.

The control value may be a level of cell-free pathogen or cell-free organ-specific nucleic acids obtained from the subject at a different time point.

In some cases, a sample may be taken at a time point prior to a later test time point (e.g., after therapeutic intervention, or after a certain time has lapsed for watchful waiting). In such cases, comparison of the level at different time points may indicate the presence of infection, presence of infection in a particular organ, improved infection, or worsening infection. For example, an increase of pathogen or organ-specific cell-free nucleic acids by a certain amount over time may indicate the presence of infection or of a worsening infection, e.g., an increase of at least 5%, 10%, 20%, 25%, 30%, 50%, 75%, 100%, 200%, 300%, or 400% compared to an original value may indicate the presence of infection, or of a worsening infection. In other examples, a reduction of pathogen or organ-specific cell-free nucleic acids by at least 5%, 10%, 20%, 25%, 30%, 50%, 75%, 100%, 200%, 300%, or 400% compared to an original value may indicate the absence of infection, or of an improved infection (e.g., eradication of an infection).

Samples may be taken over a particular time period, such as every day, every other day, weekly, every other week, monthly, or every other month. For example, an increase of pathogen or organ cell-free nucleic acids of at least 50% over a week may indicate the presence of infection.

The methods may comprise determining a threshold value or range of values. A threshold can be used to identify samples that are in a certain clinical group (colonized stage vs. invasive disease stage or no organ infection vs. infected organ). A threshold can be used to identify or select sequence reads that are informative from a clinical sample. Generally, a desirable threshold will be one that maximizes the number of true positives, while minimizing the number of false positives. In some cases, the threshold may be selected using a ROC curve analysis. In some cases, the threshold may be selected based on performance metrics.

Threshold Selection

A threshold may be selected based on its performance by using various statistical methods such as, Receiver Operating Characteristic (ROC) curve analysis. ROC analysis may be used to assess the performance of the classifier over its entire operating range before selecting a cut-off threshold value. To determine which threshold cut-off should performs the best using a ROC curve one can move the threshold progressively across the range (e.g., from 0 to 1.0) to find a cut-off the results in decreasing the number of false positives and increasing the number of true positives.

ROC analysis may be conducted by plotting the data obtained from the methods of the present disclosure as follows: TP (sensitivity) against FP (1—specificity). Using the ROC graph, a perfect or near perfect classifier will generally go straight up the Y-axis and then along the X-axis, while a classifier with no power to classify the samples in different clinical groups will generally sit on the diagonal. Most classifiers will fall somewhere in between these two extreme cases and user can pick a threshold based on its best possible or desired performance.

Performance metrics such as accuracy, sensitivity, specificity, positive predictive value, or negative predictive value can be used to select a threshold. In some cases, one performance metric can be used to select a threshold. In some cases, multiple performance metrics can be used to select a threshold.

Any threshold applied to a dataset (in which PP is the positive population and NP is the negative population) is going to produce true positives (TP), false positives (FP), true negatives (TN) and false negatives (FN).

In some cases, the accuracy performance metric can be used to determine the probability of a correct classification. Accuracy may be calculated by applying the following equation: (TP+TN)/(PP+NP). In some cases, the accuracy is calculated using a trained algorithm.

In some cases, the sensitivity performance metric can be used to determine the ability of the test to detect disease in a population of diseased individuals. The percent sensitivity may be calculated by applying the following equation: TP/(TP+FN).

In some cases, the specificity performance metric can be used to determine the ability of the test to correctly rule out the disease in a disease-free population. Specificity may be calculated by applying the following equation: TN/(TN+FP).

When classifying a sample for diagnosis of infection, there are typically four possible outcomes from a binary classifier. If the outcome from a prediction is p and the actual value is also p, then it is called a true positive (TP); however, if the actual value is n then it is said to be a false positive (FP). Conversely, a true negative has occurred when both the prediction outcome and the actual value are n, and false negative is when the prediction outcome is n while the actual value is p. For a test that detect a disease or disorder such an infection, a false positive in this case may occur when the subject tests positive, but actually does not have the infection. A false negative, on the other hand, may occur when the subject actually does have an infection but tests negative for such infection.

The positive predictive value (PPV), or precision rate, or post-test probability of disease, is the proportion of patients with positive test results who are correctly diagnosed. It may be calculated by applying the following equation: PPV=TP/(TP+FP)×100. The PPV may reflect the probability that a positive test reflects the underlying condition being tested for. Its value does however may depend on the prevalence of the disease, which may vary.

The Negative Predictive Value (NPV) can be calculated by the following equation: TN/(TN+FN)×100. The negative predictive value may be the proportion of patients with negative test results who are correctly diagnosed. PPV and NPV measurements can be derived using appropriate disease prevalence estimates.

A threshold value may be set based on the user's desired performance in specificity and sensitivity to distinguish between the two clinical groups. In some cases, a method provided by the disclosure may have a specificity greater than 70%, 75%, 80%, 85%, 86%, 87%, 88%, 89%, 90%, 91%, 92%, 93%, 94%, 95%, 96%, 97%, 98%, 99%, or 99.5%, and a sensitivity greater than 95%, 95.5%, 96%, 96.5%, 97%, 97.5%, 98%, 98.5%, 99%, 99.5% or more.

Applications

The methods provided by the disclosure can be applied for a variety of purposes, such as to diagnose or detect an infection, to determine the biological relationship between a microbe and a host, infection stage of an infection, to predict if the infection will progress to an invasive disease stage, to monitor the efficacy and response to a treatment for infection, to modify or optimize a therapy for a better clinical response, to stop a treatment or therapy. Thus, using the methods provided by the disclosure one can provide individualized treatment to a subject that is tailored according to the data obtained by the methods.

Pathogens that are causing infection in a subject are expected to have several characteristics such as, but not limited to, elevated absolute abundance levels, abnormal nucleic acid length distribution profiles compared to an asymptomatic reference or a control, or they may have both characteristics. Likewise, pathogens that are infecting a subject's organ are expected to have elevated absolute abundance levels, abnormal nucleic acid length distribution profiles compared to an asymtomatic reference or a control, or they may have both characteristics. Pathogens that are causing infection in a subject can have several characteristics such as, but not limited to nucleic acid length distribution profiles comparable to a symptomatic reference or a control.

A. Infection Stage

The methods provided by present disclosure may be used to detect, diagnose, treat, monitor, predict, or prognose the infection stage in a subject. The pathogen causing the infection may be a bacterium, virus, fungus, parasite, yeast, or other microbe, particularly an infectious microbe. In some cases, the methods can be used to determine if the subject is in the colonization or invasive disease stage. In some cases, the methods can be used to detect if the subject is in the incubation stage, a prodromal stage, an illness stage, a decline stage, a convalescence stage, an eradication stage, chronic stage, or an invasive stage. In some cases, a method determines if an infection is active or latent stage.

The methods of the disclosure may be used in conjunction with other medical tests. For example, the methods can be used before or after a stool antigen test, urea breath test, serology, urease testing, histology, bacterial culture and sensitivity testing, biopsy, or endoscopy is taken from a subject. In some cases, the method described herein is conducted without conducting a stool antigen test, urea breath test, serology, urease testing, histology, bacterial culture and sensitivity testing, biopsy, or endoscopy on the subject.

In some cases of a method described herein, the method reduces the risk of an infection progressing to invasive disease stage by at least 10%, at least 20%, at least 30%, at least 40%, at least 50%, at least 60%, at least 70%, at least 80%, or at least 90%. In some cases of a method described herein, the method reduces the risk of mortality and/or morbidity related to complications in the invasive disease stage by at least 10%, at least 20%, at least 30%, at least 40%, at least 50%, at least 60%, at least 70%, at least 80%, or at least 90%.

Figure 3:
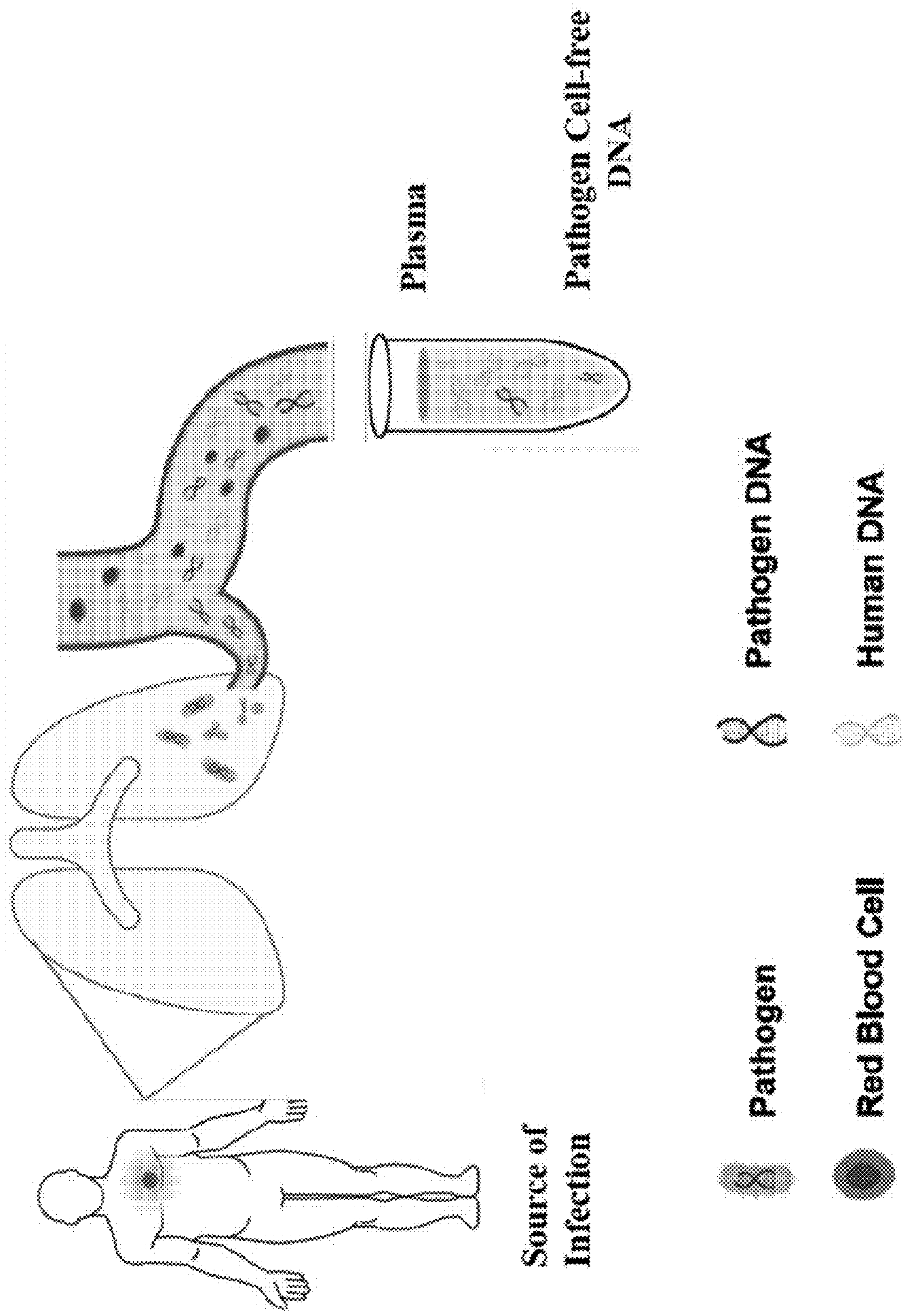
FIG. 3 shows a schematic of an exemplary infection.

The methods described herein may further comprise RNA sequencing (RNA-Seq) of cell free nucleic acids derived from the subject's organ. Tissue damage caused by an infection may lead to release of cell-free nucleic acids from the infected organ or tissue into the blood. FIG. 3 depicts an example for the release of cell-free DNA. An increase of e.g. cell-free RNA derived from an organ in a sample may indicate that the subject's organ has been infected by a pathogen.

For example, a method may comprise analyzing circulating cell-free pathogen nucleic acids from a pathogen associated with one or more clinical symptoms. The method may further comprise conducting an RNA-Seq to detect an increase in organ derived cell-free RNA in the subject's blood. The combination of these test results may indicate that the pathogen has infected the subject, as well as determine which organ is infected in the subject.

The RNA-Seq test may be conducted contemporaneously with another clinical method to detect an infection, subsequent to a clinical method to detect an infection, or prior to a clinical method detect and infection. In other cases, RNA-Seq may be used independently to investigate organ health or may provide increased confidence that an infection detected by another clinical method described herein is an infection of a particular organ.

In some cases, an RNA-Seq test may be able to determine if an infection is at an invasive disease stage. In some cases, the RNA sequencing test may be repeated over time to determine whether the infection is worsening or improving in a particular organ or tissue, or whether it is spreading to different organ or tissue in the subject. Likewise, the pathogen detection assay provided herein may also be repeated over time in conjunction with the organ infection assay.

An RNA-Seq test (or series of RNA-Seq tests) may sometimes be performed after a method described herein produces a positive test result (e.g., detection of a pathogen infection). The RNA-Seq test may be especially useful for confirming the infection or for identifying the location of the infection. For example, the methods may detect the presence of a pathogen in a subject by analyzing circulating cell-free nucleic acids, but the site of infection may be unclear. In such case, the method may further comprise sequencing cell-free RNA from the subject to confirm that the infection is within an organ.

Absolute Abundance of Organ-Specific RNA

In some cases, an absolute abundance level of organ-specific RNA sequences can be used as an indicator that an organ in the subject is infected by a pathogen. The detection of an organ infection may involve comparing a level of organ-specific nucleic acids with a control or reference value to determine the presence or absence of the organ nucleic acids and/or the quantity of organ-specific nucleic acids. The level may be a qualitative or a quantitative level.

In some cases, the control or reference value is a predetermined absolute value indicating the presence or absence of the cell-free organ-derived nucleic acids. For example, detecting a level of cell-free pathogen nucleic acids above the control value may indicate the presence of an infection in an organ, while a level below the control value may indicate the absence of an infection in an organ.

The control value may be a value obtained by analyzing cell-free nucleic acid levels of a subject without an infection (e.g., a healthy control). In some cases, the control value may be a positive control value obtained by analyzing cell-free nucleic acids from a subject with a particular infection, or with a particular infection of a specific organ.

The control or reference values may be measured as a concentration or as a number of sequencing reads. Control or reference values may be pathogen-dependent, organ-dependent or both pathogen-dependent and organ-dependent. A database of levels or control values may be generated based on samples obtained from one or more subjects, for one or more pathogens, and/or for one or more time points. Such a database may be curated or proprietary.

In some embodiments, the control or reference absolute abundance value indicates the presence or absence of a site of localization in a subject. For example, detecting an absolute abundance level of cell-free pathogen nucleic acids above the control or reference value may indicate that the infection is in an organ, while an absolute abundance value below the control or reference value may indicate that the infection is not in an organ. In some cases, detecting an absolute abundance level of cell-free pathogen nucleic acids above the control or reference value may indicate that the infection is in an organ, while an absolute abundance value below the control or reference value may indicate that the infection is not in an organ.

Distribution of Fragment Lengths of Organ-Specific RNA

In some cases, the distribution of fragment lengths of organ-specific RNA sequences indicates that an organ in a subject is infected by a pathogen.

For example, detecting an abnormal distribution of cell-free organ-specific nucleic acids may indicate that the organ is infected, while a normal distribution of cell-free organ-specific nucleic acids may indicate that the organ is not infected.

The control fragment length distribution may be predetermined by analyzing cell-free nucleic acid levels of a subject without an infection in an organ (e.g., a healthy control). The control fragment length distribution may be obtained in parallel by analyzing cell-free nucleic acid levels in a subject having an organ infection that are not associated with the infection.

In some embodiments, the control or reference distribution of fragment lengths indicates the presence or absence of a site of localization. For example, detecting an abnormal distribution of cell-free pathogen nucleic acids may indicate that the infection is in an organ, while a normal distribution of cell-free pathogen nucleic acids may indicate that the infection is not is in an organ. In some cases, detecting an abnormal distribution of cell-free pathogen nucleic acids may indicate that the infection is in an organ, while a normal distribution of cell-free pathogen nucleic acids may indicate that the infection is not in an organ.

Threshold Value or Range of Values for Organ-Specific RNA

In some cases, a threshold cut-off can be used as an indicator that an organ in the subject is infected by a pathogen as provided herein. A threshold cut-off can be determined as provide herein by using organ-specific RNA sequences from a subject infected by a pathogen and comparing those to a control or reference.

In some cases, the sample is identified as having an infected organ with an accuracy of greater than 75%, 80%, 85%, 86%, 87%, 88%, 89%, 90%, 91%, 92%, 93%, 94%, 95%, 96%, 97%, 98%, 99%, 99.5% or more. In some cases, the sample is identified as having an infected organ with a sensitivity of greater than 75%, 80%, 85%, 86%, 87%, 88%, 89%, 90%, 91%, 92%, 93%, 94%, 95%, 96%, 97%, 98%, 99%, 99.5% or more. In some cases, the sample is identified as having an infected organ with a specificity of greater than 75%, 80%, 85%, 86%, 87%, 88%, 89%, 90%, 91%, 92%, 93%, 94%, 95%, 96%, 97%, 98%, 99%, 99.5% or more 95%.

In some cases, the sample is identified as having an infected organ with a positive predictive value of at least 95%, 95.5%, 96%, 96.5%, 97%, 97.5%, 98%, 98.5%, 99%, 99.5% or more. In some cases, the sample is identified as having an infected organ with a negative predictive value of at least 95%, 95.5%, 96%, 96.5%, 97%, 97.5%, 98%, 98.5%, 99%, 99.5% or more.

In some cases, the sample is identified as having an infected organ with a sensitivity of greater than 75%, 80%, 85%, 86%, 87%, 88%, 89%, 90%, 91%, 92%, 93%, 94%, 95%, 96%, 97%, 98%, 99%, 99.5% or more, and a specificity of greater than 75%, 80%, 85%, 86%, 87%, 88%, 89%, 90%, 91%, 92%, 93%, 94%, 95%, 96%, 97%, 98%, 99%, 99.5% or more 95%.

B. Individualized Treatment and Monitoring

The present disclosure also provides methods for individualized treatment for an infected subject or a subject who is susceptible or at risk for infections (e.g., immunosuppressed, immunocompromised, living conditions, or genetic variations resulting in increased susceptibility for infection). Individualized treatment can include predicting if an infection will progress to an invasive disease stage, monitoring the efficacy of a therapy in a subject, modifying a therapeutic regimen depending on the subject's response to the therapy, and determining the pathogen's resistance to a particular therapeutic.

In some cases, the methods can be used to detect, diagnose, predict, or prognose the pathogen's resistance to a particular therapeutic. In some cases, the methods may further comprise sequencing of the subject's DNA for genetic variations that are associated with therapeutic resistance to therapeutics or to a particular therapeutic.

In some cases, samples may be collected serially at various times before or during the course of the infection to determine the pathogen's and subject's response to a treatment, thereby providing a regimen that is individually tailored. In some cases, the serially-collected samples are compared to each other to determine whether the infection is improving or worsening in the subject.

The treatment may involve administering a drug or other therapy to reduce or eliminate the colonization or invasive disease associated with the infection. In some cases, the subject may be treated prophylactically to prevent the development of an infection. Any medical procedure or treatment including administration of a drug can be used to improve or reduce the symptoms of an infection. Some nonlimiting exemplary drugs that can be used are antibiotics (such as ampicillin, sulbactam, penicillin, vancomycin, gentamycin, aminoglycoside, clindamycin, cephalosporin, metronidazole, timentin, ticarcillin, clavulanic acid, cefoxitin), antiretroviral drugs (e.g., highly active antiretroviral therapy (HAART), reverse transcriptase inhibitors, nucleoside/nucleotide reverse transcriptase inhibitors (NRTIs), Non-nucleoside RT inhibitors, and/or protease inhibitors), or immunoglobulins.

The present disclosure also provides methods of adjusting a therapeutic regimen. For example, the subject may have been administered a drug to treat the infection. The methods provided herein may be used to track or monitor the efficacy of the drug treatment. In some cases, the therapeutic regimen may be adjusted, depending on upward or downward course of the infection. For example, if the methods provided herein indicate that an infection is not improving with drug treatment, the therapeutic regimen may be adjusted by changing the type of drug or treatment, discontinuing the use of the drug, continuing the use of the drug, increasing the dose of the drug, or adding a new drug or treatment to the subject's therapeutic regimen.

In some cases, the therapeutic regimen may involve a particular procedure. For example, in some cases, the methods may indicate a need for a surgical procedure or an invasive diagnostic procedure such as to removing a tumor or performing a biopsy to determine if an organ is infected. Likewise, if the methods indicate than an infection is improving or resolved by a therapeutic intervention, then adjusting a therapeutic regimen may involve reducing or discontinuing the treatment. In other cases, no therapeutic regimen may be given instead "watchful waiting" or "watch and wait" approach may be used to see if the infection clears up without any additional medical intervention.

Figure 6:
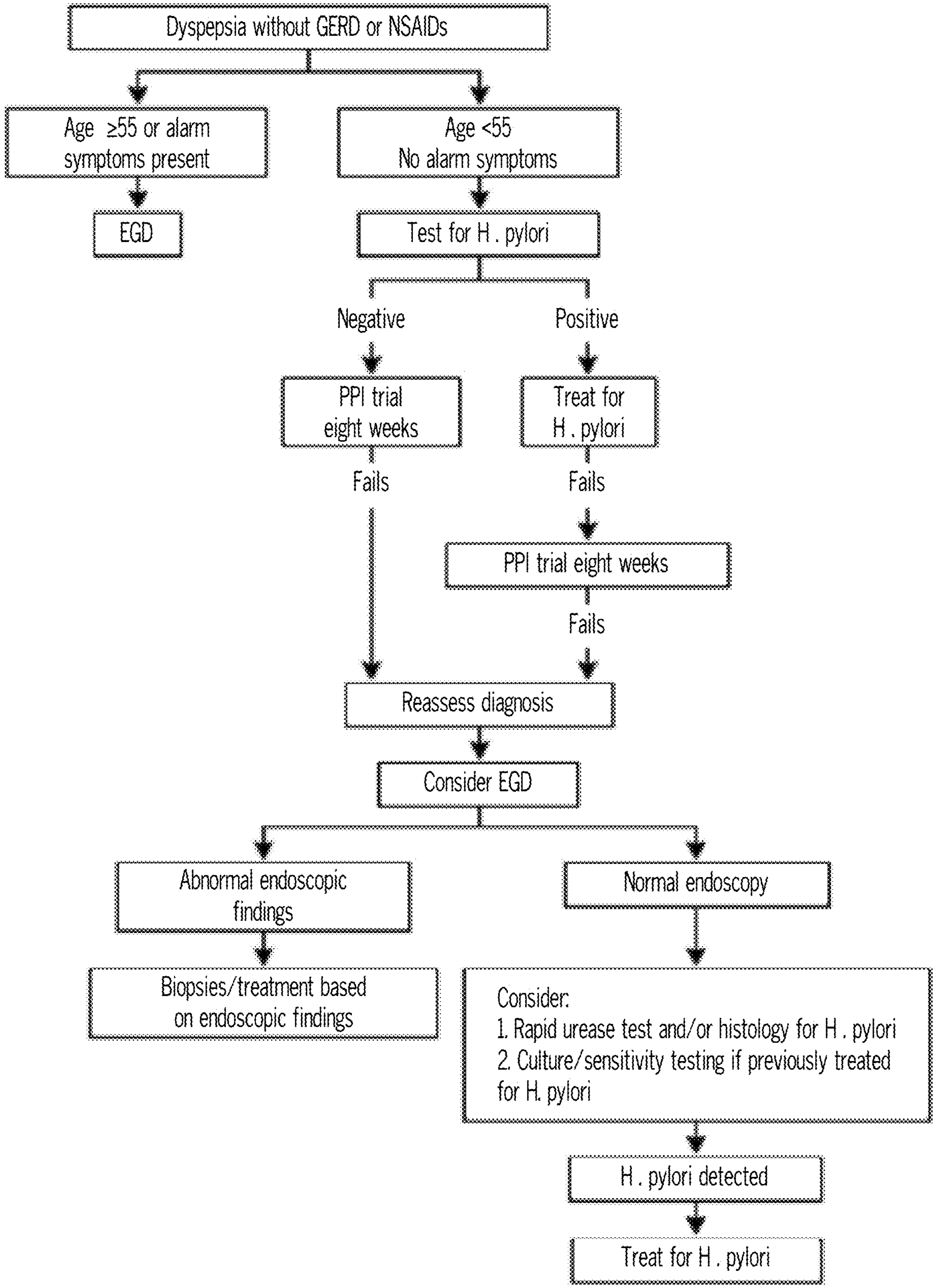
FIG. 6 shows a diagnostic workflow ending with treatment for a positive diagnosis of *H. pylori.*

The methods of the disclosure may comprise detection of a pathogen in a subject. In some cases, the method can comprise using whole-genome sequencing of the sample. In some cases, the method can comprise using targeted sequencing of the sample, where specific primers are used to detect a particular pathogen of interest. Often, a pathogen can have a suggested treatment cycle. For example, the treatment cycle for *H. pylori* is shown in FIG. 6. The methods provided by the disclosure may be used at any stage in the treatment cycle.

The methods of the disclosure can be applied to any pathogen that has various stages of infection. The methods may be especially useful for pathogens that have a colonization stage and an invasive disease stage. In some cases, the invasive disease stage may be caused by the pathogen infection. In some cases, the invasive disease stage may be associated with the pathogen infection.

The disclosure provides methods to detect, monitor, diagnose, prognose, treat, monitor, predict, or prevent colonization by *Heliobacter pylori* (*H. pylori*). *H. pylori* colonization can be asymptomatic. In some cases, colonization may appear as an acute gastritis with abdominal pain (stomach ache) or nausea. The disclosure provides methods to detect, monitor, diagnose, prognose, treat, or prevent invasive *H. pylori* disease. Subjects with invasive *H. pylori* disease may develop complications such as, chronic gastritis, peptic ulcer disease, gastric adenocarcinoma, stomach cancers, and/or lymphoma.

The disclosure provides methods to detect, monitor, diagnose, prognose, treat, predict, or prevent colonization by *Clostridium difficile* (CDI). CDI may present as asymptomatic or symptomatic. The clinical spectrum of a CDI infection can range from mild-to-moderate, severe, or complicated disease. Subjects with mild-to-moderate CDI may present with diarrhea, colitis, including fever, leukocytosis, and/or cramps. The severity of CDI abdominal and systemic symptoms may increase with the severity of the infection. The methods may be used to detect, monitor, diagnose, prognose, treat, or prevent invasive CDI disease. Subjects with complicated or invasive CDI disease may develop pseudomembranous colitis, toxic megacolon, perforation of the colon, and/or sepsis.

The disclosure provides methods to detect, monitor, diagnose, prognose, treat, predict, or prevent colonization by *Haemophilus influenza*. Generally, *Haemophilus influenza* colonizes the upper respiratory tract of a subject. The disclosure provides methods to detect, monitor, diagnose, prognose, treat, or prevent invasive *Haemophilus influenza* disease. Subjects with invasive *Haemophilus influenza* disease may develop complications such as, sepsis and/or meningitis.

The disclosure provides methods to detect, monitor, diagnose, prognose, treat, or prevent colonization by Salmonella. The disclosure also provides methods to detect, monitor, diagnose, prognose, treat, predict, or prevent invasive Salmonella disease. Some non-limiting examples of Salmonella serotypes that are associated with invasive disease include but are not limited to, Typhimurium, Typhi, Enteritidis, Heidelberg, Dublin, Paratyphi A, Choleraesuis, and Schwarzengrund. Subjects with invasive Salmonella disease may develop bacteremia, meningitis, enteric fever and/or invasive non-typhoidal Salmonella (iNTS) disease.

The disclosure provides methods to detect, monitor, diagnose, prognose, treat, predict, or prevent colonization by *Streptococcus pneumoniae*. The disclosure also provides methods to detect, monitor, diagnose, prognose, treat, or prevent invasive *Streptococcus pneumoniae* disease. Subjects with invasive pneumococcal disease may develop bacteremia and/or meningitis.

The disclosure provides methods to detect, monitor, diagnose, prognose, treat, or prevent colonization by Cytomegalovirus (CMV). Subjects infected with CMV may have no symptoms as the virus can cycle to dormant periods. The disclosure also provides methods to detect, monitor, diagnose, prognose, treat, predict, or prevent invasive CMV disease. Subjects with invasive CMV disease may develop complications in their eyes, lungs, and/or digestive system.

The disclosure provides methods to detect, monitor, diagnose, prognose, treat, predict or prevent colonization by Human Papilloma virus (HPV). Subjects with colonization by HPV may present as non-invasive cervical intraepithelial neoplasms and/or genital warts. The present disclosure also provides methods to detect, monitor, diagnose, prognose, treat, or prevent invasive HPV disease. Subjects with invasive HPV disease may develop cervical cancer, anal squamous cell carcinoma, and/or anal carcinoma in situ.

The disclosure provides methods to detect, monitor, diagnose, prognose, treat, predict, or prevent colonization by Epstein-Barr virus (EBV). Subjects colonized with EBV may be asymptomatic or present with fatigue, fever, inflamed throat, swollen lymph nodes in the neck, enlarged spleen, swollen liver, and/or a rash. The disclosure also provides methods to detect, monitor, diagnose, prognose, treat, predict, or prevent invasive EBV disease. Subjects with invasive EBV disease may develop infectious mononucleosis (e.g., glandular fever), have a higher risk of certain autoimmune diseases, develop cancers such as, Hodgkin's lymphoma, Burkitt's lymphoma, gastric cancer, nasopharyngeal carcinoma, hairy leukoplakia, and/or central nervous system lymphomas.

The disclosure provides methods to detect, monitor, diagnose, prognose, treat, predict or prevent colonization by hepatitis B (HBV). HBV infections can be transient or chronic. The disclosure also provides methods to detect, monitor, diagnose, prognose, treat, predict, or prevent invasive disease associated with an HBV infection. Subjects with invasive HBV disease may develop cirrhosis, hepatocellular carcinoma, liver infection, and/or liver failure.

The disclosure provides methods to detect, monitor, diagnose, prognose, treat, predict or prevent colonization by hepatitis C virus (HCV). HCV infection can be acute or chronic. Often, HCV colonization can be asymptomatic. When signs and symptoms are present, they may include jaundice, along with fatigue, nausea, fever and muscle aches. Some subjects may have spontaneous viral clearance where others may progress to a chronic stage. However, where an HCV infection becomes chronic it may result in invasive HCV disease. The disclosure also provides methods to detect, monitor, diagnose, prognose, treat, predict, or prevent invasive HCV disease. Subjects with an invasive HCV disease may develop cirrhosis, hepatocellular carcinoma, liver infection, and/or liver failure.

The disclosure provides methods to detect, monitor, diagnose, prognose, treat, predict or prevent colonization by human T-cell lymphoma virus 1 (HTLV-1). HTLV-1 infects the T cells of a subject. Subjects infected with HTLV-1 may be asymptomatic for years. The disclosure also provides methods to detect, monitor, diagnose, prognose, treat, predict, or prevent invasive HTLV-1 disease. Subjects with an invasive HTLV-1 disease may develop cancer of the T-cell (ATL) leukemia, HTLV-1 associated myelopathy/tropical spastic paraparesis (HAM/TSP), or other conditions.

The disclosure provides methods to detect, monitor, diagnose, prognose, treat, or prevent colonization by gonorrhea. Subjects with a colonization infection may have no symptoms, while others may present with symptoms such as, burning with urination, testicular or pelvic pain, and/or discharge from the genitals. The disclosure provides methods to detect, monitor, diagnose, prognose, treat, predict, or prevent invasive gonorrhea disease. Subjects with invasive gonorrhea disease may develop skin lesions, joint infection (e.g., pain and swelling in the joints), endocarditis, and/or meningitis.

The disclosure provides methods to detect, monitor, diagnose, prognose, treat, or prevent colonization by Syphilis. A syphilis infection can be divided into a primary, secondary, latent, and tertiary stages. A subject with primary stage may present with a sore. A subject with secondary stage may present with a skin rash, swollen lymph nodes, and/or a fever. During the latent or invisible stage of syphilis infection subjects are generally asymptomatic. The disclosure also provides methods to detect, monitor, diagnose, prognose, treat, predict, or prevent invasive syphilis disease. A subject with tertiary stage or invasive disease may develop complications in other organ systems including but not limited to the heart, blood vessels, brain, and/or nervous system.

The disclosure provides methods to detect, monitor, diagnose, prognose, treat, or prevent colonization by trichomoniasis. Subjects with a colonization infection may be asymptomatic or they may develop inflammation in their genital area. The present disclosure also provides methods to detect, monitor, diagnose, prognose, treat, predict, or prevent invasive trichomoniasis disease. Subjects with invasive trichomoniasis disease may develop cervical cancer and/or prostate cancer.

The disclosure provides methods to detect, monitor, diagnose, prognose, treat, or prevent colonization by human herpesvirus 8 (HHV-8), is also known as Kaposi sarcoma-associated herpesvirus, or KSHV. Healthy subjects with a colonization infection are generally asymptomatic. However, subjects with weakened immune systems may develop invasive HHV-8 disease. The disclosure also provides methods to detect, monitor, diagnose, prognose, treat, predict, or prevent invasive HHV-8 disease. Subjects with invasive HHV-8 disease may develop Kaposi sarcoma and/or several lymphoproliferative disorders such as, primary effusion lymphoma, multicentric Castleman disease, or B-cell lymphoma.

The disclosure provides methods to detect, monitor, diagnose, prognose, treat, or prevent colonization by Merkel cell polyomavirus. Subjects with a colonization infection may be asymptomatic. The disclosure also provides methods to detect, monitor, diagnose, prognose, treat, predict, or prevent invasive Merkel cell polyomavirus disease. Subjects with invasive Merkel cell polyomavirus disease may develop Merkel cell carcinoma (MCC) tumors, a rare but aggressive form of skin cancer.

The disclosure provides methods to detect, monitor, diagnose, prognose, treat, or prevent colonization by Chlamydia. Subjects with a colonization infection may be asymptomatic or they may present with burning sensation when urinating or discharge from their genitals. The disclosure also provides methods to detect, monitor, diagnose, prognose, treat, predict, or prevent invasive Chlamydia disease. Untreated chlamydia can progress to invasive disease stage spreading to the uterus and/or fallopian tubes in female subjects. Subjects with invasive chlamydia disease may develop pelvic inflammatory disease (PID), which can result in long-term pelvic pain, inability to get pregnant, and ectopic pregnancy.

In some cases, the subject is infected or at risk of infection by a pathogen that has different infection stages, such as colonization stage, and an invasive disease stage. A colonized subject may have no clinical signs or symptoms. In other cases, a colonized subject may have clinical signs or symptoms. A subject with an invasive disease can present with clinical signs or symptoms. In other cases, a subject with an invasive disease can present with no clinical signs or symptoms.

The subject may have or be at risk of having another disease or disorder. For example, the subject may have, be at risk of having, or be suspected of having cancer (e.g., breast cancer, lung cancer, stomach cancer, hematological cancer, etc.).

In some cases, the subject can have increased risk factors for contracting an infectious disease or progressing to an invasive disease stage. In some cases, the risk factors are associated with living conditions. Some non-limiting examples of risk factors associated with living conditions include, but are not limited to, crowded living conditions, no reliable source of clean water, living or visiting a developing country, and/or cohabitating with infected people.

In some cases, the risk factors for contracting an infection or for progression to an invasive disease are genetic variants in the subject's genomic DNA. Genetic variants that can be risk factors for infection include but are not limited to, single-nucleotide polymorphisms, deletions, insertions, or the like. In some other cases, subjects can have family history of disease such as gastric cancer, family history of lymphocytic gastritis, hyperplastic gastric polyps, or hyperemesis gravidarum.

The subject may have or be at risk of having another disease or co-infection by more than one pathogen. In some cases, the subject is immunosuppressed (e.g., organ transplant patients). In some cases, the subject is immunocompromised (e.g., by chemotherapy treatment, immune deficiency caused by AIDS, or general illness such as diabetes or lymphoma).

In some cases, the subject may present with one or more clinical symptoms. Non-limiting examples of clinical symptoms can include aching or burning pain in the abdomen, abdominal pain that worsens when the stomach is empty, nausea, loss of appetite, frequent burping, bloating in the stomach area, weight loss, severe or persistent abdominal pain, difficulty swallowing, bloody or black tarry stools, and/or bloody or black vomit. Additional clinical symptoms are known in the art.

In some cases, the subject can present with a clinical pathology such as atrophic gastritis, acute or chronic gastritis, hyperacidity, antigenic stimulation, active peptic ulcer disease, a past history of PUD, low-grade gastric mucosa-associated lymphoid tissue lymphoma, a history of endoscopic resection of early gastric cancer, dyspepsia, Barrett's esophagus, functional dyspepsia, unexplained iron deficiency, or idiopathic thrombocytopenia purpura (ITP).

The subject may be infected by a pathogen or microorganism of any type, including bacterial, viral, fungal, parasitic, prokaryotic, eukaryotic, etc. In some cases, the pathogen is known, while in other cases it may be a known commensal.

In some cases, the subject may have an active or latent infection. In some cases, the subject is infected, but the infection is below the level of diagnostic sensitivity of other tests previously conducted on the subject. In some cases, the subject is infected but asymptomatic or the infection is at a sub-clinical level.

In some cases, the subject may have been previously treated or may be treated with a drug such as an antimicrobial, antibacterial, antiviral, and/or antiparasitic drug or a medical procedure. In some cases, the subject may have not had biopsy, endoscopy, colonoscopy, blood culture, or other such procedure prior to the use of the methods herein. In some cases, the subject may have or may have had a stool antigen test, urea breath test, serology, urease testing, histology, bacterial culture and sensitivity testing, biopsy, or endoscopy prior to the use of the methods herein.

The present disclosure provides methods for determining the infection stage or site in a subject using the nucleic acids obtained from a clinical sample (e.g., blood, serum, cells, or tissue). In some embodiments, the method comprises making a spiked-sample by adding synthetic nucleic acids provided by the disclosure; extracting the nucleic acids from the spiked-sample; generating a spiked-sample library; enriching the spiked-sample library for a target nucleic acid of interest; conducting a sequencing assay to obtain sequence reads from the spiked-sample library; and determining a measurement from the detected nucleic acids (e.g., DNA, RNA cell-free DNA or cell-free RNA), and comparing this measurement to a control or a reference to determine the infection stage or a site of localization (e.g., organ, or type tissue) in a subject.

Embodiments of the methods may comprise extracting nucleic acids or target nucleic acids from the sample or purification of nucleic acids or target nucleic acid from unwanted components in a reaction mixture (e.g., ligation, amplification, restriction enzyme, end repair, etc). Any means of extracting nucleic acids known in the art may be used in the methods of the application.

The extraction can comprise separating the nucleic acids from other cellular components and contaminants that may be present in the sample. Nucleic acids can be extracted from a sample using liquid extraction (e.g., TRIzol®, DNAzol®) techniques. In some cases, the extraction is performed by phenol chloroform extraction or precipitation by organic solvents (e.g., ethanol, or isopropanol). In some cases, the extraction is performed using nucleic acid-binding columns.

In some cases, the extraction is performed using commercially available kits such as the QIAGEN® QIAamp® Circulating Nucleic Acid extraction Kit, Thermo Fisher Scientific® Qubit™ dsDNA HS Assay nucleic acid extraction kit, Agilent® DNA 1000 nucleic acid extraction kit, TruSeq Sequencing Library Preparation nucleic acid extraction kit, QIAamp® Circulating Nucleic Acid extraction Kit, QIAGEN® DNeasy® nucleic acid extraction kit, QIAamp® nucleic acid extraction kit, QIAGEN® Midi nucleic acid extraction kit, QIAprep® spin nucleic acid extraction kit, or nucleic acid-binding spin columns (e.g., QIAGEN® DNA mini-prep nucleic acid extraction kit). In some cases, extraction of cell-free nucleic acids may involve filtration or ultra-filtration.

Nucleic acids can be extracted or purified by the use of magnetic beads. For example, magnetic beads with an iron-oxide core and a surface coated with molecules containing a free carboxylic acid or a synthetic polymer can be used. The salt concentration or polyalkylene glycol can be adjusted to control the strength of the bonds between functional groups and nucleic acid, allowing for controlled and reversible binding. Finally, nucleic acids can be released from the magnetic particles with an elution buffer. In some cases, the extraction or purification is performed using commercially available kits such as Omega Bio-tek Mag-Bind® magnetic bead kit, Agencourt® RNAClean™ magnetic beads, and/or XP magnetic beads.

The method may comprise purifying the target nucleic acids. Purification may be performed where a user desires to isolate the target nucleic acid from unwanted components in a reaction mixture. Nonlimiting exemplary purification methods include ethanol precipitation, isopropanol precipitation, phenol chloroform purification, and column purification (e.g., affinity-based column purification), dialysis, filtration, or ultrafiltration.

Methods of generating nucleic acid libraries are known in the art.

Computer Control Systems

Figure 7:
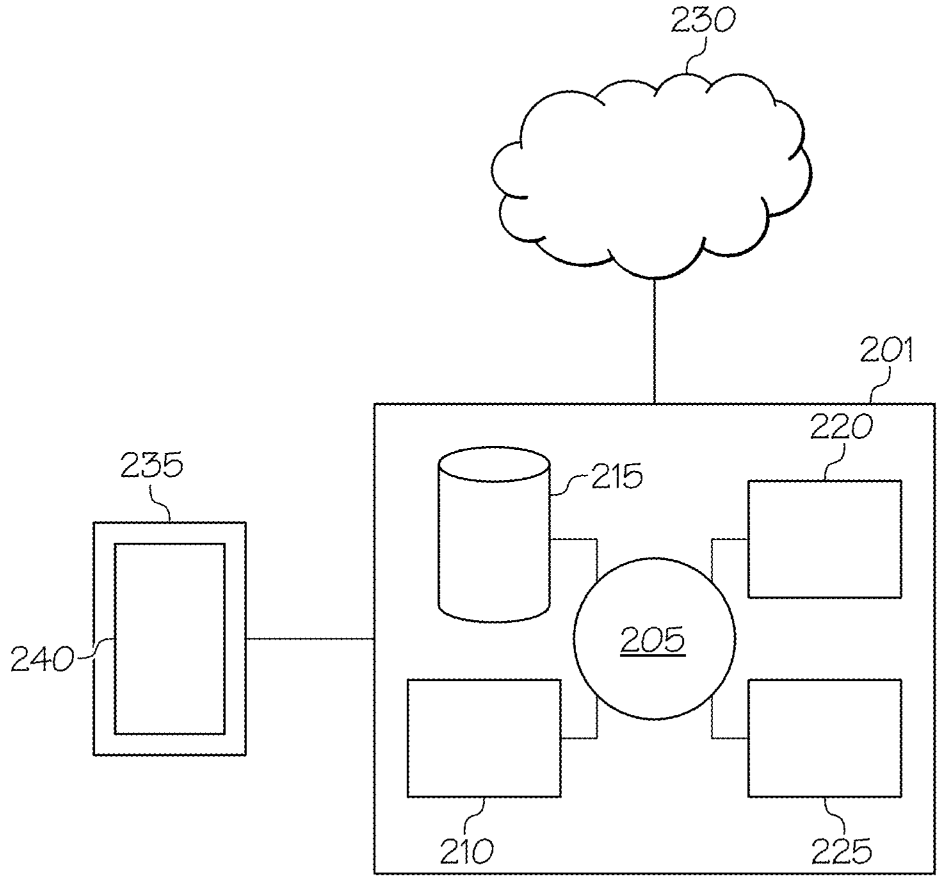
FIG. 7 depicts a computer control system that is programmed or otherwise configured to implement methods provided herein.

The present disclosure provides computer control systems that are programmed to implement methods of the disclosure. FIG. 7 shows a computer system 201 that is programmed or otherwise configured to implement methods of the present disclosure.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 201, can implement a peer-to-peer network, which may enable devices coupled to the computer system 201 to behave as a client or a server.

The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user (e.g., healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, an output of a report, which may include a diagnosis of a subject or a therapeutic intervention for the subject. Examples of UI's include, without limitation, a graphical user interface (GUI) and web-based user interface. The analysis can be provided as a report. The report may be provided to a subject, a health care professional, a lab-worker, or other individual.

Methods and systems of the present disclosure can be implemented by way of one or more algorithms. An algorithm can be implemented by way of software upon execution by the central processing unit 205. The algorithm can, for example, facilitate the enrichment, sequencing and/or detection of pathogen nucleic acids.

Information about a can be entered into a computer system, for example, a patient identifier such as information about infection stage or risk of infection, patient background, patient medical history, previous infections, or ultrasound scans. Patient identifiers can be separated from clinical samples to obtain de-identified samples, for example by the sample sender or the sample recipient. Patient identifiers can be replaced with accession numbers or other non-individual identifying code. Clinical samples can be sequenced using a high-throughput sequencer. De-identified sample sequence data generated by sequencer can be uploaded to a server, such as a cloud server. Using methods disclosed herein, pathogen nucleic acids within de-identified samples can be detected to obtain de-identified result data. De-identified result data can be downloaded from the server. The de-identified result data can be associated with patient identifiers, for example by the sample sender or the sample recipient.

An electronic report can be generated to indicate the infection stage of a pathogen. An electronic report can be generated to indicate prognosis. An electronic report can be generated to indicate diagnosis. If an electronic report indicates there is a treatable infection, the electronic report can be generated to prescribe a therapeutic regimen or a treatment plan. The computer system can be used to analyze results from a method described herein, report results to a patient or doctor, or come up with a treatment plan.

Kits

Also provided are reagents and kits thereof for practicing one or more of the methods described herein. The subject reagents and kits thereof may vary greatly. Reagents of interest include reagents specifically designed for use in identification, detection, and/or quantitation of one or more pathogen nucleic acids in a sample obtained from a subject infected with a pathogen or at risk of infection.

The kits may comprise reagents necessary to perform nucleic acid extraction and/or nucleic acid detection using the methods described herein such as PCR and sequencing.

The kit may further comprise a software package for data analysis, which may include reference profiles for comparison with the test profile from a clinical sample, and in particular may include reference databases. The kits may comprise reagents such as buffers and water.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

It will be understood that the reference to the below examples is for illustration purposes only and do not limit the scope of the claims.

EXAMPLES

Example 1. Distribution Shapes and Microbe Status

Processing of biological samples with a method that lacks bias or enables correction of the bias in the region of fragment lengths of interest allows the measurement of the endogenous fragment length distributions and creates the potential to use endogenous fragment length distribution profiles to inform the diagnostic as well as therapeutic aspects of a treatment. Several different clinical samples were therefore processed show the diversity of the fragment length distribution profiles. A direct-to-library process with no detectable length and GC bias within the investigated fragment length range was applied to obtain the shapes of the endogenous fragment length distributions.

Clinical plasma samples: 36 diagnostically positive (i.e. the presence of microbes confirmed with an orthogonal test, e.g.: blood culture, targeted PCR, Karius Test) were collected from 36 human subjects. Single-centrifugation step plasma extraction process from whole blood within 24 hours of sample collection was performed for each sample, as previously described (See, the first centrifugation step in Fan H C et al., PNAS 2008; 105 (42): 16266-16271, which is incorporated by reference in its entirety herein, including any drawings), and stored at −80° C. until use. Samples were then thawed, and 200 μL of each plasma was spiked with 2 μL of Spike-in Master Mix (see below).

Positive Assay Control Samples: Two positive controls, referred to as assay control samples (AC) were processed for each group of 18 samples, respectively. AC samples were prepared from human asymptomatic plasma spiked with enzymatically sheared genomes of human pathogens, purchased in purified form from ATCC (American Type Culture Collection). Selected human pathogens were *Aspergillus fumigatus, Escherichia coli, Pseudomonas aeruginosa*, and *Staphylococcus epidermidis.* 10 μL of Spike-in Master Mix (see below) were added per 1 mL of AC sample.

Negative Control Samples: Four 500 μL negative control samples (EC) per 18 samples were made from aqueous buffer (10 mM Tris pH 8, 0.1 mM EDTA, 0.05 v/v % Tween-20®) with 5 μL of Spiked-in Master Mix (see below) and served as controls for environmental contamination (i.e., microbe and pathogen nucleic acid contamination introduced by either the reagents, instrumentation, consumables, operators, and/or air during processing). These synthetic nucleic acids were used for normalizing the signal in the samples in order to account for variations in sample processing.

Spike-in Master Mix: A set of process control molecules were pre-mixed together in a single Spike-in Master Mix, with each Spike-in Master Mix containing a unique "ID Spike" process control molecule, See, for example, U.S. Pat. No. 9,976,181. Spike-in Master Mix contained three classes of molecules: ID Spike molecules, SPANK molecules, and SPARK molecules. The latter group of molecules was composed of two classes of SPARKs: GC dSPARKs and Long SPARKs. The molar concentration of the ID Spike, SPANK molecules, and long SPARK molecules in Spike-in Master Mix was 500 μM per molecule while GC dSPARK molecules were present at 50 μM per molecule.

"ID Spike" molecules: Each sample received a unique ID Spike single-stranded DNA molecule characterized by a 50 base pairs long unique sequence that was not present in any reference genome available in public databases at the time of processing.

SPANK molecules: SPANK molecules used were a pool of single-stranded DNA molecules, each 50 base pairs long with identical 3'-end and 5'-end sequences that were not present in any reference genome available in public databases at the time of processing. In addition, two stretches of 8 base pairs nested between the constant 3'-end and 5'end sequences were present and fully degenerate within the pool. The pool of SPANK molecules contained 416 unique SPANK molecules. The two degenerate stretches were separated by a stretch of four non-degenerate bases.

SPARK molecules: A GC Spike-in Panel was a set of molecules 32, 42, 52, and 75 nt long where 7 different sequences with GC content 20%, 30%, 40%, 50%, 60%, 70%, and 80% were included for each length. Like some of the other molecules provided above, GC dSPARK sequences did not occur in the available reference genomes. A Long SPARK sequence set was a group of 4 non-natural sequences, each with 50% GC content and lengths of 100 nt, 125 nt, 150 nt, and 175 nt. A complete set of SPARK molecules contained 32 different sequences.

Library Generation: Direct-to-library generation was described in U.S. Provisional Application 62/770,181 filed Nov. 21, 2018, herein incorporated by reference in its entirety. Here, a template-switching based method with Proteinase K was utilized. Briefly, 50.0 μL of each spiked sample was mixed with 20.0 μL of 10× Terminal Transferase Reaction Buffer (NEB, Ipswich, MA), 5.0 μL of Proteinase K protease (Sigma-Aldrich®), 2.0 μL of 10% Tween-20® (Thermo Fisher Scientific®, Waltham, MA), 2.0 μL of 10% Triton X100 (Thermo Fisher Scientific®, Waltham, MA) and 121.0 μL Nuclease-free water. The mixture was heated to 60° C. for 20 minutes and 95° C. for 10 minutes and placed on ice until cool. 2.0 μL of 10 mM dATP, 2.0 μL Terminal Transferase (20 u/μL, NEB, Ipswich, MA) and 6.0 μL Nuclease-free water was added to prepare the A-tailing reaction which was incubated at 37° C. for 40 min. 300.0 μL of Lysis/Binding Buffer (Thermo Fisher Scientific®, Waltham, MA) was added to the reaction. The entire volume was then added to 50.0 μL of Dynabeads™ oligo (dT) 25 (Thermo Fisher Scientific®, Waltham, MA) magnetic beads, which had been washed once with Lysis/Binding Buffer (Thermo Fisher Scientific®, Waltham, MA). The mixture was incubated at 25° C. and 600 RPM. The beads were then washed twice with 600.0 μL of Wash Buffer A (Thermo Fisher Scientific®, Waltham, MA) and twice with 300.0 μL of Wash Buffer B (Thermo Fisher Scientific®, Waltham, MA) before elution in 24.0 μL of elution buffer (Thermo Fisher Scientific®, Waltham, MA) at 80° C. and 600 RPM for 3 minutes. The entire eluate was transferred to a new plate. 2.0 μL 1 μM Poly dT primer (IDT) and 6 μL of SMARTScribe® 1st Strand buffer (5×) solution (Takara Bio®, Kusatsu, Japan) was added to the eluate and the resulting mixture incubated at 95° C. for 1 minute before placing on ice. The Extension and Template-switching mix was prepared by combining 4.5 μL SMARTScribe® 1st Strand buffer (5×) solution (Takara Bio®, Kusatsu, Japan), 0.5 μL dNTP mix (25 mM per nucleotide, Thermo Fisher Scientific®, Waltham, MA), 2.0 L SMARTScribe® Reverse Transcriptase (100 u/μL, Takara Bio®, Kusatsu, Japan), 2.0 μL 5 μM Template-switching Oligo (TS Oligo) (IDT), 5.0 μL of DTT reducing agent (20M, Takara Bio®, Kusatsu, Japan), and 4 μL Nuclease-free water. The resulting reaction mixture was incubated for 90 min at 42° C. and the reaction was heat denatured at 70° C. for 15 min. Next, 50.0 μL of NEBNext® Ultra II Q5 (NEB, Ipswich, MA), and 8.0 μL of indexing primer mixture (NEB, Ipswich, MA) were added to the reaction from the previous step. Amplification of the nucleic acids was performed then using the following temperature cycling program: 98° C. for 30 seconds, 8 cycles of 98° C. for 10 seconds, 65° C. for 75 seconds, and a final extension of 65° C. for 5 min. Final nucleic acid libraries were then pooled in groups of four ECs, two ACs, and eighteen clinical samples before using Agencourt® RNAclean™ AMPure® beads to purify the pool as described above. After purification, the concentration of the nucleic acids in the library pools was measured with TapeStation as described above and loaded on the sequencer according to the manufacturer's recommendations.

Sequencing: The samples were sequenced to obtain sequence reads using a NextSeq™ 500 sequencer by Illumina®. Sequencing was conducted following the manufacturer's instructions using 76 cycles.

Figure 8:
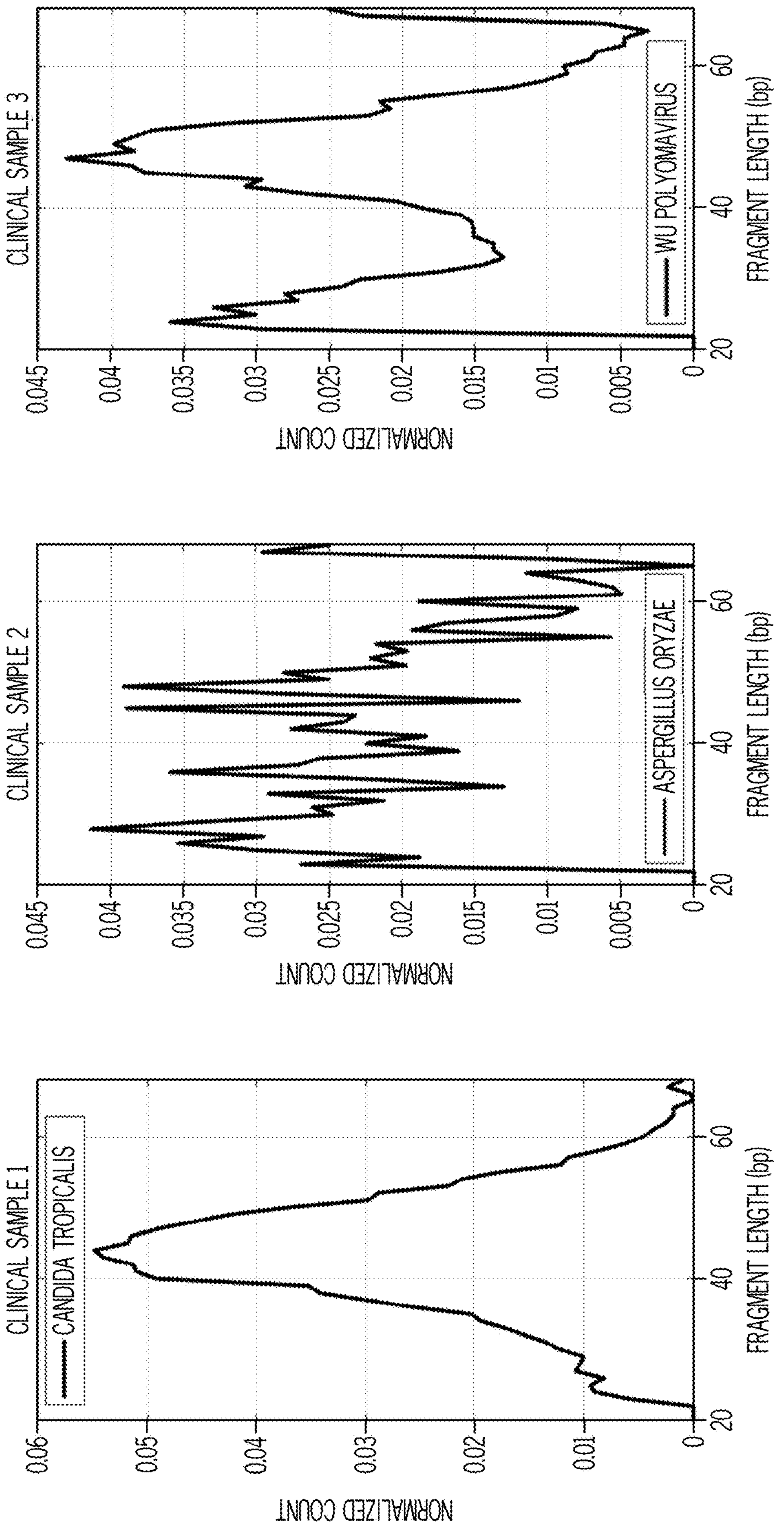
FIG. 8 depicts the distribution of fragment lengths for reads from three microbes detected in three different human plasma samples from which nucleic acid libraries were generated. The fragment length characteristic of interest in the figure is distribution shape. Each panel provides an example of a different distribution shape. In each panel, the normalized number of reads is shown on the y-axis and the fragment length is indicated on x-axis. The left panel provides an example of a "50-base pair peak" distribution shape. The middle panel provides an example of a short exponential-like distribution shape. The right panel provides an example of a complex distribution shape, wherein this particular complex distribution shape comprises aspects of the exponential decay like distribution shape and a single peak 50 base pair distribution. It is recognized that each distribution shape depicted reflect the distribution of fragment lengths in a nucleic acid library each generated from a distinct human plasma sample and provide one example of the indicated distribution shape type. Other distribution shapes are described elsewhere herein. Other distribution shapes are possible.

Sequencing data analysis: Primary sequencing output was demultiplexed by bcl2fastq v2.17.1.14 (with default parameters), followed by the removal of the template switching oligos using Cutadapt. The poly A tail was removed and reads were quality trimmed and subsequently filtered if shorter than 20 bases by Trimmomatic v 0.32. Reads that passed these filters were aligned against human and synthetic (including process control molecules and sequencing adapter) references using Bowtie v2.2.4. Reads with alignments to either were set aside. Reads potentially representing human satellite DNA were also filtered via a k-mer based method. The remaining reads were aligned against a microorganism reference database using BLAST® v2.2.30 software. Reads with alignments that exhibited both high percent identity and high query coverage were retained, with the exception of reads that aligned against any mitochondrial or plasmid reference sequences. PCR duplicates were removed based on their alignments. Relative abundances were assigned to each taxon in a sample based on the sequencing reads and their alignments. For each combination of read and taxon, a read-sequence probability was defined that accounted for the divergence between the microorganism present in the sample and reference assemblies in the database. A mixture model was used to assign a likelihood to the complete collection of sequencing reads that included the read sequence probabilities and the (unknown) abundances of each taxon in the sample. An expectation-maximization algorithm was applied to compute the maximum likelihood estimate of each taxon abundance. From these abundances, the number of reads arising from each taxon were aggregated up the taxonomic tree. A set of libraries may be prepared from the respective Negative Control Buffers and processed and sequenced within each batch. Estimated taxon abundances from the negative control samples within the batch may be combined to parameterize a model of read abundance arising from the environment with variations driven by counting noise. Statistical significance values may be computed for each estimated taxon abundance and those within the CRR at high significance levels comprised candidate calls (i.e., significant calls). Final calls (i.e., reportable calls) was made after additional filtering was applied, accounting for read location uniformity, read percent identity, and cross-reactivity originating from higher abundance calls. The number of reads of multiple fragment lengths for each reportable microbe within each processed nucleic acid library was determined, the fragment length distributions were evaluated and the fragment length characteristic of distribution shape was determined. FIG. 8 shows examples of some of the distinct fragment length distribution shapes observed among the detected microbes within the tested clinical samples. The range of fragment lengths shown is limited to 22 bp on the shorter end due to the minimum mapping length and 68 bp set by a combination maximum read length in the described sequencing experiment and adapter trimming algorithm. Consequently, the fragments longer than 68 bp contributed to the count in the 68 bp length bin. The three microbes detected in the three examples shown were *Candida tropicalis, Aspergillus oryzae*, and WU polyomavirus. The fragment length distribution shapes vary considerably between these microbes, and are not related to the particular species or superkingdom as shown by the remainder of the data (not shown).

Figure 9:
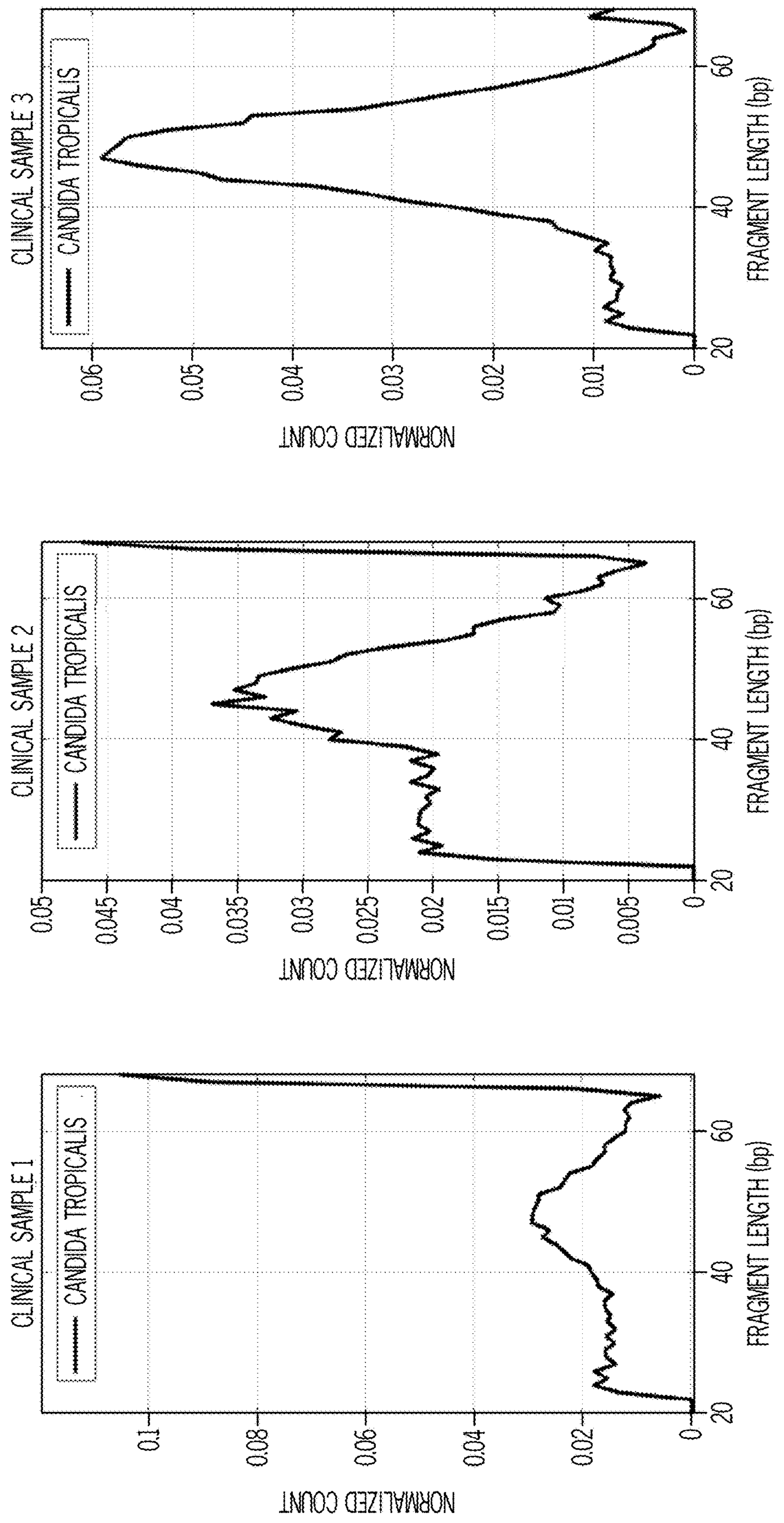
FIG. 9 provides examples relating to the fragment length characteristics of distribution segment amplitude and segment amplitude ratios. The panels depict the distribution of fragment lengths for reads of the same pathogen (*Candida tropicalis*) from three different clinical samples. In each panel, the normalized number of reads is shown on the y-axis and the fragment length is indicated on x-axis. The clinical samples are numbered 1 through 3 for the purpose of this figure. *Candida tropicalis* in Clinical Samples 1 and 2 show a distribution with higher long (>65 bp) fraction relative to the 50 bp peak as compared to *Candida tropicalis* in Clinical Samples 3 while all fragment length profiles have a clear peak at approximately 45-50 bp. The ratio of short reads (<40 bp) relative to the 50 bp peak also varies between the three samples. The distribution segment amplitude and segment amplitude ratios (<40 bp to 50 bp peak and >65 bp to 50 bp peak) reflect results obtained from one experiment.
Figure 10:
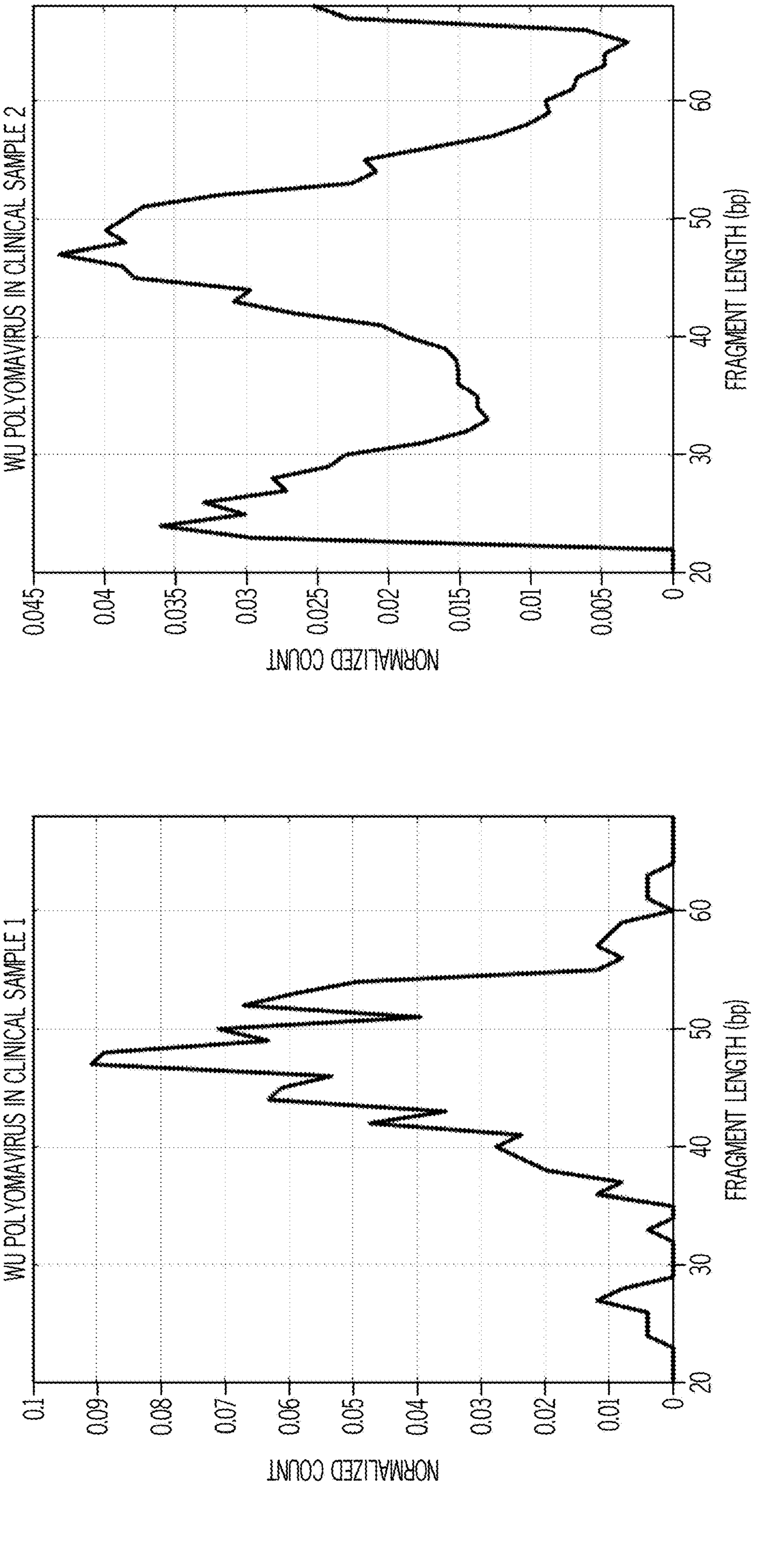
FIG. 10 depicts fragment length distribution of WU polyomavirus from two clinical samples. The left panel shows a distribution with a single peak around the 50 base pair (bp) fragment length. The right panel shows combination pattern comprising an exponentially distributed shape contribution, a peak, and a long fraction contribution. Without being limited by mechanism, the short-exponential like fraction may suggest incorporation of the virus in the human genome or degradation of the microbial nucleic acids by a process distinct from the one generating the fragments within the "50 bp peak".
Figure 11:
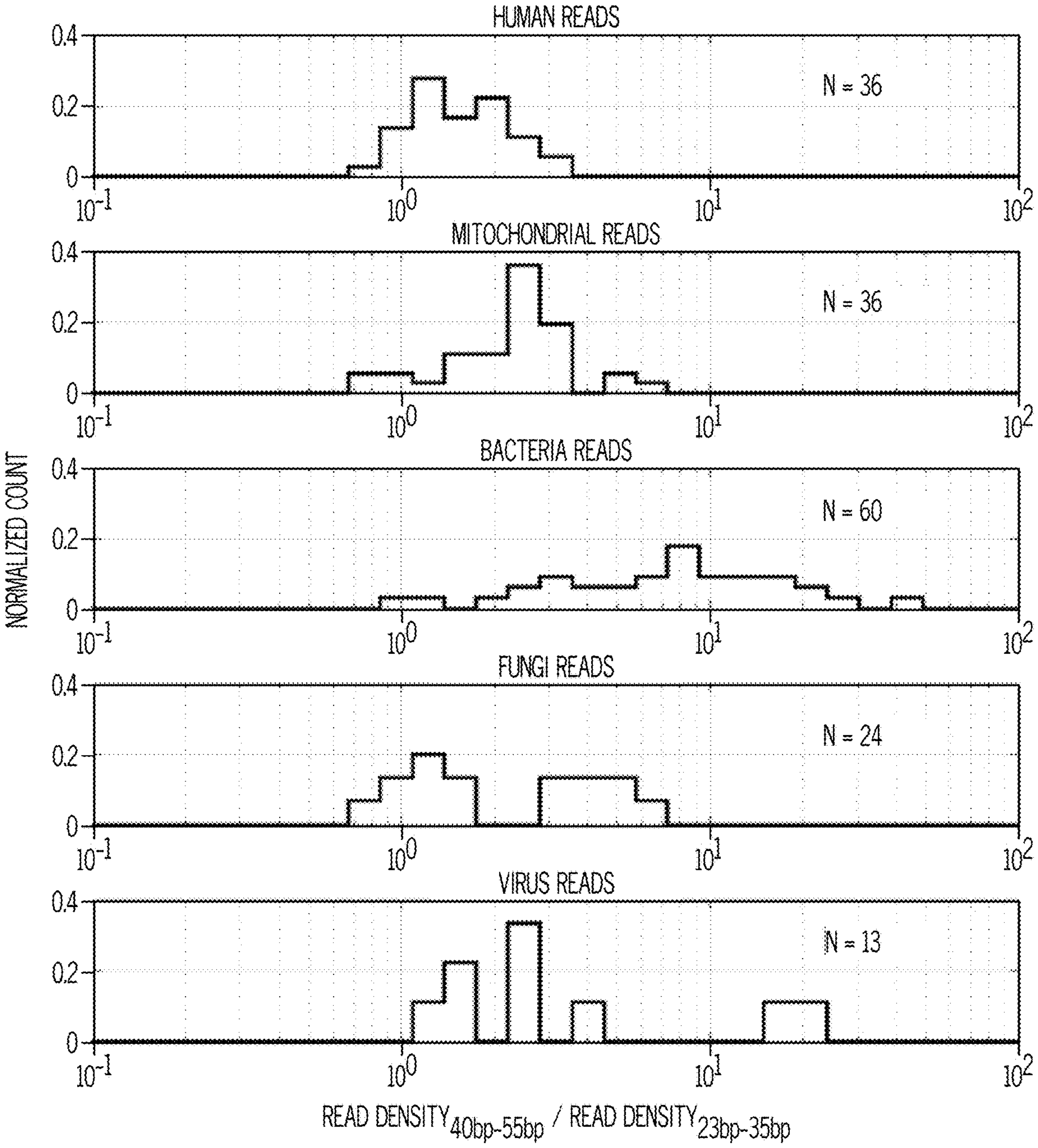
FIG. 11 provides examples relating to the fragment length characteristics of fragment count ratio in different distributions. The panels depict the ratio of fragment counts in the "50 bp peak" fraction vs. short exponential-like fraction (read density 40-55 bp/read density 23-35 bp, x-axis) versus normalized counts (y-axis). The same fraction for human and human mitochondria were added for reference. The ratio varies between kingdom types. The ratios for bacterial reads vary widely while the ratios for fungal reads show a bimodal pattern. The ratios for viral reads are also shown.

*Candida tropicalis* was detected in three different clinical samples processed here. The subset of reads from each sample that aligned to the *Candida tropicalis* reference genome was identified and their fragment length distributions were determined. Results are shown in FIG. 9 with *Candida tropicalis* fragment length distributions from each of the three samples in a separate panel. The left and middle panels show a distribution with higher short (<40 bp) and long (>65 bp) fraction relative to the 50 bp peak as compared to the right panel while they both have a clear peak at approximately 45-50 bp. The left 2 panels are from patients with disseminated *Candida tropicalis* infection, which without being limited by mechanism, can explain the increased amount of long and short fragments, relative to the peak. The different fragment length distributions may indicate a different state of disease or condition. WU polyomavirus was another example of a microbe that was detected in multiple clinical samples processed in this study and exhibited different fragment length distribution in each sample (FIG. 10). In one subject the WU polyomavirus showed only the "50 bp peak". The second subject showed considerable contribution of the short exponential-like fraction as well as higher fraction of reads longer than 68 bp. While not being limited by mechanism, the WU polyomavirus may have incorporated in the human genome in this sample or its genome was released into the bodily fluid, which caused different fragmentation patterns. In a total of 36 clinical samples (see above), 60, 24, and 13 bacterial, fungal, and viral microbes were detected, respectively. The fragment length distributions of these microbes vary considerably as demonstrated by examples set above. Next, the ratio of read counts detected in the "50 bp peak" peak vs. the short exponential-like region of the distribution for all the detected microbes or pathogens were determined. The obtained ratios were grouped by their superkingdom and histogram of ratios characteristic for each superkingdom was generated. Results from one such analysis are presented in FIG. 11. The same analysis was performed for the human DNA (i.e. host DNA) and human mitochondrial DNA (i.e. host mitochondrial DNA) as a control (FIG. 11.). The behaviour of the microbes depends on the superkingdom and that aspect must be accounted for when using fragment length distribution shapes and properties for diagnostic purposes.

Example 2. Analysis of Plasma Samples from a Pregnant Subject

Many types of non-host nucleic acids can be found in a sample obtained from a host. Fetal cell-free nucleic acids can be detected in maternal blood. In this samples, plasma samples were obtained from 15 pregnant women with consent and deidentified. The samples were processed and sequenced according to the ligation-based direct-to-library method described as Example 1 of U.S. Provisional Application 62/770,181 filed Nov. 21, 2018, herein incorporated by reference in its entirety. Only the samples from subjects pregnant with a male fetus were considered in this analysis. Reads that aligned only to the Y chromosome were considered to be fetal. Reads were aligned to the human genome using bowtie2. Reads that mapped to chromosome Y were then aligned using bowtie2 to an index created from all human chromosomes except for Y. Any reads that aligned to this index were discarded so that only the reads unique to chromosome Y remained.

Figure 12:
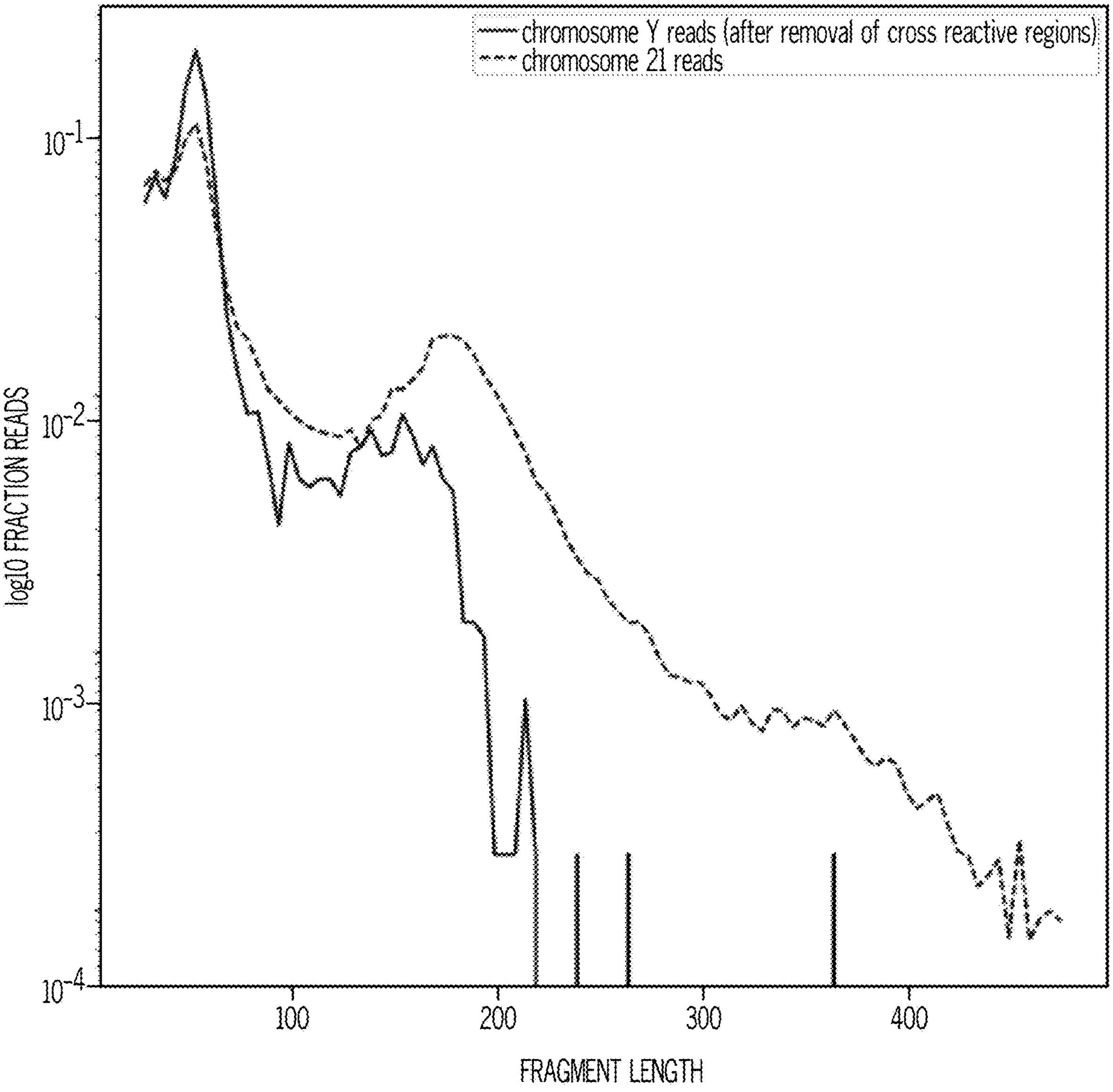
FIG. 12 provides a summary of fragment length distributions for maternal (dashed line) and fetal (solid line) cell-free nucleic acids. The "50 bp peak" appears narrower in the fetal distribution indicating a smaller fragment length range within the peak from the fetal nucleic acids. In addition, the ratio of fetal to maternal reads is higher in the "50 bp peak" region as compared to the nucleosomal length fragments (e.g. 150-200 bp region).

Fragment length distributions for maternal (dashed line) and fetal (solid line) cell-free nucleic acids from one individual are presented in FIG. 12. In this example, the ratio of fetal to maternal reads is higher in the "50 bp peak" region as compared to the nucleosomal fragment region (e.g. 150-200 bp region). On average, 4× higher concentration of the fetal fragments was observed within the "50 bp peak" region as compared to the nucleosomal length fragment region. The process employed here could be used to enrich for the fetal fraction.

Example 3. Analysis of Microbes Using Fragment Length Profiles

Figure 13:
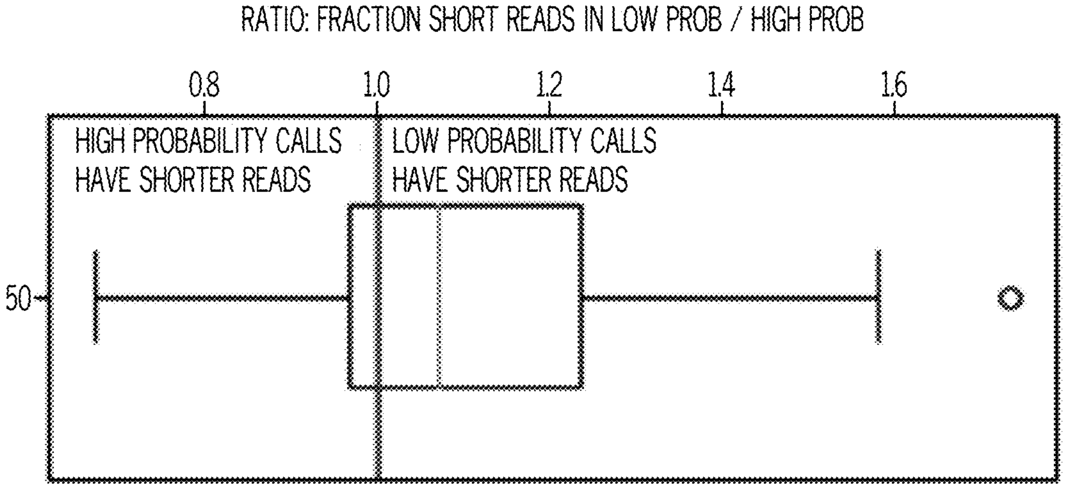
FIG. 13 provides a summary of fragment length distribution for microbes present as a pathogen or as a commensal microorganism. Pathogens tend to have longer fragment lengths than commensal microorganisms in an end-repairable double-stranded DNA-based assay.

Nucleic acid libraries were prepared and sequenced from over 4000 cell-free plasma samples using a validated Karius Test, an extraction-based method that recovers double-stranded DNA fragments in an unbiased way in respect to their length and GC-content within a fragment length range relevant to the cell-free nucleic acids. The fragment length profiles for detected microbes were generated and evaluated for 33 taxa that were called 10 or more time within the studied sample group. More specifically, the ratio of the fraction of short reads in low probability and high probability calls was evaluated. Results from one such experiment are presented in FIG. 13. In this experiment, the graph indicates more of the low probability calls have short reads than of the high probability calls. While not being limited by mechanism, these results may suggest clinical infections have longer fragment length distribution than colonizers or non-pathogenic organisms translocated in the bloodstream when end-repairable double-stranded cell-free DNAs are considered.

Example 4. Analysis of Site of Localization Using Fragment Length Profiles

Figure 14:
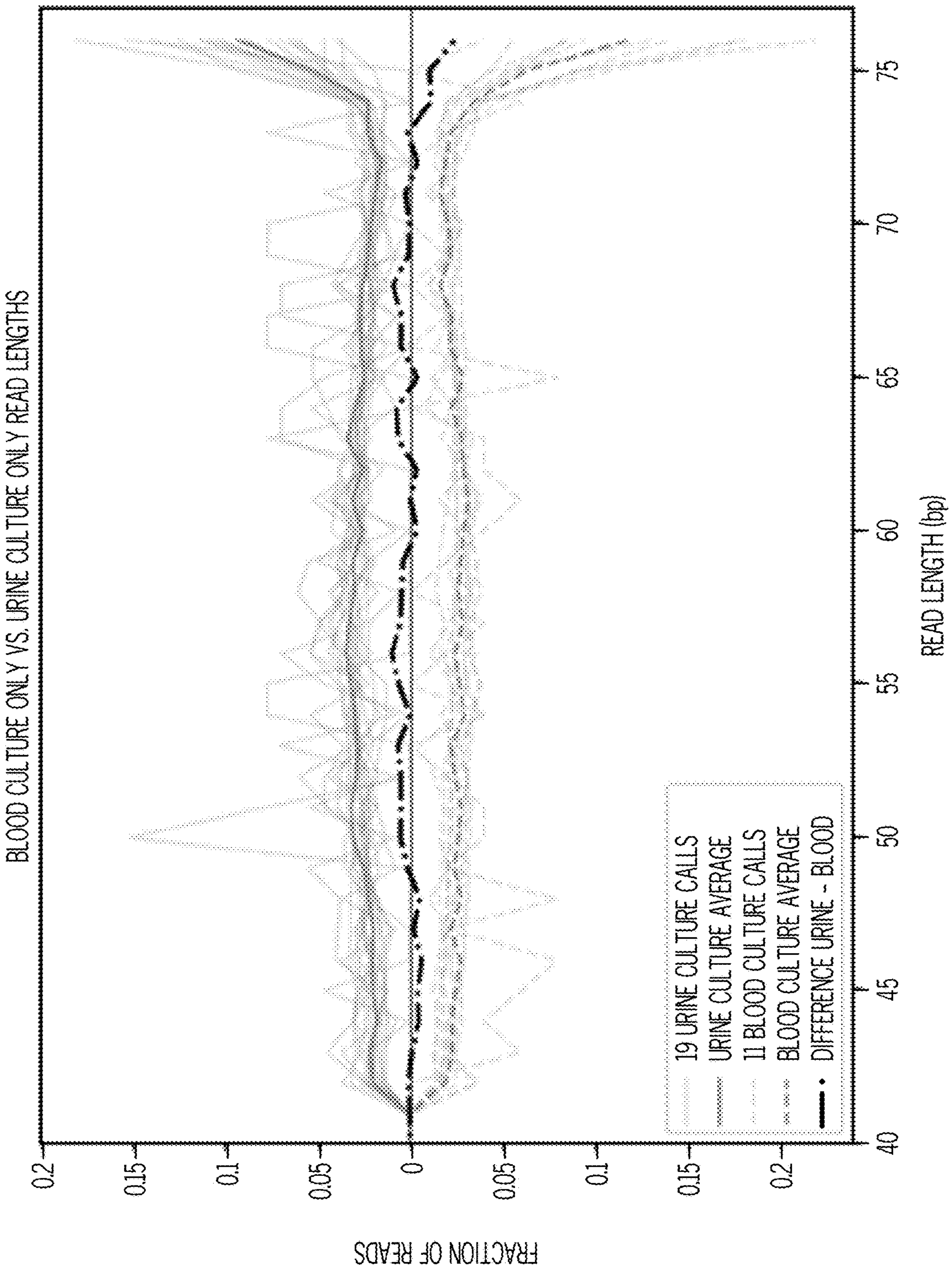
FIG. 14 provides a summary of fragment length distribution of pathogens in nucleic acid libraries generated from samples where infection was confirmed either by urine or blood cultures. Pathogens detected in nucleic acid libraries from samples with orthogonal blood culture tests show a higher fraction long reads than pathogens detected in nucleic acid libraries from samples with an orthogonal urine cultures. Read length is shown on the x-axis; fraction of reads is shown on the y-axis. The average of the urine culture samples (light solid line) and the average of the blood culture samples (light dashed line) are shown on the graph, as is the difference between urine and blood (bold dash dots).

Nineteen clinical samples were obtained from subjects that were confirmed to be undergoing an infection as determined by positive urine (n=19) and/or blood culture tests (n=11). Nucleic acid libraries were prepared from these samples and sequenced using a validated Karius Test, an extraction-based method that recovers double-stranded DNA fragments in an unbiased way in respect to their length and GC-content within a fragment length range relevant to the cell-free nucleic acids. In all nineteen subjects, the blood and urine cultures identified 19, and 11 microbes, respectively. The fragment length distribution profile shapes for the microbes detected by blood and urine cultures were evaluated. Results are shown in FIG. 14. While not being limited by mechanism, pathogen DNA coming from a deep tissue infection (lung, brain, etc.) may undergo different degradation mechanisms affecting the observed fragment length as DNA coming from a pathogen infecting the bloodstream.

Example 5. Length Distribution Profile of Host Nucleic Acids and Infection State The fragment length distribution for the host nucleic acids can help inform the non-host nucleic acid signal within a host, e.g. microbial nucleic acid signal or infection stage of a host (e.g. asymptomatic vs. symptomatic). For example, the abundance of the microbial nucleic acids within a sample from a human host can vary over several orders of magnitude (Blauwkamp et al. (2016)). While the samples obtained from asymptomatic individuals tend to exhibit lower abundances of the microbial nucleic acids as compared to the infected individuals, the abundances measured in some asymptomatic samples may exceed the lowest abundances among the infected individuals (Blauwkamp et al. (2016)). Additional properties of the nucleic acid pool obtained from a sample may help distinguish between different infectious stage or biological relationship of a microbe with the host (e.g. commensal vs. pathogenic). Here, we tested the utility of the length distribution of the host nucleic acids in predicting infection state of the microbes within a plasma from a host. Our methods enable access to endogenous fragment length profiles with fragment lengths that previous methods typically did not access in an unbiased way. Our methods also enable access to endogenous fragment length profiles with fragment lengths that previous methods typically either discarded, disregarded or deemed unimportant.

Clinical plasma samples: 100 asymptomatic (collection criteria: No active health issues related to infection, and. passed normal blood screening tests), 85 diagnostically positive (i.e. the presence of microbes confirmed with an orthogonal test, e.g.: blood culture, targeted PCR, Karius Test), and 45 diagnostically negative plasma samples were collected from human subjects. Single-centrifugation step plasma extraction process from whole blood within 24 hours of sample collection was performed for each sample, as previously described (See, Fan H C et al., PNAS 2008; 105 (42): 16266-16271, which is incorporated by reference in its entirety herein, including any drawings), and stored at −80° C. until use. Samples were then thawed, and 500 μL of each plasma was spiked with 5 μL of Spike-in Master Mix (see above). If smaller volumes were obtained, a proportionally smaller volume of Spike-in Master Mix was added to maintain a constant concentration of the process control molecules in all of the initial samples and control samples.

Positive and negative control samples were prepared as described above.

Direct-from-plasma nucleic acid library generation and sequencing: Direct to library generation was described in U.S. Provisional Application 62/770,181 filed Nov. 21, 2018, herein incorporated by reference in its entirety. The libraries were prepared and sequenced as described above in Example 1.

Figure 15A:
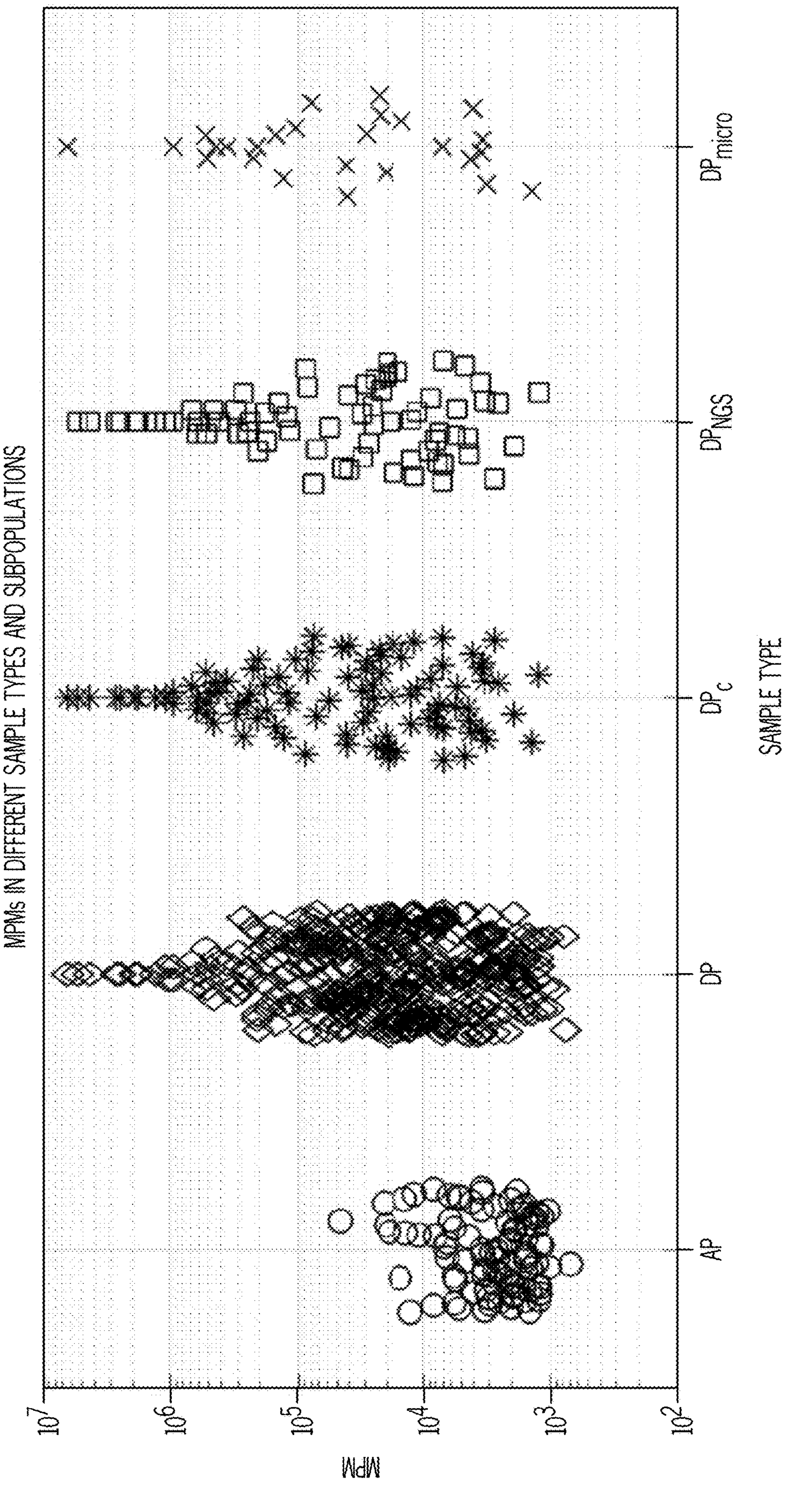
FIGS. 15A-15F summarize data obtained from asymptomatic samples (AP), diagnostic positive samples (DP), diagnostic positive samples confirmed with any orthogonal method ($DP_c$) and diagnostic positive samples confirmed with an orthogonal NGS method ($DP_{NGS}$) and diagnostic positive samples confirmed with an orthogonal non-NGS microbiological method ($DP_{micro}$) as indicated.
Figure 15B:
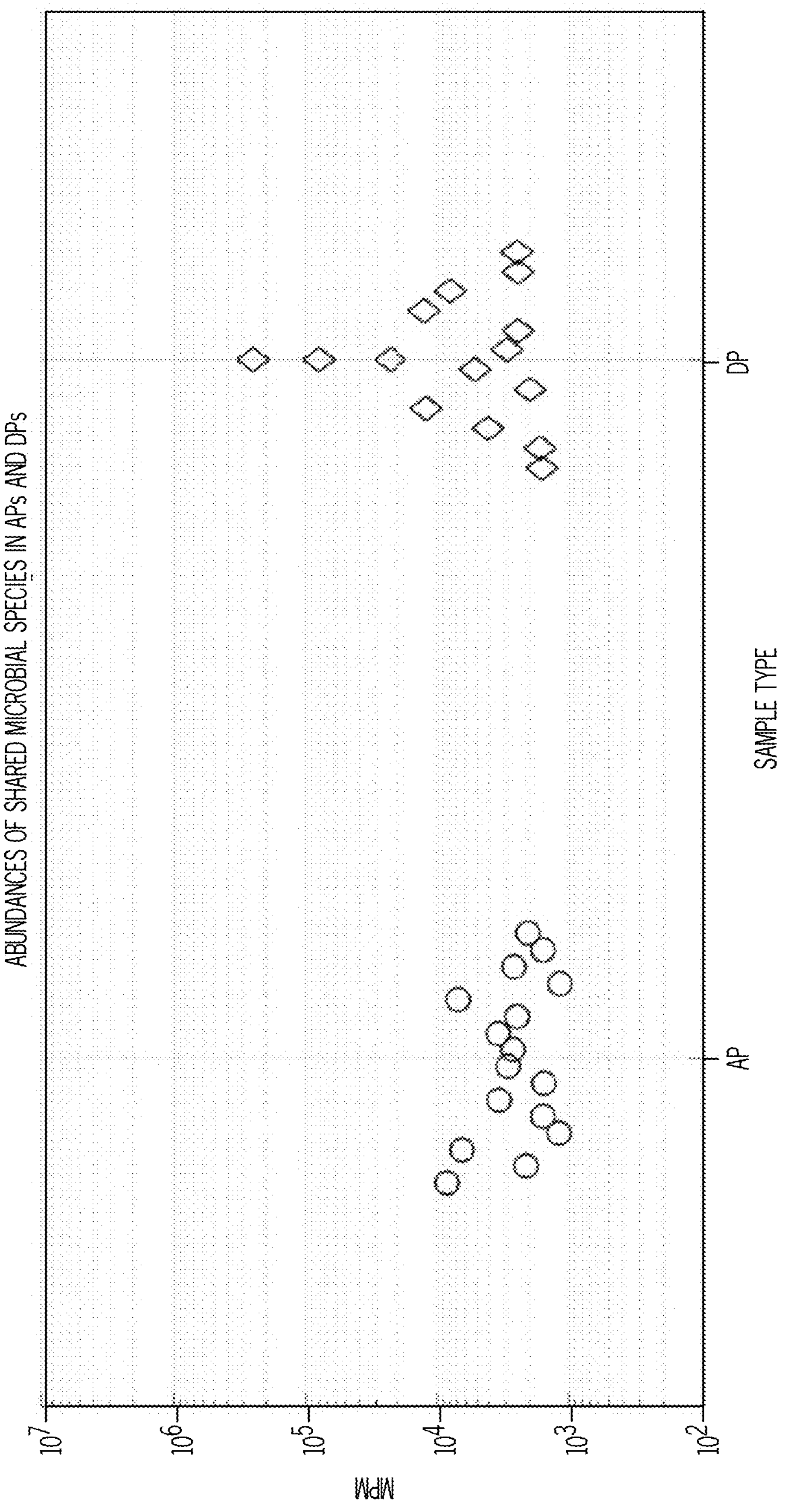

Results: The abundances of the significant microbes present in each sample were determined as described above and were given in concentration units of Molecules Per Microliter (MPM) of plasma sample, a normalized quantity that gives the estimated number of unique nucleic acid fragments for an organism in 1 microliter of plasma sample. This calculation was derived from the number of unique or deduplicated sequences present for each organism normalized to the known quantity of unique synthetic spike-ins added to plasma sample before the start of the process (See U.S. Pat. No. 9,976,181). FIG. 9A shows the distribution in MPM values in asymptomatic (AP) and diagnostic positive (DP) sample types. The lower abundance values in DP sample types overlap with the range of MPMs observed in the AP samples, even if only microbes that were orthogonally confirmed are included. ($DP_{NGS}$ includes microbes confirmed by the Karius Test and $DP_{micro}$ includes microbes confirmed by culture or PCR-based methods). Additionally, if the analysis is restricted to microbial species that are present in the set of AP samples and also in the set of DP samples (in this data set the following species fit this description: *Bacillus coagulans, Enterococcus cecorum, Enterococcus faecalis, Haemophilus influenzae, Haemophilus parainfluenzae*, Human mastadenovirus D, *Neisseria* mucosa, *Pediococcus acidilactici, Prevotella intermedia, Prevotella melaninogenica, Saccharomyces cerevisiae, Streptococcus agalactiae, Streptococcus salivarius, Streptococcus thermophilus*), abundance is still not always higher in the diagnostic positive group (FIG. 15B). Consequently, abundance is not sufficient to distinguish the infectious state of the non-microbial host.

A combination of several measurable parameters may then be used to distinguish asymptomatic/healthy patients from patients undergoing an infection. To this end, a combination of MPM microbial abundances and the distribution of the length of the nucleic acid fragments that mapped to the host reference (i.e. human reference in this cohort of samples) was investigated as a potential classifier.

Figure 15C:
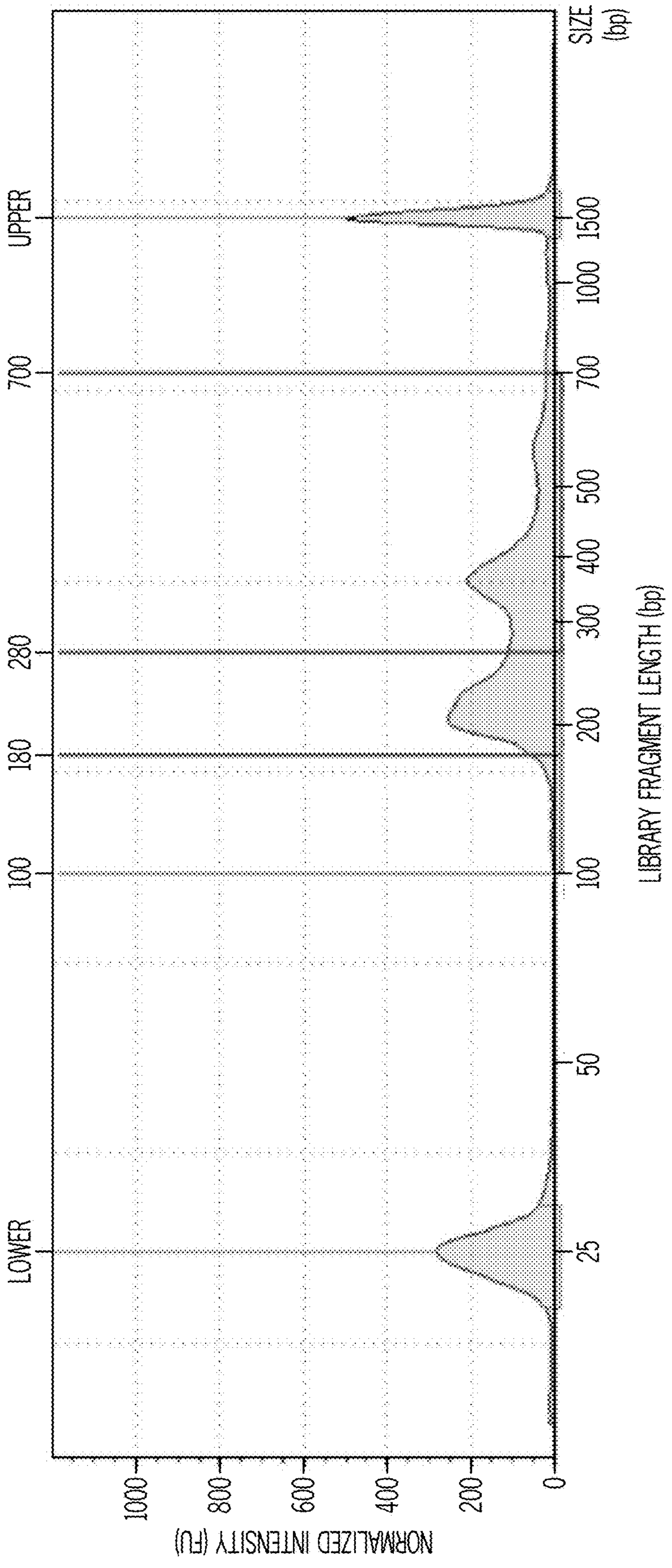
Figure 15D:
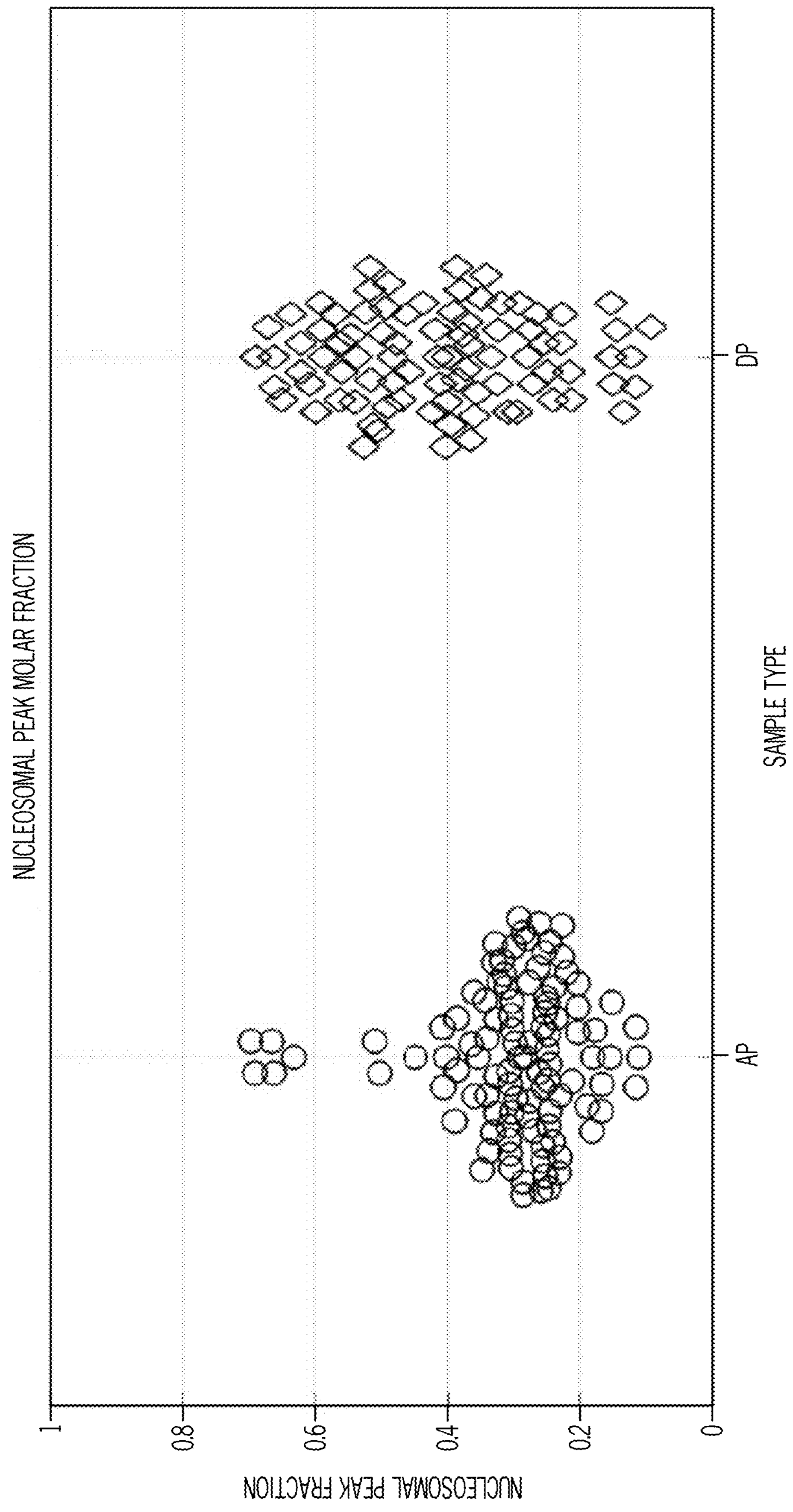

FIG. 15C shows an example of a typical distribution of nucleic acid fragments after the library generation process is completed and as measured by a TapeStation instrument. Two major peaks in fragment length can be observed: (1) a “nucleosomal” peak (300-450 bp range in the electropherogram), and (2) a “sub-nucleosomal” peak (180-280 bp range in the electropherogram). This signal is determined by the properties of the human (i.e. host) nucleic acids as the microbial (i.e. non-host) nucleic acids represent a minor fraction of the total nucleic acid population in these samples, including the DP sample types. The molar and mass ratio of the human fragments contributing to the two peaks varies between the samples and is distinctive between the AP and DP sample types (FIG. 15D). The vast majority of AP samples (92%) show the “nucleosomal” peak molar fraction to be lower than 0.4 while the same value is distributed equally over a wider range for the DP samples (<0.7).

Figure 15E:
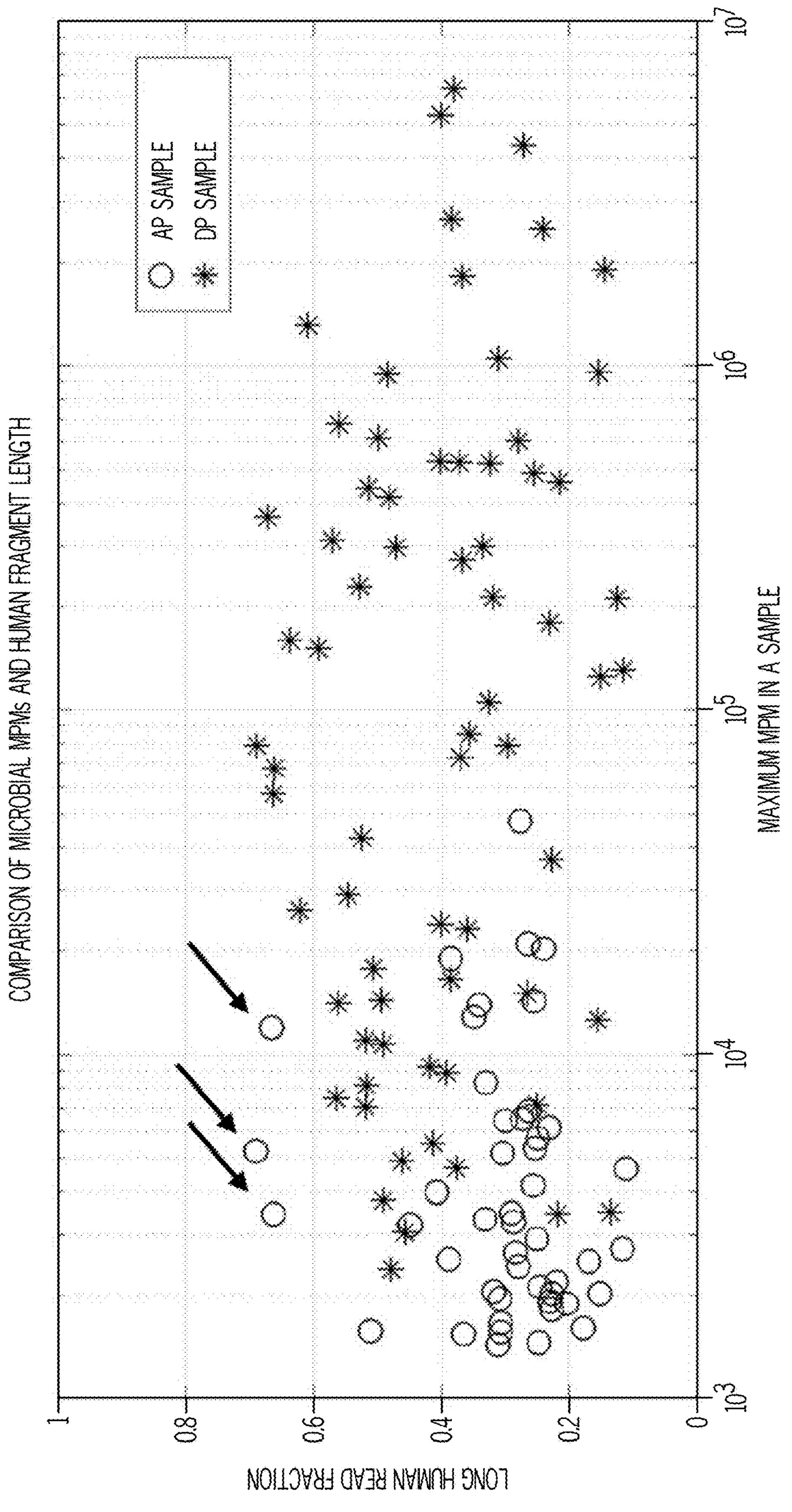

MPM microbial abundances as well as the properties of the human fragment length distribution show overlapping values between AP and DP samples. A combination of the two independent measurements may help distinguish the asymptomatic calls from the infectious calls in an unknown sample where the infectious stage is unknown. FIG. 15E shows the long human reads fraction as measured from the sequencing data (all reads mapping to human reference longer than 65 bp after adapter trimming) and maximum MPM value measured in the same sample for all AP and DP samples. The region encompassed by the coordinates [(0, 3000), (0,0.4)] is populated by AP samples exclusively. Three of the 100 AP samples fall outside of this space (arrows in FIG. 15E). The microbes detected in these three samples were *Helicobacter pylori*, Human mestadenovirus D, and *Nisseria gonorrhoeae*. All three microbes are known human pathogens, though we do not know whether they were pathogenic in these individuals.

Figure 15F:
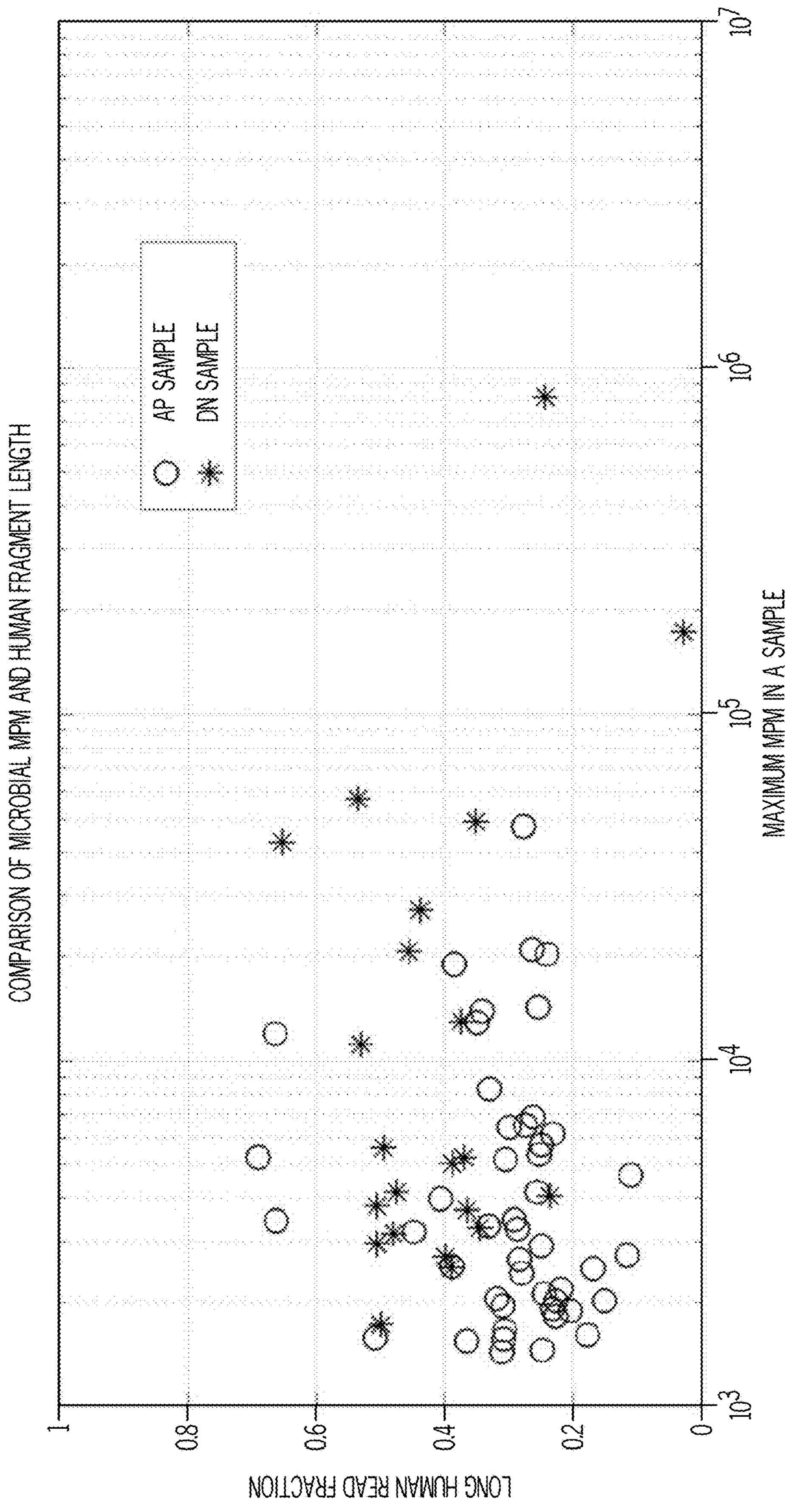

A comparison between microbial MPM and the properties of the human fragment length distribution in AP and DN samples types (FIG. 15F) reveals that none of the DN samples fell within a typical asymptomatic range even though they were negative according to the orthogonal testing.

Non-microbial signal such as e.g. properties of the fragment length distribution for the non-microbial host nucleic acids can be utilized in identification of asymptomatic or non-infectious states of a subject.

The data also indicates that the asymptomatic individuals can be identified from data such as presented here by combining the abundances (e.g. maximum MPM) and fragment length distribution parameters, even if the MPM values for the microbes overlap with the range that can be observed in the diagnostic positive samples. It also suggests that an early detection of the infection may be possible in the absence of standard symptoms. The region on such a two-dimensional plane that can help distinguish between different infectious states of individuals can be further optimized in respect to e.g. MPMs for specific microbial species, or kingdom as well as microbial fragment length for improved performance of the test.

Figure 16A:
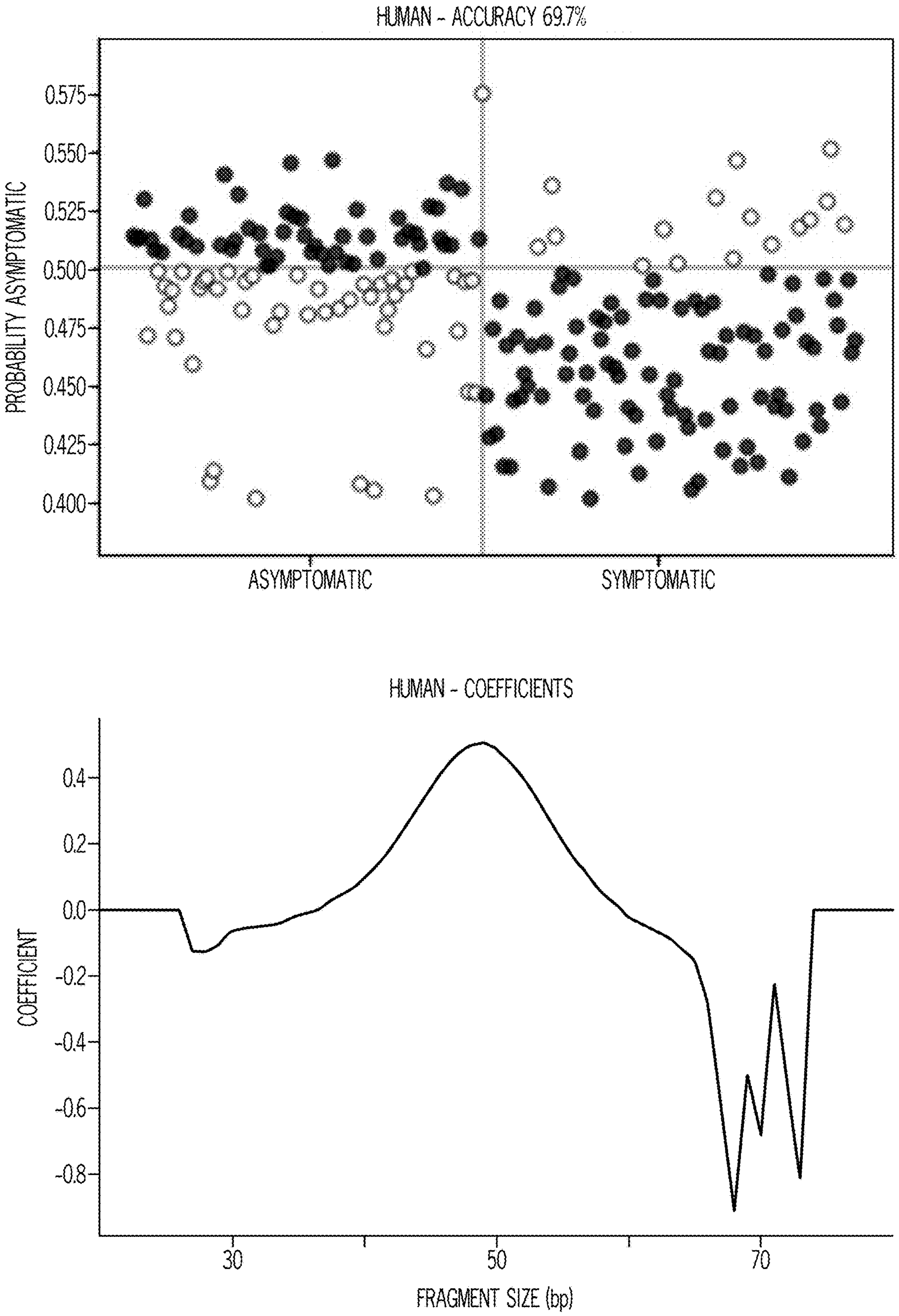
FIG. 16A depicts the results of training a predictor of an infection state based on the human fragments recovered for sequencing from asymptomatic and symptomatic patients. The left panel shows probabilities for a sample to be asymptomatic based on human-trained model. The right panel depicts the regions of the fragment lengths relevant to each infection state used by the human-trained model.
Figure 16B:
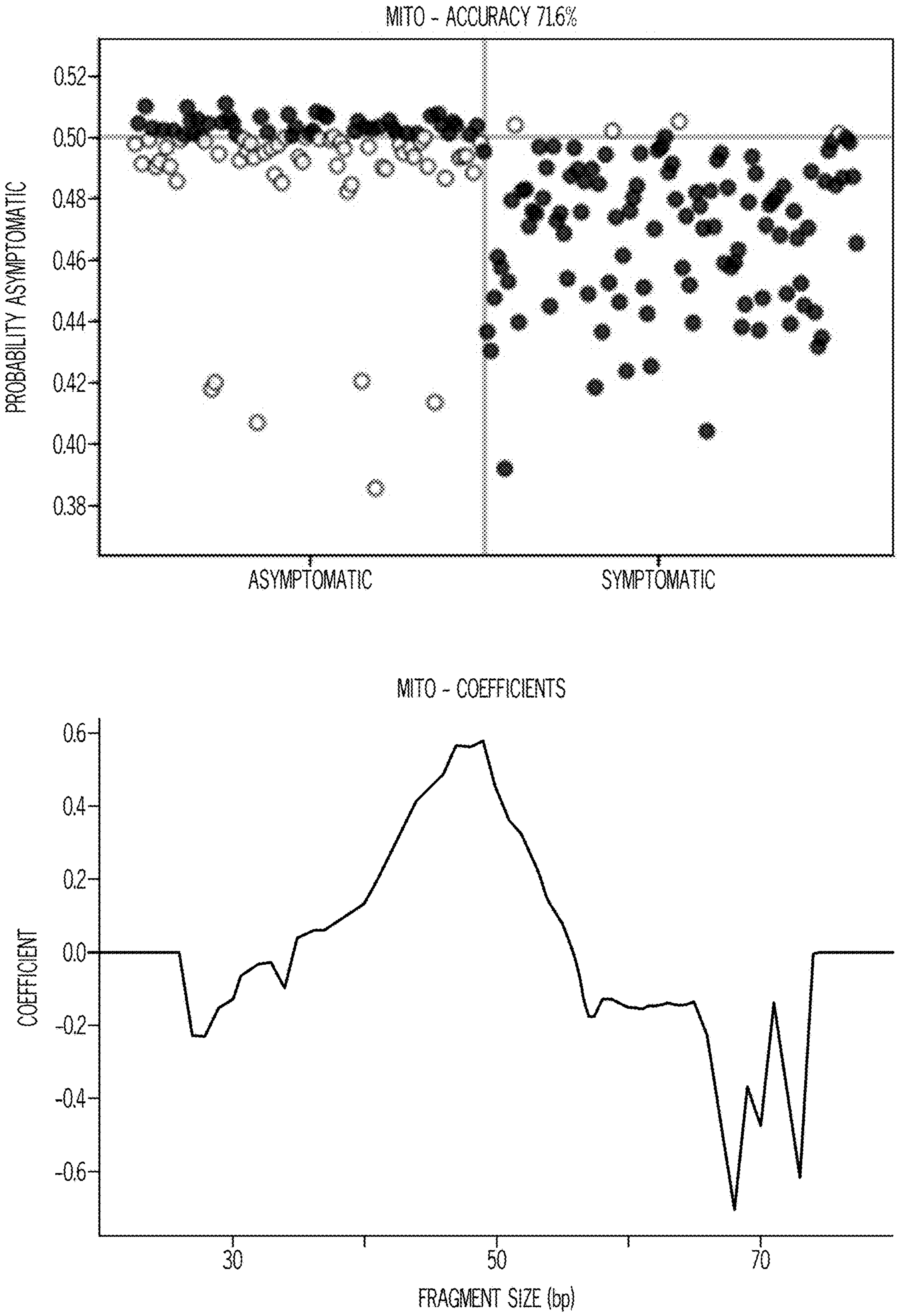
FIG. 16B depicts the results of training a predictor of an infection state based on the human mitochondrial fragments recovered for sequencing from asymptomatic and symptomatic patients. The left panel shows probabilities for a sample to be asymptomatic based on human mitochondria-trained model. The right panel depicts the regions of the fragment lengths relevant to each infection state used by the human mitochondria-trained model.
Figure 16C:
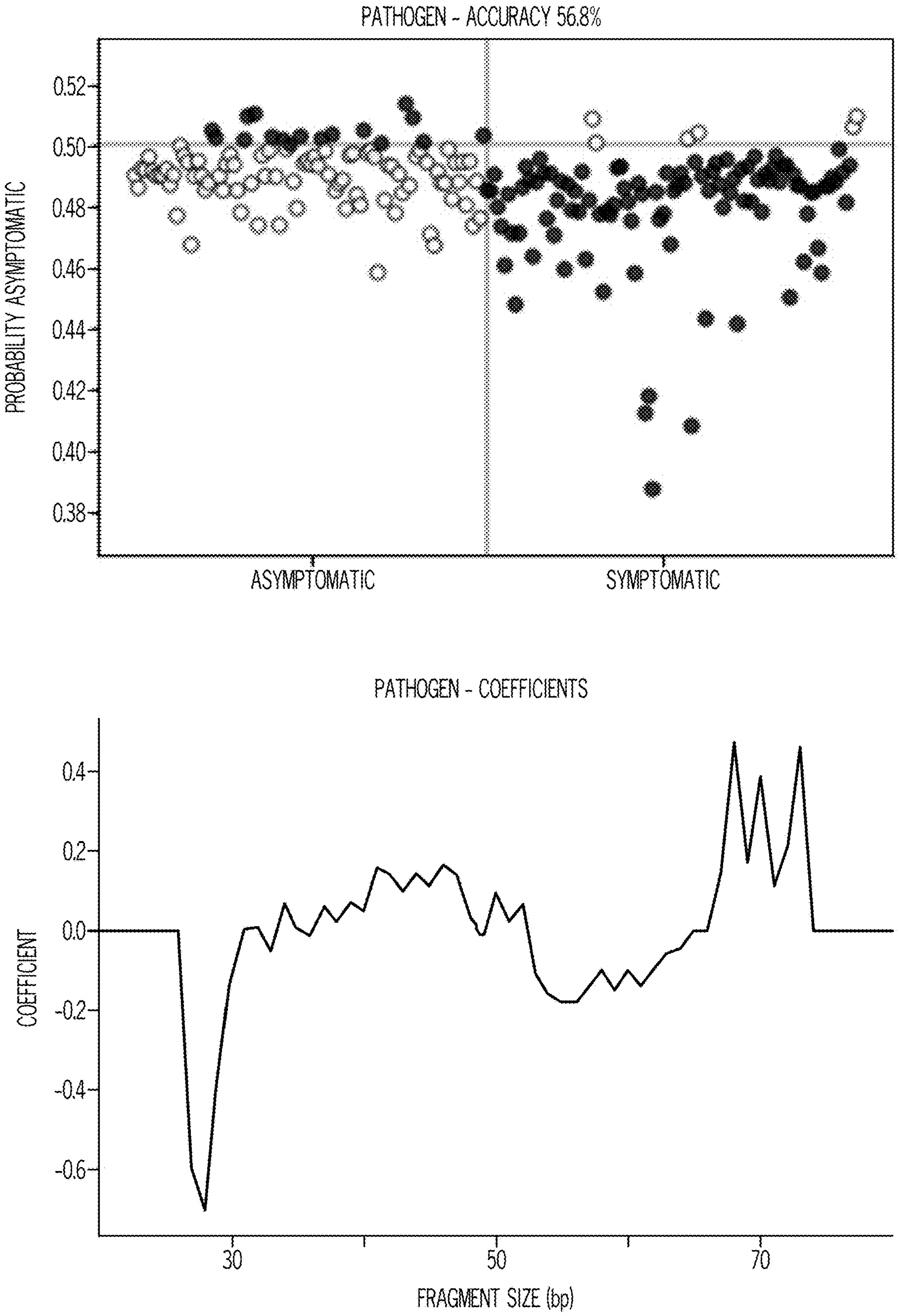
FIG. 16C depicts the results of training a predictor of an infection state based on the all pathogen fragments recovered for sequencing from asymptomatic and symptomatic patients. The left panel shows probabilities for a sample to be asymptomatic based on all pathogen fragment-trained model. The right panel depicts the regions of the fragment lengths relevant to each infection state used by all pathogen fragment-trained model.
Figure 16H:
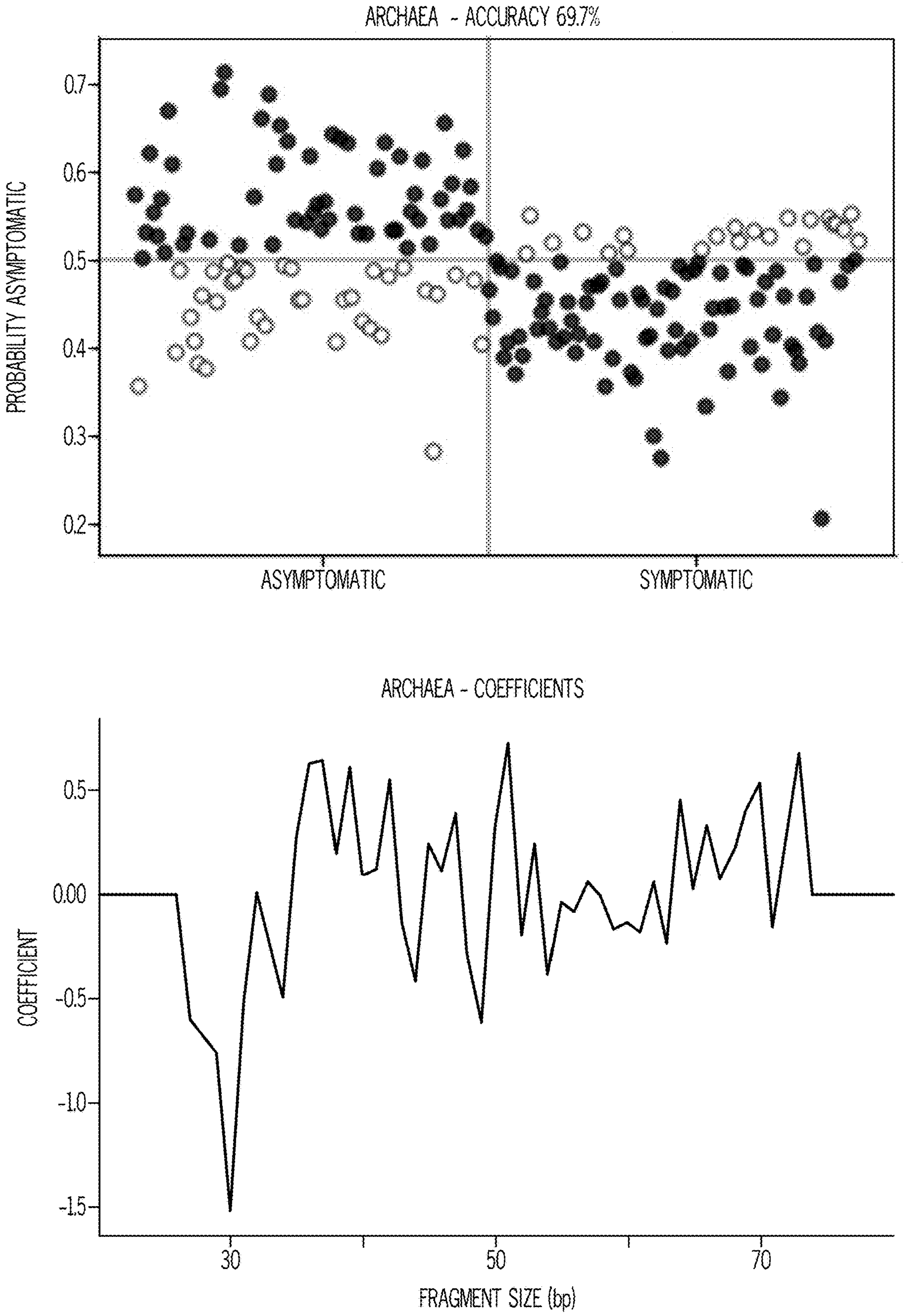
FIG. 16H depicts the results of training a predictor of an infection state based on the archaea fragments recovered for sequencing from asymptomatic and symptomatic patients. The left panel shows probabilities for a sample to be asymptomatic based on archaea-trained model. The right panel depicts the regions of the fragment lengths relevant to each infection state recognized by the archaea-trained model.

Finally, the normalized size distribution of fragments aligning to the human genome (dominated by the nuclear genome), human mitochondrial genome, all pathogens, significant pathogens; and bacteria, eukaryotes, viruses and archaea were computed for all samples. To differentiate AP from DP/DN samples a classifier was trained on the fragment size distributions (features), in this case by using logistic regression with L2 regularization. Logistic regression is a linear model for classification that multiplies features by a set of weights prior to transformation with a logistic function. The weights are determined using standard numerical optimization techniques with L2 regularization providing an additional constraint to minimize the sum of the squares of the weights. This has the effect of decreasing overfitting and effects of multicollinearity in the features. The accuracy of this model is assessed by using the trained model to predict the probability that each sample is asymptomatic or symptomatic. Values >0.5 indicate that the sample is predicted to be asymptomatic, values <0.5 indicate that the same is predicted to be symptomatic. Additionally, the trained model provides the weights (coefficients). Positive coefficients indicate association with asymptomatic individuals, negative coefficients with symptomatic ones. FIG. 16 shows the accuracy of predicting an asymptomatic and symptomatic infection state based training using the normalized size distribution of fragments aligning to the human genome (dominated by the nuclear genome), human mitochondrial genome, all pathogens, significant pathogens; and, bacteria, eukaryotes, viruses and archaea. The subgroup of nucleic acids from the library used to train the model affects the accuracy of the model. In addition, the subgroup of nucleic acids from the library affects the regions of the fragment length distribution that have a positive predictive value for either asymptomatic or symptomatic state. For example, the presence of long human fragments (>60 bp)

predicts a symptomatic state (FIG. 16A, right panel) as do short (<30 bp) pathogenic fragments (FIG. 16C, right panel). On the other hand, high concentration of fragments around 50 bp predicts an asymptomatic state (FIG. 16A, right panel) as do long (>65 bp) pathogenic fragments (FIG. 16C, right panel).

Example 6. Distinguishing Asymptomatic Patients Colonized by *H. pylori* vs. Patients with Active *H. pylori*-Associated Inflammation Plasma processing and DNA extraction: Plasma is extracted from whole blood samples within 24 hours of sample collection, as previously described (Fan H C et al., PNAS 2008; 105 (42): 16266-16271), and is stored at −80 −∞C. When required for analysis, plasma samples are thawed and circulating DNA is immediately extracted from 0.5-1 ml plasma.

Sequencing library preparation and sequencing: Sequencing libraries are prepared from the purified patient plasma DNA using the NEBNext® DNA Library Prep Master Mix Set for Illumina® with standard Illumina® indexed adapters (purchased from IDT) and post-end repair purification (e.g., Mag-Bind® beads, NEBNext® End Repair Module), or using a microfluidics-based automated library preparation platform (Mondrian ST, Ovation SP Ultralow library system). Libraries are characterized using the Agilent® 2100 Bioanalyzer (High sensitivity DNA kit) system for library analysis and quantified by qPCR.

qPCR Validation of Sequencing Results for Selected Bacterial Targets. Standard qPCR kits for the quantification of selected bacterial targets (e.g., *H. pylori*) are used to validate the sequencing results for a subset of cell-free DNA samples. The qPCR assays are run on cfDNA extracted from ~1 ml of plasma and eluted in a 100 ml Tris buffer (50 mM [pH 8.1-8.2]). The plasma extraction and PCR experiments are performed in different facilities. No-template controls are run to verify that the PCR reagents are included in every experiment.

After removing low-quality reads, reads are mapped to the human reference genome. Remaining reads, presumed to be microbiome-derived, are mapped to a reference database of target microorganism genomes. Relative abundance for each microorganism are calculated using a proprietary algorithm. The algorithm reports organisms that are present at statistically significant amounts as compared with controls. Organisms with over-represented sequences are reported as positive.

Quality control (QC) measures included adding an ID-spiked-in synthetic nucleic acid, which is a type of spike-in that is unique for each sample in a sequencing batch, and other synthetic nucleic acid spike-ins ("SPANK molecules") which are spiked in at a constant concentration across all libraries. Thus, the number of deduplicated SPANK molecules detected in a particular library is a proxy for the minimum concentration detectable in that library. This can be useful for setting a threshold based on minimum concentration of the SPANK molecules detectable in that library. The threshold can be useful to ensure sufficient sequencing depth for detection of pathogen. The threshold can also be useful in making sure that pathogen signal was not due to cross contamination from other samples. For example, enrichment of pathogens relative to the threshold set by the SPANK molecules can be compared between different samples. More generally, it is proportional to the efficiency with which that library converted DNA molecules in the original sample to reads in the DNA sequencing data. The purpose of the SPANK molecules is to help establish the relative abundance of the pathogen molecules within the mixture represented in a specimen, reported as "molecules per ml" (MPM). MPM data was used to build heatmaps and correlation plots. Sample Purity Ratio (SPR) aims to capture how significant the number of taxon-associated reads is given the estimated degree of cross-contamination in the sample. In case of failure of deduplicated SPANK and/or SPR, the sample was re-queued and re-run once. If QC failed twice on the same sample, the report was "no result."

Results.

The method is able to detect *H. pylori* cell-free DNA in plasma obtained from patients with *H. pylori*-associated peptic ulcer disease. The method was able to distinguish between patients with asymptomatic *H. pylori* and *H. pylori* disease. For the later case, the samples were obtained from healthy (i.e., asymptomatic) and infected subjects and analyzed using next-generation sequencing of cell-free plasma to detect pathogen DNA (The Karius Test™, Karius, Redwood City, CA). In healthy volunteers, the test detected *H. pylori* in 8/106 samples assayed. Some patients identified in the dataset with an *H. pylori* asymptomatic colonization (C) (n=1) or an *H. pylori* symptomatic, chronic infection (CI) (n=7) (see, Table 1, below). *H. pylori* positive samples were associated with African-American or Hispanic race which is consistent with the epidemiology of *H. pylori* infection.

TABLE 1

Detection of *H. pylori* in plasma. *H. pylori* Infections as Probable, Possible or Unlikely Causes of Sepsis

| Subject ID | *H. pylori* MPM | Type of Patient | Infection Type | Classification of Infection as Primary Etiology of Sepsis | Relevant Clinical Characteristics |
|---|---|---|---|---|---|
| SFN0032 | 110.17 | Neutropenic fever | Acute | Possible | Immunocompromised patient, result adjudicated to possible addition of *H. pylori* antibiotic coverage |
| 599074 | 196.83 | Suspected Sepsis | Acute | Probable | |
| 111629 | 104.65 | Suspected Sepsis | Chronic | Unlikely | |
| 162140 | 125.21 | Suspected Sepsis | Chronic | Unlikely | |

TABLE 1-continued

Detection of *H. pylori* in plasma. *H. pylori* Infections as Probable, Possible or Unlikely Causes of Sepsis

| Subject ID | *H. pylori* MPM | Type of Patient | Infection Type | Classification of Infection as Primary Etiology of Sepsis | Relevant Clinical Characteristics |
|---|---|---|---|---|---|
| 185478 | 38.74 | Suspected Sepsis | Chronic | Unlikely | |
| 562626 | 176.90 | Suspected sepsis | Chronic | Unlikely | |
| 562871 | 87.73 | Suspected sepsis | Chronic | Unlikely | |
| 564748 | 71.03 | Suspected sepsis | Chronic | Unlikely | |
| 758884 | 106.19 | Suspected sepsis | Chronic | Unlikely | |
| 263403 | 243.29 | Suspected sepsis | Chronic | Unlikely | |

Without being limited by mechanism, cell-free nucleic acids may be derived from pathogens that are dead and dying. Thus, the present method is uniquely suited to detect organisms that are being actively cleared by the immune system. In fact, the assay was able to distinguish between *H. pylori* in the context of active inflammation rather than asymptomatic colonization.

Example 7: Method to Detect *H. pylori* GI Tract Infection Among High-Risk Patients The objectives of this study are to assess the clinical utility of the present method (i) to detect active *H. pylori* infection compared to conventional diagnostic tests in patients symptomatic for peptic ulcer disease (*H. pylori* PUD); (ii) to confirm eradication for active *H. pylori* gastrointestinal infection compared to conventional diagnostic tests after first-line therapies; and (iii) assess optimal MPM thresholds distinguishing patients with active *H. pylori* PUD from those without (asymptomatic). Using this non-invasive method allows physicians to make effective treatment decisions without resorting to traditional, invasive diagnostic methods.

Study Design.

The positive percent agreement (PPA) and negative percent agreement (PA) of the present method compared to non-serology conventional *H. pylori* diagnostic tests in two well-described adult study populations under specific test conditions are determined as described below herein At study entry, patients with symptomatic *H. pylori* PUD meeting clinical criteria and have at least one positive protocol-approved, non-serology, conventional *H. pylori* diagnostic test prior to any administration of primary eradication treatment. A plasma test is performed on all documented symptomatic *H. pylori* PUD patients. Thereafter, these PUD patients receive a 2-4 week standard eradication regimen (as per standard of care) followed by 1 month drug holiday. At 30 days (+/−3 days) after completion of primary treatment, all PUD patients at the end of study participation undergo a repeat plasma test evaluation and at least one of the original non-serology, conventional *H. pylori* diagnostic tests performed prior to treatment.

At study entry, negative control patients undergoing colonoscopy for any reason have no evidence of active *H. pylori* gastrointestinal disease based on clinical criteria and at least one negative protocol-approved, non-serology conventional *H. pylori* diagnostic test during screening. Thereafter, negative control colonoscopy patients have a plasma test performed to complete all protocol requirements.

Data from these diagnostic test comparisons provide insights as to the clinical utility of the present method to detect active *H. pylori* disease and to confirm eradication after primary treatment compared to non-serology conventional *H. pylori* diagnostic tests.

Methods and Materials

The quantitative testing method is used to detect microorganisms through the analysis of non-human DNA in blood plasma. The analyte for this method is microorganism cell-free nucleic acid, which is very short (averaging less than 100 nucleotides in length) as compared to human cfDNA.

Whole blood is centrifuged twice to render cell free (cf) plasma. To address the potential for environmental contaminants, non-volatile buffers may be heated to a temperature in excess of 85° C. and cooled prior to use. Internal control molecules are added to each sample after the first centrifugation using the methods set forth in PCT-US2017-024176. The plasma is extracted, and purified cell free DNA (cfDNA) used to prepare sequencing libraries using the NEBNext® DNA Library Prep Master Mix Set for Illumina® with standard Illumina® indexed adapters (purchased from IDT) and post-end repair purification (e.g., Mag-Bind® beads, NEBNext® End Repair Module), or using a microfluidics-based automated library preparation platform (Mondrian ST, Ovation SP Ultralow library system). Adapters are ligated and purification performed without heat using AMPure® Beads, before amplification by qPCR. Libraries are characterized using the Agilent® HS TapeStation, and total concentrations of nucleic acids measured to control loading volumes for size selection step by integrating the signal (e.g., between 50 bp and 1000 bp.

The sequenced cfDNA fragments are mapped to a reference database of microbial sequences to determine the identity of non-human, non-internal control material present in the sample at significant levels (above the background of the assay). The sequencing data is first transformed into reads representing DNA sequences, and then de-multiplexed based on index sequences into collections of reads (readsets) derived from each library loaded onto the sequencer. Reads that align with human sequences are filtered, and the remaining reads that align to the sequences of internal control molecules are set aside for additional analyses. Next, reads matching neither the human nor internal control references are aligned to known microbial genomes. Reads with one or more alignments to this database (pathogen reads) are the basis of subsequent analysis.

The alignments of each pathogen read to the microbial genome database are used to infer the relative abundances of each taxon associated with the reference sequences. These abundances are aggregated up the taxonomy tree to give abundances at all taxonomic ranks. Finally, the abundances in clinical samples are compared to the abundances in negative control libraries on the same sequencing run to determine whether they rise above the background level expected due to environmental DNA contamination. Taxa meeting this criterion are reported in units of molecules per milliliter (MPM) based on a ratio of the abundance of microorganism reads and certain internal control reads obtained. Before resulting, the pipeline applies a set of filters to limit the reportable organisms to those that are greater than, for example 3-10% of the microorganism with the highest number of reads and greater than, for example 25-50% of any other taxonomic family related organism. The filter is applied for all patient samples and assay controls.

Potential sources of performance bias from sample-specific or microbe-specific properties include the class of microorganism-specific properties include the class of microorganism (e.g., bacteria, virus, eukaryote, prokaryote, fungus, etc.), GC-content, genome size, abundance in endogenous microflora, environmental contamination (EC) levels, and reference assembly number and quality of data. To address these sources of bias, this method includes use of a representative panel of 10-100 microorganisms that capture the full spectrum of potential performance bias along GC content, genome size and strain. These representative organisms should span kingdoms, range in GC content (e.g., from 10%-80%), and have genomes that range from kilobases to megabases. The representative population should include a mix of types, such as commensals and non-commensals, microbes commonly found as environmental contaminants, and closely related strains. The method additional incorporates standard quality control measures, such as reference intervals for levels of microorganisms in a healthy population and EC negative controls.

The test will be considered positive if the test shows *H. pylori* levels to be significant against negative background controls. Note however, negative percent agreement (NPA) is not likely to be reflective of the NPA of the test after we account for the quantitative MPM cut-off.

In addition to assessment of PPA and NPA within each of the study cohorts, PUD and colonoscopy, using the threshold in MPM for positive and negative as determined via the lab, other thresholds in MPM will also be considered. First, MPM will be summarized with means, standard deviations, medians and ranges for each study cohort. Second, receiver operating characteristic (ROC) curves will be used to identify optimal cut points in MPM for maximizing PPA and NPA in the samples.

Finally, to assess the ability of present method to identify eradication at 30 days, successful eradication will be estimated with proportions and 95% confidence intervals within each of the study cohorts.

Example 8. Fragment Length Distribution Profile and Site of Localization

The characteristics of the fragment length distribution of the microbial sequencing reads obtained from the clinical samples from patients with an infection located in the bloodstream and in the lungs, as an example of a deep-tissue infection were compared. Fragment length distribution characteristics vary depending on the site of localization. Without being limited by mechanism, different host responses at different sites of infection may contribute to varying fragment length distribution characteristics. Again without being limited by mechanism, different sites of infection may exhibit different non-host nucleic acid fragmentation mechanisms.

Clinical plasma samples: 10 deidentified clinical samples from patients with a confirmed bloodstream infection, and 10 deidentified clinical samples from patients with a confirmed lung infection were collected. Single-centrifugation step plasma extraction process from whole blood within 24 hours of sample collection was performed for each sample, as previously described (See, Fan H C et al., PNAS 2008; 105 (42): 16266-16271, which is incorporated by reference in its entirety herein, including any drawings), and stored at −80° C. until use. Samples were then thawed, and 150 μL of each plasma was spiked with 1.5 μL of Spike-in Master Mix (see below). If different volumes were obtained, a proportionally smaller or higher volume of Spike-in Master Mix was added to maintain a constant concentration of the process control molecules in all of the initial samples and control samples.

Negative Control Samples: Four 500 μL negative control samples (EC) were made from aqueous buffer (10 mM Tris pH 8, 0.1 mM EDTA, 0.05 v/v % Tween-20®) with 5 μL of Spiked-in Master Mix (see below) and served as control for environmental contamination (i.e., microbe and pathogen nucleic acid contamination introduced by either the reagents, instrumentation, consumables, operators, and/or air during processing). These synthetic nucleic acids are later used for normalizing the signal in the samples in order to account for variations in sample processing.

A Spike-In Master Mix was prepared as described above herein with ID-Spike Molecules, SPANK molecules and SPARK molecules.

A ligation-based direct-to-library process as described in Example 1 of U.S. Provisional App. 62/770,181 was used to prepare a sequencing library from 5 ul spiked asymptomatic plasma. Sequencing and sequencing data analysis was performed as described in Example 8.

Results: Table 2 lists all 20 clinical samples processed as part of this example together with the site of infection and the species of the infecting microbe for each subject that donated the clinical sample. The fragment length distributions for the infecting microbes in all the tested samples are shown in FIG. 17. The normalized fragment length distributions for the reads mapping to the infecting microbes' references were analyzed for the presence of fragment length distribution profile characteristics (e.g. short exponentially decaying fragments, Peak, Long fragments): (1) short exponential-like distributed fraction ("Short" in Table 2), (2) peak fraction ("Peak" in Table 2), and (3) Fraction of reads longer than the read length of the experiment (75 bp; "Long" in Table 2). Also, fractions of the typical length ranges in microbial fragment length distributions. A comparison of the fragment length distribution profile types revealed that the infections of the bloodstream disproportionately exhibit a fragment length distribution profile characterized by (1) a high fraction of the short pseudo-exponentially distributed fragments, (2) the absence of a peak between 20 bp and 75 bp read lengths, and (3) a fraction of long reads (>64 bp) greater than 10% in. Conversely, the infections of the lungs disproportionately exhibit a fragment length distribution profile characterized by (1) a presence of the short pseudo-exponentially distributed fragments, (2) the presence of a peak between 20 bp and 75 bp read lengths, and (3) fraction of the long reads smaller than 10%. This suggests that the features of the microbial fragment length distributions can be used to determine whether the infection is present in the bloodstream or in deep tissue.

TABLE 2

List of the clinical samples and the site of infection, the species of the infecting microbe, and the properties of the fragment length distribution for the sequencing reads mapping to the reference of the infecting microbial species. For each property, its qualitative assessment (present/absent) is indicated and the fraction of total reads that exists in that segment is given in parentheses. Here, the short fragment section includes reads from 22 bp up to and including 29 bp; the Peak fragment length range includes reads from 30 bp up to and including 59 bp; and long fragment range includes reads longer than 59 bp.

| Sample ID | Site of Infection | Species of the Infecting Microbe | Fragment Length Distribution Features: Short | Peak | Long |
|---|---|---|---|---|---|
| RD-19543 | Lungs | *Pseudomonas aeruginosa* | Present (0.14) | (0.50) | Present (0.36) |
| RD-19553 | | *Streptococcus pyogenes* | Absent (0.36) | Present (0.84) | Absent (0.12) |
| RD-19554 | | *Candida parapsilosis* | Absent (0.08) | Present (0.85) | Absent (0.07) |
| RD-19557 | | *Enterococcus faecalis* | Absent (0.05) | Present (0.69) | Absent (0.26) |
| RD-19539 | | *Candida dubliniensis* | Absent (0.09) | Present (0.51) | Present (0.40) |
| RD-19552 | | *Staphylococcus epidermidis* | Present (0.21) | Present (0.73) | Absent (0.06) |
| RD-19556 | | *Staphylococcus epidermidis* | Present (0.14) | Present (0.70) | Absent (0.16) |
| RD-19555 | | *Escherichia coli* | Present (0.10) | Present (0.71) | Absent (0.19) |
| RD-19550 | | *Stenotrophomonas maltophilia* | Present (0.16) | Present (0.68) | Absent (0.16) |
| RD-19540 | | *Staphylococcus aureus* | Present (0.34) | Present (0.63) | Absent (0.03) |
| RD-19544 | Blood-stream | *Staphylococcus aureus* | Present (0.42) | Absent (0.56) | Absent (0.02) |
| RD-19548 | | *Staphylococcus epidermidis* | Present (0.14) | Absent (0.50) | Present (0.36) |
| RD-19547 | | *Candida parapsilosis* | Present (0.15) | Absent (0.67) | Present (0.18) |
| RD-19545 | | *Pseudomonas aeruginosa* | Present (0.14) | Absent (0.49) | Present (0.37) |
| RD-19551 | | *Escherichia coli* | Absent (0.04) | Present (0.90) | Absent (0.07) |
| RD-19542 | | *Streptococcus pyogenes* | Absent (0.05) | Present (0.88) | Absent (0.07) |
| RD-19546 | | *Staphylococcus epidermidis* | Absent (0.01) | Present (0.86) | Absent (0.13) |
| RD-19541 | | *Candida dubliniensis* | Absent (0.09) | Present (0.68) | Present (0.23) |
| RD-19558 | | *Enterococcus faecalis* | Present (0.17) | Present (0.69) | Absent (0.14) |
| RD-19546 | | *Stenotrophomonas maltophilia* | Present (0.12) | Present (0.66) | Absent (0.22) |

Example 9. Fragment Length Distribution Profile and Site of Localization 2

The characteristics of the fragment length distribution of the microbial sequencing reads obtained from the clinical samples from patients with an infection located in the bloodstream (plasma from a venous blood draw) and plasma from capillary blood that came into contact with the skin on the fingertip prior to collecting it in the capillary draw collection system, as an example of a skin infection were compared.

Clinical plasma samples: Blood from 20 healthy adult donors was collected into a PPT tubes with K2EDTA as the anticoagulant (Becton Dickinson, Franklin Lakes, NJ) according to the manufacturer's instructions. Immediately following the venous blood draw, a capillary blood draw was performed on the same group of 20 healthy donors using Microvette® CB300 blood sampling devices using K2EDTA as the anticoagulant (Sarstedt Inc, Sparks, NV). The following procedure was applied during the capillary draw: (1) The donor's finger was held in an upward position and lanced the palm-side surface of the finger with proper-size lancet, (2) Pressing firmly on the finger when making the puncture was avoided to prevent hemolysis of the drawn blood, and (3) the blood droplet spread over the fingertip was collected into a clean Microvette® CB300 blood sampling device. A single-centrifugation step plasma extraction process from whole blood within 12 hours of sample collection was performed for each sample according to the manufacturer's instructions, and plasma stored at −80° C. until use. Samples were then thawed, and each plasma was spiked with the volume of Spike-in Master Mix equal to 1% of the plasma volume.

Negative Control Samples: Four 500 µL negative control samples (EC) were made from aqueous buffer (10 mM Tris pH 8, 0.1 mM EDTA, 0.05 v/v % Tween-20®) with 5 µL of Spiked-in Master Mix (see below) and served as control for environmental contamination (i.e., microbe and pathogen nucleic acid contamination introduced by either the reagents, instrumentation, consumables, operators, and/or air during processing). These synthetic nucleic acids are later used for normalizing the signal in the samples in order to account for variations in sample processing.

Negative Microvette® Samples: Four 300 µL of aqueous buffer (10 mM Tris pH 8, 0.1 mM EDTA, 0.05 v/v % Tween-20®) was added into four clean and unused Microvette® CB300 blood sampling devices and incubated for 6 hours at room temperature before collecting quantitatively the content and spiking with 3 µL of Spiked-in Master Mix (see below).

A Spike-In Master Mix was prepared as described above herein with ID-Spike Molecules, Spank molecules and Spark molecules.

Direct-from-plasma nucleic acid library generation: 25.0 µL of each spiked sample was mixed with 10.0 µL of 10× Terminal Transferase Reaction Buffer (NEB, Ipswich, MA), 2.5 µL of Proteinase K protease (Sigma-Aldrich®), 1.0 µL of 10% Tween-20® (Thermo Fisher Scientific®, Waltham, MA), 1.0 µL of 10% Triton X100 (Thermo Fisher Scientific®, Waltham, MA) and 60.5.0 µL Nuclease-free water. The mixture was heated to 60° C. for 20 minutes and 95° C. for 10 minutes and placed on ice until cool. 1.0 µL of 10 mM dATP, 1.0 µL Terminal Transferase (20 u/µL, NEB, Ipswich, MA) and 3.0 µL Nuclease-free water was added to prepare the A-tailing reaction which was incubated at 37° C. for 40 min. 150.0 µL of Lysis/Binding Buffer (Thermo Fisher Scientific®, Waltham, MA) was added to the reaction. The entire volume was then added to 25.0 µL of Dynabeads™ oligo (dT) 25 (Thermo Fisher Scientific®, Waltham, MA) magnetic beads, which had been washed once with Lysis/Binding Buffer (Thermo Fisher Scientific®, Waltham, MA). The mixture was incubated at 25° C. and 600 RPM. The remainder of the procedure followed the steps of the protocol outlined in Example 1.

Sequencing: The samples were sequenced to obtain sequence reads using a NextSeq™ 500 sequencer by Illumina®. Sequencing was conducted following the manufacturer's instructions. The sequencing analysis was performed as described above in Example 1.

Results: FIG. 18A shows a normalized fragment length distribution of the microbes detected in the venous draw of two of the donors of this study, and FIG. 18B shows the normalized fragment length distributions of the microbes detected in the one of the replicate capillary draws from the same two donors. The two microbes detected in the venous draws (e.g. *Haemophilus influenzae* in Donor 1, and *Streptococcus thermophilus* in Donor 2) were detected in the biological samples obtained during the capillary draw collection process as well and showed a similar fragment length distribution in both collection types, i.e. a peaked fragment length distribution (FIG. 18A and FIG. 18B). The additional microbes detected in the samples obtained with the process applied during the capillary draw included a more diverse set of microbes (Table 3). The majority of these additional microbes co-occur in both replicates per each donor (FIG. 18C). In order to confirm that these additional microbes are not contributed by the contamination present in the Microvette® CB300 blood sampling devices used to collect the samples obtained from the procedure applied during the capillary draw or derived from the process contamination, we analyzed the sequencing data obtained from the Negative Microvette® Samples (see above). FIG. 18D shows the comparison of the abundance in units of MPM for the additional microbes in the biological sample obtained from the process applied during the capillary blood draw (x-axis) and the abundance in units of MPM for the same microbes in the Negative Microvette® Samples. The vast majority of the signal of the additional microbes in the data obtained from the capillary draw is not contributed by the tube contamination profile, and can be concluded to have derived from the biological sample obtained by collecting the blood drop from the fingertip. As the signal for these microbes was not detected in the venous draw, they must have originated from the skin surface over which the blood spread after the fingertip skin was lanced, suggesting that the skin-derived microbial nucleic acids show different properties of their fragment length distributions, e.g. the absence of a peak between 20 bp and 75 bp, and an exponential-like decay in the frequency of the fragments with fragment length. The same trends are observed in the other sample donors (data not shown).

TABLE 3

List of Microbial species Detected in the biological sample obtained from the process applied during the capillary blood draw for Donor 1 and Donor 2.

| Microbial species detected in Donor 1 | Microbial species detected in Donor 2 |
|---|---|
| *Altemaria arborescens* | *Acinetobacter baumannii* |
| *Bacteroides stercoris* | *Bacteroides ovatus* |
| *Bacteroides uniformis* | *Bacteroides stercoris* |
| *Bacteroides vulgatus* | *Bacteroides uniformis* |
| *Corynebacterium afermentans* | *Bacteroides vulgatus* |
| *Corynebacterium amycolatum* | *Corynebacterium aurimucosum* |
| *Corynebacterium aurimucosum* | *Corynebacterium simulans* |
| *Dermabacter hominis* | *Corynebacterium tuscaniense* |
| *Finegoldia magna* | *Facklamia hominis* |
| *Gardnerella vaginalis* | *Finegoldia magna* |
| *Lactobacillus iners* | *Lactobacillus crispatus* |
| *Malassezia globosa* | *Moraxella catarrhalis* |
| *Micrococcus lylae* | *Oligella urethralis* |
| *Peptoniphilus rhinitidis* | *Peptoniphilus* harei |
| *Propionibacterium granulosum* | *Saccharomyces cerevisiae* |
| *Rhodococcus fascians* | *Staphylococcus capitis* |
| *Staphylococcus capitis* | *Staphylococcus epidermidis* |

TABLE 3-continued

List of Microbial species Detected in the biological sample obtained from the process applied during the capillary blood draw for Donor 1 and Donor 2.

| Microbial species detected in Donor 1 | Microbial species detected in Donor 2 |
|---|---|
| *Staphylococcus epidermidis* | *Staphylococcus warned* |
| *Staphylococcus hominis* | *Streptococcus mitis* |
| *Streptococcus mitis* | *Streptococcus thermophilus* |
| *Streptococcus thermophilus* | |
| *Streptococcus tigurinus* | |

Example 10. Infection Post Transplant 10 transplant patients are monitored for possible infections post-transplant surgery, and the pathogens detected at the pre-symptomatic stage are monitored for the changes in their fragment length distribution to correlate the stage of infection with the observed fragment length. In particular, the presence of the peak between 20 bp and 75 bp as well as the fraction of fragments not associated with the peak is tracked as the infection progresses through different stages. In addition to these 10 transplant patients, 10 deindentified serial sampling sets from Karius production are selected in order to track the same behavior.

Example 11. Site of Localization Assessment 1000 deidentified samples from Karius production are spiked and processed along with the Assay Controls and Environmental Controls using template-switching based direct-to-library method with Proteinase K as described in U.S. Provisional 62/770,181. The 1000 deidentified samples include plasma samples from patients that have pneumonia, immunocompromised status, endocarditis, sepsis, or invasive fungal infection. Microbial abundance and microbial and host fragment length distributions are analyzed in order to relate features of the fragment length distributions (e.g. the presence or absence of the peak between 20 and 75 bp, the fraction of the reads longer than 65 bp, the fraction of the reads shorter than 40 bp) to the site of infection, in particular related to the presence of the peak in either a deep tissue infection or commensal.

Example 12. Infection Stage Determination from Microbial Fragment Length Distribution In order to determine the fragment length profile diagnostic predictability value for measuring a stage of infection, a set of clinical plasma samples were collected from 16 different consented subjects suspected of having an infection by drawing blood into PPT tubes and extracting plasma by a single centrifugation step according to the manufacturer's recommendations. The plasma samples were shipped frozen or at ambient temperature overnight to Karius lab in Redwood City, CA. For each subject, the first sample was obtained at the point of hospital admission at which point an orthogonal test (e.g. blood culture) was also performed to confirm the likely microbe species responsible or in part responsible for the infection. Subsequently, additional samples were drawn from the subjects at various time points during treatment to monitor the progress of infection and treatment effects. In total, the samples were collected at least at two time points per subject, including the time point of admission. The maximum number of time points per subject was 7. Plasma samples and Negative Control Samples were processed to nucleic acid libraries and sequenced as described above.

Figure 20A:
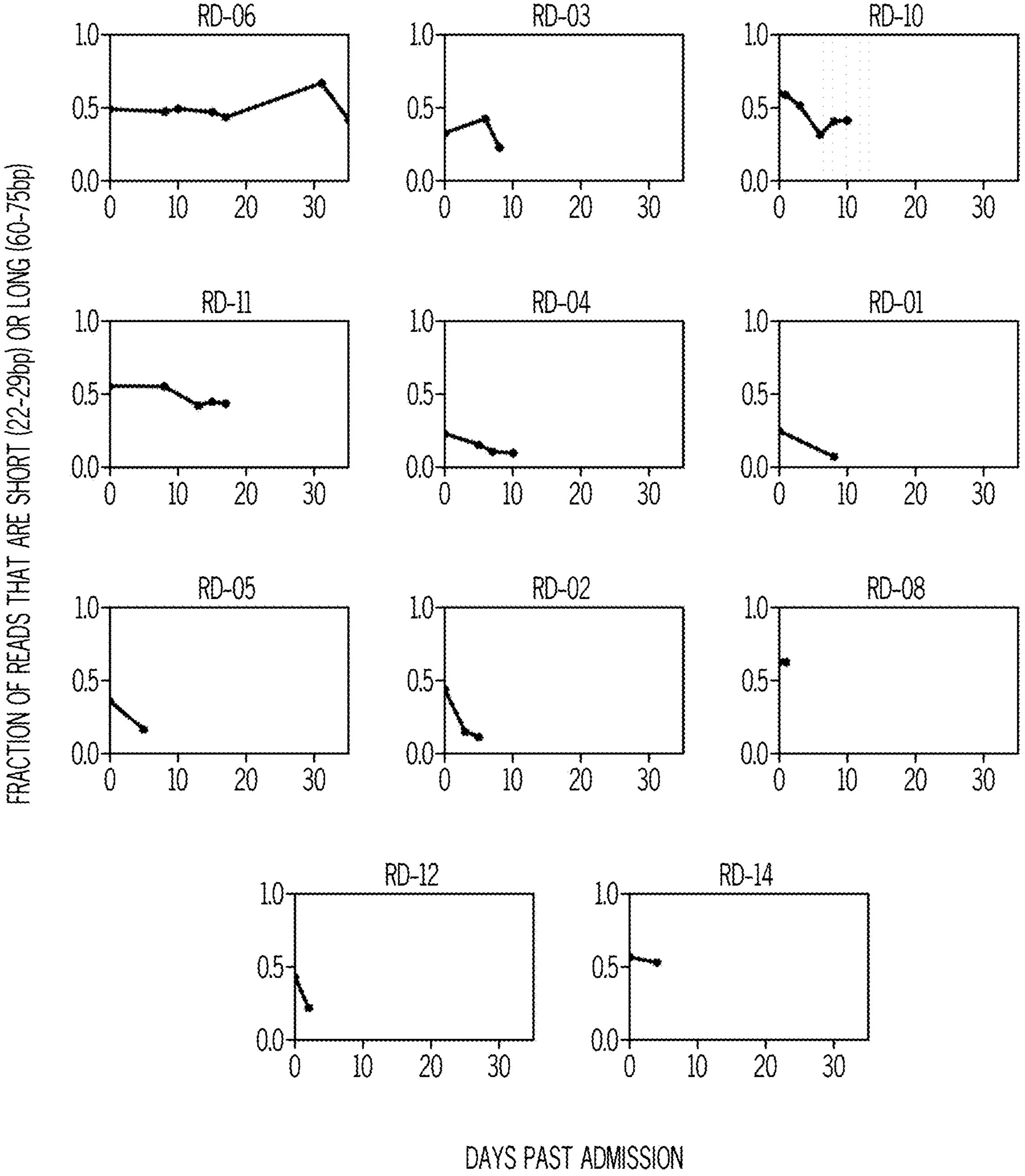
FIG. 20A depicts the fraction of reads outside of the "50 bp peak" region (<30 bp, and >60 bp) as a function of the time post admission for fragment length distributions of all the orthogonally confirmed microbes. Shown are only the time traces for the orthogonally confirmed microbes where more than 50 unique sequences aligning to the microbe's references were detected.
Figure 20B:
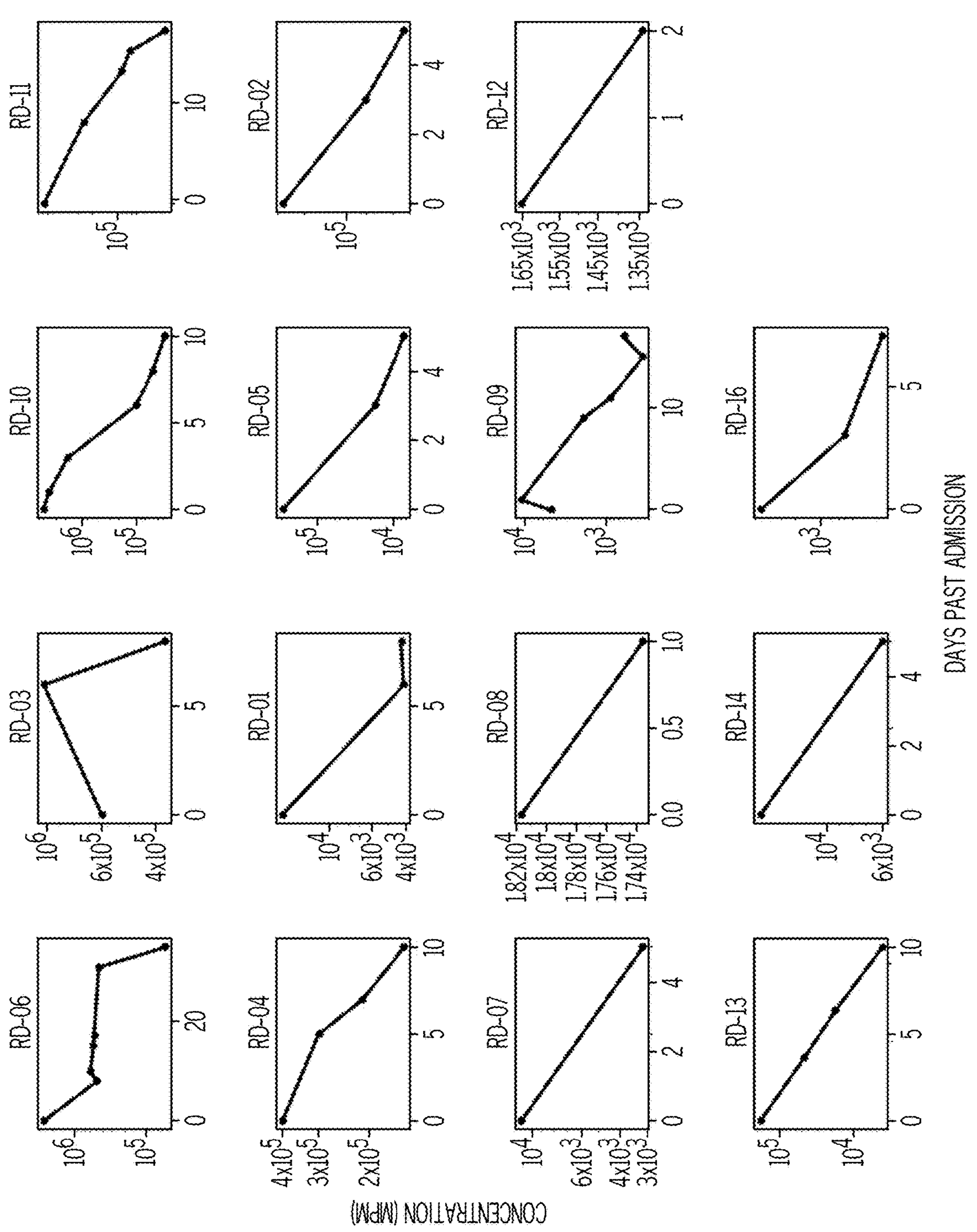
FIG. 20B depicts are the abundances in units of MPM as a function of the time post admission for all the orthogonally confirmed microbes that were detected by the method.

The group of subjects of this study included 3 patients orthogonally diagnosed with bloodstream infections, 8 patients orthogonally diagnosed with endocarditis, and 5 patients orthogonally diagnosed as febrile neutropenic patients. FIGS. 19A, 19B, and 19C show changes in the fragment length distribution in a representative case of a bloodstream infection, endocarditis, and febrile neutropenia, respectively. The example fragment length distributions in FIG. 19 indicate high probability for short exponentially distributed fragments (the range <40 bp), and increased probability for the peaked distribution around 50 bp after the treatment has started. The fraction of the short exponentially distributed or close-to-exponentially distributed fragments was therefore studied in all the processed samples. FIG. 20A depicts the kinetics of the changes in this short read fraction. This suggests that an invasive infection can be diagnosed based on the presence of the short and exponentially distributed read fraction, especially in the case of a bloodstream infection or bacteremia. In a single subject a high fraction of reads >64 bp was present, possibly indicating saturation of the mechanism that yields the short exponentially distributed fraction (data not shown). A concurrent measurement of microbial abundances (FIG. 20B) enables the determination of the infection stage by a combined use of abundance and fragment length profile measurements.

The sequencing data also indicates the presence of microbes not orthogonally confirmed by other microbiological tests performed. The fragment length distribution can be studied also in the case of these microbes. For example, *Haemophilus influenzae* and *Prevotella melaninogenica* were detected by the disclosed method in the admission samples from the subjects RD-06 and RD-13, respectively (FIG. 21A). While the orthogonally detected microbe, the presumed cause of the infection showed high short read fraction in both cases, the additional microbes showed variable trends; *Haemophilus influenzae* fragment length distribution was consistent with an invasive or bacteremic infection while *Prevotella melaninogenica* showed only the presence of a peaked distribution, consistent with an invisible stage of infection or commensal behaviour in asymptomatic patients (see e.g. *Helicobacter pylori* fragment length distribution in the U.S. Provisional Application No. 62/770,181, titled "Direct-to-Library Methods, Systems and Compositions", filed Nov. 21, 2018) or managed infection footprint. In addition, new microbes can emerge during the course of treatment, and fragment length analysis may assist in diagnosing the infection state of these as well. For example, FIG. 21B shows the fragment length distributions of the reads aligning to *Enterococcus gallinarum*, which show a detectable fraction of short exponentially distributed reads with a string peak fraction. The decision to treat this infection may be based on the magnitude of the short read fraction. The inspection of the clinical records confirmed that the subject was indeed treated for this infection.

Figure 22A:
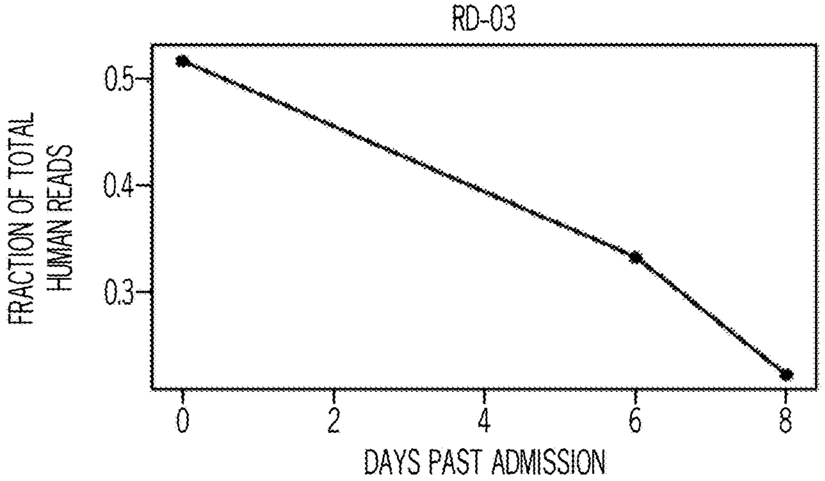
FIG. 22A-22C depict the three main modes of the response of the human fragment length distribution during a treatment of an infected subject.
Figure 22B:
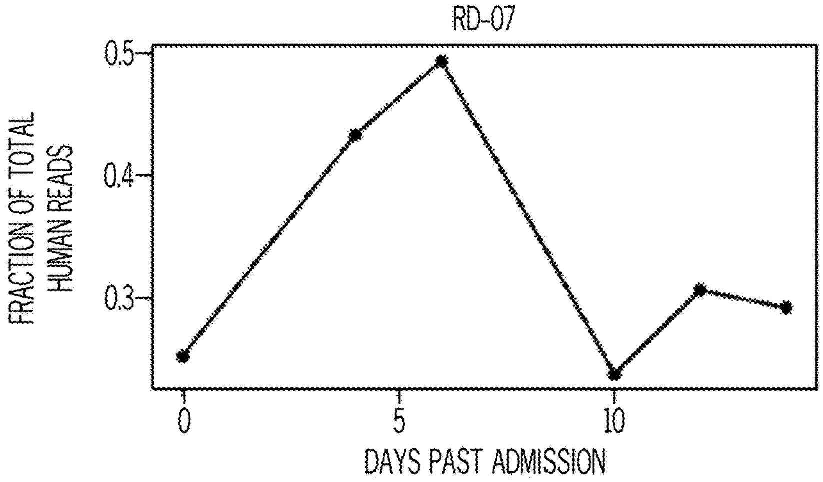
Figure 22C:
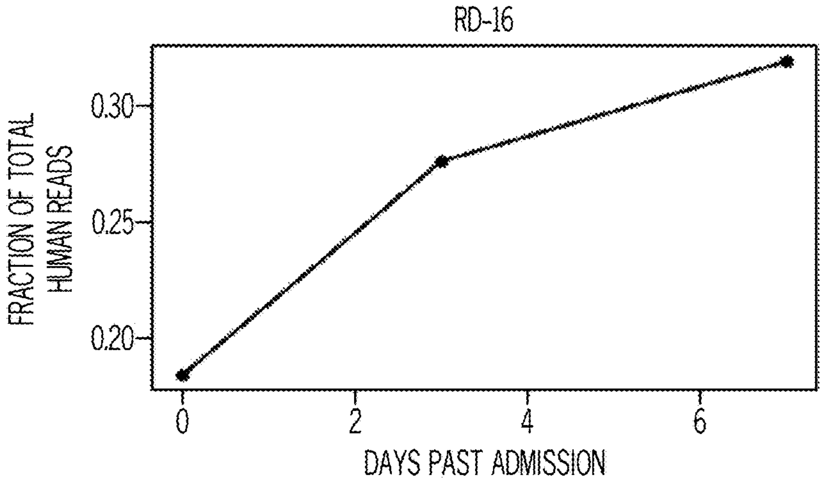
Figure 23:
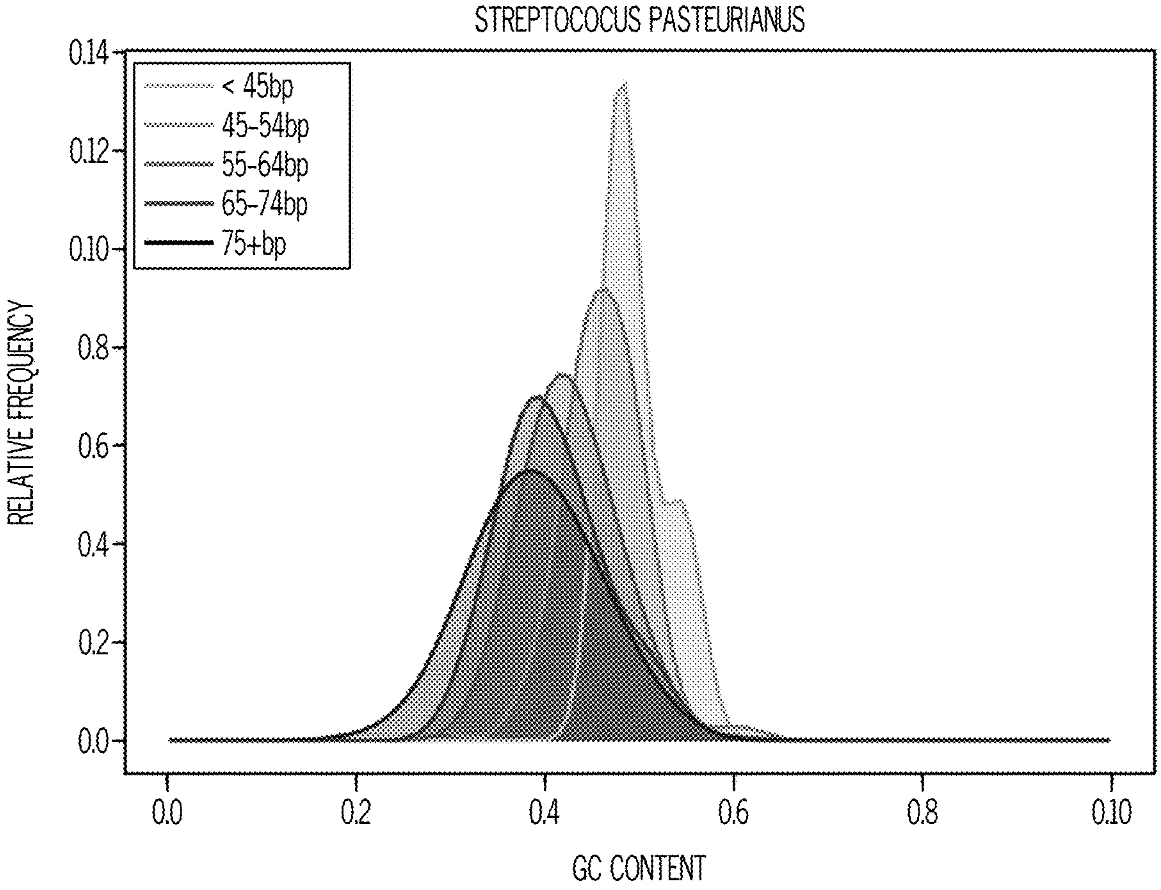
FIG. 23 provides a summary of fragment length information and GC content for samples from *Streptococcus pasteuranius*. Relative frequency is shown on the y axis; GC content is shown on the x-axis. Fragment length ranges of less than 45 base pairs, 45-54 base pairs, 55-64 base pairs, 65-74 base pairs, and longer than 74 base pairs are shown. The fragment length distribution in combination with the GC content information suggests a process induced temperature bias for this microbe.

Finally, the changes in the human fragment length distribution were analyzed as the studied subjects moved through the infection cycle from the symptomatic stage of infection at admission and diagnosis and through the treatment stage of the infection during therapy. FIG. 22 depicts the main three modes of behaviour of the human fragment distributions in infected patients studied here: (1) the fraction of the long (mainly nucleosomal) human reads decrease during treatment (FIG. 22A, 37.5% of total subjects in this study), (2) the fraction of the long human reads fluctuate during treatment (FIG. 22B, 37.5% of total subjects in this study), and (3) the fraction of the long (mainly nucleosomal) human reads increase during treatment (FIG. 22C, 37.5% of total subjects in this study 25%). As shown above, human fragment length distribution shape and properties can be predictive of an infection stage of a subject. The parameters derived from the human distribution can then be used in combination with the fragment length of the infecting microbe or other microbes detected in the sample to predict the recovery trajectory in a subject, e.g. if the subject is recovering, if another microbe infects a subject during the treatment for the initial infection, or recognize and invisible infection or commensal presence.

What is claimed is:

1. A method of preparing a biological fluid sample from a host for a fragmentomics analysis, the method comprising:

(a) denaturing a nucleic acid in the biological fluid sample to produce a denatured nucleic acid in the biological fluid sample;

(b) adding an adapter to the biological fluid sample, wherein the denatured nucleic acid in the biological fluid sample comprises a plurality of microbial cell-free nucleic acid fragments, and wherein the adapter comprises a nucleic acid residue overhang;

(c) attaching the adapter to a microbial cell-free nucleic acid fragment of the plurality of microbial cell-free nucleic acid fragments while the plurality of microbial cell-free nucleic acid fragments are in the biological fluid sample from the host, to produce an adapted nucleic acid, wherein the microbial cell-free nucleic acid fragment is not extracted from the biological fluid sample before the attaching the adapter;

(d) annealing a primer to the adapted nucleic acid to produce an annealed primer;

(e) extending the annealed primer with a polymerase to produce an extended nucleic acid;

(f) sequencing at least the extended nucleic acid to produce a plurality of microbial cell-free nucleic acid sequence reads; and (g) analyzing the plurality of microbial cell-free nucleic acid sequence reads for a fragment length characteristic selected from the group consisting of: a shape of a distribution, a segment amplitude, a peak shape, a fragment count ratio for two or more segments, a height of helical phasing peaks, a fragment count ratio at two different fragment lengths, a ratio of fragment counts within two different fragment length ranges, a fragment length range within a segment, a ratio of maximum amplitudes for two or more segments, and a fragment length distribution within a subset of reads.

2. The method of claim 1, further comprising, prior to (g), determining a length of each microbial cell-free nucleic acid fragment in the plurality of cell-free nucleic acid fragments based on the plurality of microbial cell-free nucleic acid sequence reads.

3. The method of claim 1, further comprising generating a fragment length profile for the microbial cell-free nucleic acid sequence reads using one or more of the fragment length characteristics.

4. The method of claim 3, wherein the fragment length profile corresponds to at least one subset of reads and further comprises:

(a) identifying the at least one subset of the reads within the microbial cell-free nucleic acid sequence reads, and (b) determining the fragment length profile within the at least one subset of reads.

5. The method of claim 3, wherein the generating the fragment length profile further comprises using two or more fragment length characteristics.

6. The method of claim 3, wherein the fragment length profile comprises at least one fragment length characteristic that comprises (a) a fragment count ratio for two or more peaks or (b) a fragment length distribution shape.

7. The method of claim 1, wherein the sequencing comprises next-generation sequencing.

8. The method of claim 1, wherein the sequencing comprises high-throughput sequencing.

9. The method of claim 1, wherein the biological fluid sample is a plasma sample or a bronchoalveolar lavage sample.

10. The method of claim 3, wherein the fragment length profile comprises an absence of a peak between 20 bp and 75 bp read lengths, a fraction of long reads (>64 bp) greater than 10%, or both.

11. The method of claim 1, wherein the host is human.

12. The method of claim 1, wherein the plurality of microbial cell-free nucleic acid fragments comprise bacterial cell-free nucleic acids, fungal cell-free nucleic acids, viral cell-free nucleic acids, parasitic cell-free nucleic acids, or any combination thereof.

13. The method of claim 11, wherein the human is infected with one or more microbes; and wherein the method further comprises administering a treatment to the human.

14. The method of claim 13, wherein the treatment comprises an antibiotic.

15. The method of claim 1, wherein the plurality of microbial cell-free nucleic acid fragments are single-stranded.

16. The method of claim 2, wherein the plurality of microbial cell-free nucleic acid fragments comprises at least 10,000 molecules.

17. The method of claim 1, wherein the analyzing the plurality of microbial cell-free nucleic acid sequence reads for the fragment length characteristic comprises determining one or more fragment length characteristics of at least 10,000 molecules from the microbial cell-free nucleic acid sequence reads.

18. The method of claim 3, further comprising identifying a microbe in the biological fluid sample based at least on a similarity of the fragment length profile as compared to a reference fragment length profile of the microbe.

19. The method of claim 1, wherein the plurality of microbial cell-free nucleic acid fragments comprise microbial cell-free DNA.

20. The method of claim 1, wherein the plurality of microbial cell-free nucleic acid fragments comprise microbial cell-free nucleic acids from *Helicobacter pylori*.

21. The method of claim 1, wherein the denaturing comprises heating the nucleic acid in the biological fluid sample to convert double-stranded nucleic acid molecules to single-stranded nucleic acid molecules.

22. The method of claim 1, wherein the biological fluid sample is a plasma sample.

* * * * *